United States Patent
MacDonald et al.

(10) Patent No.: US 10,513,557 B2
(45) Date of Patent: Dec. 24, 2019

(54) ANTI-ASIC1 ANTIBODIES AND USES THEREOF

(71) Applicant: Regeneron Pharmaceuticals, Inc., Tarrytown, NY (US)

(72) Inventors: Lynn MacDonald, White Plains, NY (US); Min Gao, Montvale, NJ (US); Marc R. Morra, Beacon Falls, CT (US); Nicole M. Alessandri-Haber, Rye, NY (US); Michael L. LaCroix-Fralish, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/719,220

(22) Filed: Sep. 28, 2017

(65) Prior Publication Data

US 2018/0222976 A1    Aug. 9, 2018

Related U.S. Application Data

(63) Continuation of application No. 14/848,452, filed on Sep. 9, 2015, now abandoned, which is a continuation of application No. 13/753,836, filed on Jan. 30, 2013, now Pat. No. 9,150,648.

(60) Provisional application No. 61/592,837, filed on Jan. 31, 2012, provisional application No. 61/692,925, filed on Aug. 24, 2012, provisional application No. 61/644,038, filed on May 8, 2012.

(51) Int. Cl.
| | |
|---|---|
| C12N 15/00 | (2006.01) |
| C12N 5/00 | (2006.01) |
| C12N 5/10 | (2006.01) |
| C12N 1/13 | (2006.01) |
| C12N 1/15 | (2006.01) |
| C12N 1/19 | (2006.01) |
| C12N 1/21 | (2006.01) |
| C12N 15/13 | (2006.01) |
| C12N 15/63 | (2006.01) |
| C07K 16/28 | (2006.01) |
| C07K 16/18 | (2006.01) |
| A61K 39/00 | (2006.01) |

(52) U.S. Cl.
CPC .............. *C07K 16/28* (2013.01); *C07K 16/18* (2013.01); *A61K 39/00* (2013.01); *A61K 2039/505* (2013.01); *C07K 2317/21* (2013.01); *C07K 2317/56* (2013.01); *C07K 2317/565* (2013.01); *C07K 2317/76* (2013.01); *C07K 2317/92* (2013.01); *C12N 5/00* (2013.01); *C12N 15/00* (2013.01)

(58) Field of Classification Search
None
See application file for complete search history.

(56) References Cited

U.S. PATENT DOCUMENTS

| | | |
|---|---|---|
| 6,287,859 B1 | 9/2001 | DeWeille |
| 6,635,432 B1 | 10/2003 | Welsh |
| 7,132,505 B1 | 11/2006 | Lazdunski |
| 7,288,251 B2 | 10/2007 | Bedian et al. |
| 7,488,806 B2 | 2/2009 | Papadopoulos et al. |
| 7,534,868 B1 | 5/2009 | Papadopoulos et al. |
| 7,547,521 B2 | 6/2009 | Seguela |
| 7,598,039 B2 | 10/2009 | Chen |
| 8,030,442 B2 | 10/2011 | Simon |
| 9,371,383 B2 | 6/2016 | Macdonald |
| 2003/0194404 A1 | 10/2003 | Greenfeder |
| 2006/0240001 A1 | 10/2006 | Bauer et al. |
| 2007/0087964 A1 | 4/2007 | Welsh |
| 2007/0197583 A1 | 8/2007 | Welsh |
| 2007/0280945 A1 | 12/2007 | Stevens |
| 2008/0146502 A1 | 6/2008 | Collier |
| 2008/0181899 A1 | 7/2008 | Papadopoulos |
| 2008/0279965 A1 | 11/2008 | Simon |
| 2009/0017035 A1* | 1/2009 | Papadopoulos ........ C07K 16/22 424/139.1 |
| 2009/0142354 A1 | 6/2009 | Papadopoulos et al. |
| 2009/0291150 A1 | 11/2009 | Welsh |
| 2010/0015127 A1 | 1/2010 | Fugger |
| 2011/0076284 A1 | 3/2011 | Corbin |

(Continued)

FOREIGN PATENT DOCUMENTS

| | | |
|---|---|---|
| EP | 0977844 | 2/1998 |
| EP | 1025226 | 12/2006 |
| EP | 1102844 | 11/2009 |

(Continued)

OTHER PUBLICATIONS

Paul, W.E. Fundamental Immunology, Third Edition (textbook), "Fv Structure and Diversity in Three Dimensions" pp. 292-295; Raven Press, New York (1993). (Year: 1993).*

(Continued)

*Primary Examiner* — Elizabeth C. Kemmerer
*Assistant Examiner* — Regina M DeBerry
(74) *Attorney, Agent, or Firm* — Adsero IP

(57) ABSTRACT

The present invention provides antibodies and antigen-binding fragments thereof that specifically bind to cells expressing acid-sensing ion channel-1 (ASIC1). According to certain embodiments of the invention, the antibodies inhibit acid-induced, ASIC1-mediated ion currents in cells expressing human ASIC1. The antibodies of the invention are useful for the treatment of pain, including pain associated with surgical intervention and various diseases and disorders.

27 Claims, 4 Drawing Sheets

Specification includes a Sequence Listing.

(56) References Cited

U.S. PATENT DOCUMENTS

2011/0152197 A1  6/2011  Deval

FOREIGN PATENT DOCUMENTS

| WO | WO 2003/008448 | 1/2003 |
| --- | --- | --- |
| WO | WO 2003/040170 | 5/2003 |
| WO | WO 2005/025518 | 3/2005 |
| WO | WO 2006/038070 | 4/2006 |
| WO | WO 2006/068953 | 6/2006 |
| WO | WO 2008/007131 | 1/2008 |
| WO | WO 2008/063676 | 5/2008 |
| WO | WO 2008/076379 | 6/2008 |
| WO | WO 2008/119360 | 10/2008 |
| WO | WO 2008/134659 | 11/2008 |
| WO | WO 2009/137686 | 11/2009 |
| WO | WO 2010/054007 | 5/2010 |
| WO | WO 2011/051349 | 5/2011 |
| WO | WO 2013/116296 A1 | 8/2013 |

OTHER PUBLICATIONS

Casset et al. A peptide mimetic of an anti-CD4 monoclonal antibody by rational design. Biochem Biophys Res Comm. vol. 307:198-205 (2003). (Year: 2003).*
Holm et al. Functional mapping and single chain construction of the anti-cytokeratin 8 monoclonal antibody TS1. Mol Immunol. vol. 44(6):1075-1084 (2007). (Year: 2007).*
MacCallum et al. Antibody-antigen interactions: Contact analysis and binding site topography. J Mol Biol. vol. 262:732-746 (1996). (Year: 1996).*
Vajdos et al. Comprehensive functional maps of the antigen-binding site of an anti-ErbB2 antibody obtained with shotgun scanning mutagenesis. J Mol Biol. 320(2):415-428 (2002). (Year: 2002).*
Tokuriki et al. Stability effects of mutations and protein evolvability; Current Opinion in Structural Biology, 19:596-604 (2009). (Year: 2009).*
Alvarez et al. (2002) Proceeding of the National Academy of Sciences 99(4):2326-2331 "Functional implications of the localization and activity of acid-sensitive channels in rat peripheral nervous system".
Alvarez et al. (2003) The Journal of Physiology 546(1):77-87 "Distribution, subcellular localization and ontogeny of ASIC1 in the mammalian central nervous system".
Bassler et al. (2001) J. Biological Chemistry 276(36):33782-33787 "Molecular and Functional Characterization of Acid-sensing Ion Channel (ASIC) 1b".
Calavia et al. (2010) Cellular and Molecular Neurobiolgy 30(6):841-848 "Differential Localization of Acid-Sensing Ion Channels 1 and 2 in Human Cutaneus Pacinian Corpuscles".
Casset et al. (2003) Biochem. Biophys. Res Comm. 307:198-205 "A peptide mimetic of an anti-CD4 monoclonal antibody by rational design".
Casset et al. (2003) Biochemical and Biophysical Research Communication 307:198-205 "A peptide mimetic of an anti-CD4 monoclonal antibody by rational design".
Cheng and Ji (2008) Neurochem Res. 33(10):1970-1978 "Intracellular signaling in primary sensory neurons and persistent pain".
Database GenBank: Accession ABU48925.1 Aug. 21, 2007.
Database GenBank Accession ACM68200 Feb. 10, 2009.
Database GenBank Accession ACN09180 Feb. 13, 2009.
Database GenBank Accession ADA14242 Dec. 14, 2009.
Database GenBank: Accession AEL59889 Dec. 28, 2006.
Database GenBank Accession BAF82699 Jan. 9, 2008.
Database GenBank Accession DJ568116 Aug. 24, 2012.
Database GenBank Accession GM667213 Dec. 5, 2008.
Database GenBank Accession HD112720 Aug. 11, 2010.
Davies et al. (1996) Immunotechnol. 2(3):169-179 "Affinity improvement of single antibody VH domains: residues in all three hypervariable regions affect antigen binding".

Diochot et al. (2007) Toxicon 49:271-284 "Peptides inhibitors of acid-sensing ion channels".
European Examination Report from EP App No. 13702876.7 dated Oct. 4, 2016.
Friese et al. (2007) Nature Medicine 13(12):1483-1489 "Acid-sensing ion channel-1 contributes to axonal degeneration in autoimmune inflammation of the central nervous system".
Gautam and Benson (2013) The FASEB Journal 27:793-802 "Acid-sensing ion channels (ASICs) in mouse skeletal muscle afferents are heteromers composed of ASIC1a, ASIC2, and ASIC3 subunits".
Grunder and Chen (2010) Int. J. Physiol Pathophysiol Pharmacol 2(2):73-94 "Structure, function, and pharmacology of acid-sensing ion channels (ASICs): focus on ASIC1a".
Holt et al. (2003) Trends in Biotechnology 21(11):484-490 "Domain antibodies: proteins for therapy".
International Search Report and Written Opinion dated Jul. 10, 2013 for Corresponding International Application No. PCT/US2013/023784.
Jasti et al. (2007) Nature 449:316-324 "Structure of acid-sensing ion channel 1 at 1.9 A resolution and low pH".
Jin et al. (2010) Molecular Brain, Biomed Central Ltd, London UK 3(1):39 "PICK1 regulates the trafficking of ASIC1a and acidotoxicity in a BAR domain lipid binding-dependent manner".
Julius and Basbaum (2001) Nature 413:203-210 "Molecular mechanisms of nociception".
Lingueglia (2007) J. Biological Chemistry 282(24):17325-17329 "Acid-sensing Ion Channels in Sensory Perception".
MacCallum et al. (1996) J. Mol. Biol. 262:732-745 "Antibody-antigen Interactions: Contact Analysis and Binding Site Topography".
Naves and McCleskey (2005) Brazillian J. Medical and Biological Research 38:1561-1569 "An acid-sensing ion channel that detects ischemic pain".
Ngo (1994) The Protein Folding Problem and Tertiary Structure Prediction p. 433-440 and p. 492-495 "Computational Complexity, Protein Structure Prediction and the Levinthal Paradox".
Paul (1993) Fundamental Immunology, Raven Press New York, 3rd Edition (textbook) pp. 292-295 "Fv Structure and Diversity in Three Dimensions".
Poirot, et al. (2006) J. Physiol. 576.01:215-234 "Distinct ASIC currents are expressed in rat putative nociceptors and are modulated by nerve injury".
Premkumar and Raisinghani (2006) Molecular Pain 2(26):1-7 "Nociceptors in cardiovascular functions: complex interplay as a result of cyclooxygenase inhibition".
Sanchez-Freire et al. (2011) Journal of Urology 186(4):1509-1516 "Acid-Sensing Channels in Human Bladder: Expression, Function and Alterations During Bladder Pain Syndrome".
Sun et al. (2011) Brain Research 1396:77-87 "ASICs mediate the modulatory effect by paeoniflorin on alpha-synuclein autophagic degratdation".
Tokuriki and Tawfik (2009) Current Opinion in Structural Biology 19:596-604 "Stability Effects of Mutations and Protein Evolvability".
Ugawa et al. (2002) J. Clinc.Invest. 110:1185-1190 "Amiloride-blockable acid-sensing ion channels are leading acid sensors expressed in human nociceptors".
Ugawa et al. (2011) Nagoya Med J 51(4):191-196 "Physiological roles of acid-sensing ion channels".
Walder et al. (2009) The Journal of Pain pp. 1-9 "ASIC1 and ASIC3 Play Different Roles in the Development of Hyperalgesia After Inflammatory Muscle Injury".
Waldmann et al. (1997) J. Biological Chemistry 272(34):20975-20978 "Molecular Cloning of a Non-inactivating Proton-gated Na+ Channel Spedific for Sensory Neurons".
Waldmann et al. (1997) Nature 386:173-177 "A proton-gated cation channel involved in acid-sensing".
Wells (1990) Biochemistry 29:8509-8517 "Additivity of Mutational Effects in Proteins".
Wemmie et al. (2003) Journal of Neuroscience 23(13): 5496-5502 "Acid-Sensing ion channel 1 is localized in brain regions with high synaptic density and contributes to fear conditioning".

(56) References Cited

OTHER PUBLICATIONS

Wu et al. (2004) J. Biological Chemsitry 279(42):43716-43724 "Characterization of Acid-sensing Ion Channels in Dorsal Horn Neurons of Rat Spinal Cord".
Xiong et al. (2008) Current Oppinion in Pharmacology 8:25-32 "Acid-sensing ion channels (ASICs) as pharmacological targets for neurodegenerative diseases".
Yokokawa et al. (2010) FEBS Letters 584(14):3107-3110 "Acid-sensing ion channel (ASIC) 1a undergoes a height transition in response to acidification".

* cited by examiner

SEQUENCE LISTING

```
<160> NUMBER OF SEQ ID NOS: 401

<210> SEQ ID NO 1
<211> LENGTH: 348
<212> TYPE: DNA
<213> ORGANISM: Artificial Sequence
<220> FEATURE:
<223> OTHER INFORMATION: Synthetic

<400> SEQUENCE: 1
caggtgcagc tggtgcagtc tggggctgaa gtgaagaagc ctggggcctc aatgaaggtc      60
tcctgcaagg cttctggata caccttcacc atttatgata tcaactgggt gcgccaggcc     120
actggacaag ggcttgagtg gatggggtgg atgaacccta ggagtggtag cacaggctat     180
tcacagaagt tccagggcag agtcaccatg accaggaaca cctccataaa cacagccttc     240
atggaactga gtagcctcag gtctgatgac acggccgtgt attactgtgt gagagggcaa     300
ctcgtcctgg gctactgggg ccagggaacc ctggtcaccg tctcctca                  348

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2
```

```
Gln Val Gln Leu Val Gln Ser Gly Ala Glu Val Lys Lys Pro Gly Ala
1               5                   10                  15

Ser Met Lys Val Ser Cys Lys Ala Ser Gly Tyr Thr Phe Thr Ile Tyr
            20                  25                  30

Asp Ile Asn Trp Val Arg Gln Ala Thr Gly Gln Gly Leu Glu Trp Met
        35                  40                  45

Gly Trp Met Asn Pro Arg Ser Gly Ser Thr Tyr Ser Gln Lys Phe
50                  55                  60

Gln Gly Arg Val Thr Met Thr Arg Asn Thr Ser Ile Asn Thr Ala Phe
65                  70                  75                  80

Met Glu Leu Ser Ser Leu Arg Ser Asp Asp Thr Ala Val Tyr Tyr Cys
                85                  90                  95

Val Arg Gly Gln Leu Val Leu Gly Tyr Trp Gly Gln Gly Thr Leu Val
            100                 105                 110

Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggatacacct tcaccattta tgat                                         24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Tyr Thr Phe Thr Ile Tyr Asp
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atgaacccta ggagtggtag caca                                         24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Met Asn Pro Arg Ser Gly Ser Thr
1               5

<210> SEQ ID NO 7
<211> LENGTH: 27
<212> TYPE: DNA
<213> ORGANISM: Artificial Sequence
```

<220> FEATURE:
<223> OTHER INFORMATION: Synthetic

<400> SEQUENCE: 7
gtgagagggc aactcgtcct gggctac    27

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Val Arg Gly Gln Leu Val Leu Gly Tyr
1               5

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacatcgtga tgacccagtc tccagactcc ctggctgtgt ctctgggcga gagggccacc     60
atcaactgca gtccagcca gagtgttgta tacagttcca ccctaagaa ctacttagct    120 tggtaccagc agaaaccagg acagcctcct aaactgctca tttactgggc atctacccgg    180
gaatccgggg tccctgaccg attcagtggc cgcgggtctg ggacagattt cactctcacc    240
atcagcagcc tgcaggctga agatgtggcg gtttattact gtcagcaata ttttttctact    300 ccgtacactt ttggccaggg gaccaagctg gagatcaaa                           339

<210> SEQ ID NO 10
<211> LENGTH: 113
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Asp Ser Leu Ala Val Ser Leu Gly
1               5                  10                  15

Glu Arg Ala Thr Ile Asn Cys Lys Ser Ser Gln Ser Val Val Tyr Ser
            20                  25                  30

Ser Thr Pro Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Arg Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Thr Pro Tyr Thr Phe Gly Gln Gly Thr Lys Leu Glu Ile
            100                 105                 110

Lys

<210> SEQ ID NO 11
<211> LENGTH: 36
<212> TYPE: DNA

<213> ORGANISM: Artificial Sequence
<220> FEATURE:
<223> OTHER INFORMATION: Synthetic

<400> SEQUENCE: 11
cagagtgttg tatacagttc cacccctaag aactac        36

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Val Val Tyr Ser Ser Thr Pro Lys Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 tgggcatct        9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Trp Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
cagcaatatt tttctactcc gtacact        27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Gln Tyr Phe Ser Thr Pro Tyr Thr
1               5

<210> SEQ ID NO 17
<211> LENGTH: 348
<212> TYPE: DNA
<213> ORGANISM: Artificial Sequence
<220> FEATURE:
<223> OTHER INFORMATION: Synthetic

<400> SEQUENCE: 17

```
caggtgcagc tggtgcagtc tggggctgag gtgaagaagc ctggggcctc agtgaaggtc      60
tcctgcaagg cttctggata caccttcacc atttatgata tcaactgggt gcgccaggcc     120
actggacaag gcttgagtg gatggggtgg atgaaccctg ggagtggtag cacaggctat     180
tcacagaagt tccagggcag agtcaccatg accaggaaca cctccataaa cacagccttc     240
atggagctga gtagcctcag atctgaggac acggccgtct attactgtgt gagagggcaa     300
ctcgtcctgg gctactgggg ccagggaacc ctggtcaccg tctcctca                  348
```

<210> SEQ ID NO 18
<211> LENGTH: 116
<212> TYPE: PRT
<213> ORGANISM: Artificial Sequence
<220> FEATURE:
<223> OTHER INFORMATION: Synthetic

<400> SEQUENCE: 18

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ile Tyr
            20                  25                  30

Asp Ile Asn Trp Val Arg Gln Ala Thr Gly Gln Gly Leu Glu Trp Met
        35                  40                  45

Gly Trp Met Asn Pro Arg Ser Gly Ser Thr Gly Tyr Ser Gln Lys Phe
    50                  55                  60

Gln Gly Arg Val Thr Met Thr Arg Asn Thr Ser Ile Asn Thr Ala Phe
65                  70                  75                  80

Met Glu Leu Ser Ser Leu Arg Ser Glu Asp Thr Ala Val Tyr Tyr Cys
                85                  90                  95

Val Arg Gly Gln Leu Val Leu Gly Tyr Trp Gly Gln Gly Thr Leu Val
            100                 105                 110

Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19

```
ggatacacct tcaccattta tgat                                             24
```

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

```
Gly Tyr Thr Phe Thr Ile Tyr Asp
1               5
```

<210> SEQ ID NO 21
<211> LENGTH: 24
<212> TYPE: DNA
<213> ORGANISM: Artificial Sequence
<220> FEATURE:

<223> OTHER INFORMATION: Synthetic

<400> SEQUENCE: 21
atgaacccta ggagtggtag caca                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Met Asn Pro Arg Ser Gly Ser Thr
1               5

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
gtgagagggc aactcgtcct gggctac                                       27

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Val Arg Gly Gln Leu Val Leu Gly Tyr
1               5

<210> SEQ ID NO 25
<211> LENGTH: 339
<212> TYPE: DNA
<213> ORGANISM: Artificial Sequence
<220> FEATURE:
<223> OTHER INFORMATION: Synthetic

<400> SEQUENCE: 25
gacatcgtga tgacccagtc tccagactcc ctggctgtgt ctctgggcga gagggccacc    60
atcaactgca gtccagccag agtgttgta tacagttcca acactaagaa ctacttagct    120
tggtaccagc agaaaccagg acagcctcct aacctgctca tttactgggc atctacccgg    180
gaatccgggg tccctgaccg attcagtggc cgcgggtctg ggacagattt cactctcacc    240
atcagcagcc tgcaggctga agatgtggcg gtttattact gtcagcaata tttttctact    300
ccgtacactt ttggccaggg gaccaagctg gagatcaaa                          339

<210> SEQ ID NO 26
<211> LENGTH: 113
<212> TYPE: PRT
<213> ORGANISM: Artificial Sequence
<220> FEATURE:
<223> OTHER INFORMATION: Synthetic

<400> SEQUENCE: 26

Asp Ile Val Met Thr Gln Ser Pro Asp Ser Leu Ala Val Ser Leu Gly
1               5                   10                  15

```
Glu Arg Ala Thr Ile Asn Cys Lys Ser Ser Gln Ser Val Val Tyr Ser
                20                  25                  30

Ser Asn Thr Lys Asn Tyr Leu Ala Trp Tyr Gln Gln Lys Pro Gly Gln
            35                  40                  45

Pro Pro Asn Leu Leu Ile Tyr Trp Ala Ser Thr Arg Glu Ser Gly Val
 50                  55                  60

Pro Asp Arg Phe Ser Gly Arg Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Phe Ser Thr Pro Tyr Thr Phe Gly Gln Gly Thr Lys Leu Glu Ile
            100                 105                 110

Lys

<210> SEQ ID NO 27
<211> LENGTH: 36
<212> TYPE: DNA
<213> ORGANISM: Artificial Sequence
<220> FEATURE:
<223> OTHER INFORMATION: Synthetic

<400> SEQUENCE: 27
cagagtgttg tatacagttc caacactaag aactac                                 36

<210> SEQ ID NO 28
<211> LENGTH: 12
<212> TYPE: PRT
<213> ORGANISM: Artificial Sequence
<220> FEATURE:
<223> OTHER INFORMATION: Synthetic

<400> SEQUENCE: 28

Gln Ser Val Val Tyr Ser Ser Asn Thr Lys Asn Tyr
 1               5                  10

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 tgggcatct                                                                9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Trp Ala Ser
 1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
```

```
cagcaatatt tttctactcc gtacact                                           27
```

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

```
Gln Gln Tyr Phe Ser Thr Pro Tyr Thr
1               5
```

<210> SEQ ID NO 33
<211> LENGTH: 348
<212> TYPE: DNA
<213> ORGANISM: Artificial Sequence
<220> FEATURE:
<223> OTHER INFORMATION: Synthetic

<400> SEQUENCE: 33

```
gaggtgcagc tgttggagtc tgggggaggc ttggtacagc ctggggggtc cctgagactc        60
tcctgtgcag cctctggatt cacctttagc agctttgcca tgagctgggt ccgccaggct       120
ccagggaagg gactggagtg ggtctcaggt attagtggta gtggtggtgg cacacactac       180
gcagactccg tgaagggccg gttcaccatc tccagagaca attcgaagaa catggtgtat       240
ctgcaaatga acagcctgag agccgaggac acggccgcat attactgtgc gaaagaggcc       300
tataaatggc agccctgggg ccagggaacc ctggtcaccg tctcctca                   348
```

<210> SEQ ID NO 34
<211> LENGTH: 116
<212> TYPE: PRT
<213> ORGANISM: Artificial Sequence
<220> FEATURE:
<223> OTHER INFORMATION: Synthetic

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Thr His Tyr Ala Asp Ser Val
    50                  55                  60

Lys Gly Arg Phe Thr Ile Ser Arg Asp Asn Ser Lys Asn Met Val Tyr
65                  70                  75                  80

Leu Gln Met Asn Ser Leu Arg Ala Glu Asp Thr Ala Ala Tyr Tyr Cys
                85                  90                  95

Ala Lys Glu Ala Tyr Lys Trp Gln Pro Trp Gly Gln Gly Thr Leu Val
            100                 105                 110

Thr Val Ser Ser
        115
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

```
<400> SEQUENCE: 35
ggattcacct ttagcagctt tgcc                                              24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Ser Phe Ala
1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagtggta gtggtggtgg caca                                              24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38

Ile Ser Gly Ser Gly Gly Gly Thr
1               5

<210> SEQ ID NO 39
<211> LENGTH: 27
<212> TYPE: DNA
<213> ORGANISM: Artificial Sequence
<220> FEATURE:
<223> OTHER INFORMATION: Synthetic

<400> SEQUENCE: 39
gcgaaagagg cctataaatg gcagccc                                           27

<210> SEQ ID NO 40
<211> LENGTH: 9
<212> TYPE: PRT
<213> ORGANISM: Artificial Sequence
<220> FEATURE:
<223> OTHER INFORMATION: Synthetic

<400> SEQUENCE: 40

Ala Lys Glu Ala Tyr Lys Trp Gln Pro
1               5

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gacatccaga tgacccagtc tccttccacc ctgtctgcat ctgtgggaga cagagtcatc       60
```

```
atcacttgcc gggccagtca gaggattagt agctggttgg cctggtatca acagaaacca    120
gggaaagccc ctaacctcct gatctataag gcgtctattt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtacac ttttggccag    300
gggaccaaac tggagatcaa a                                              321
```

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

```
Asp Ile Gln Met Thr Gln Ser Pro Ser Thr Leu Ser Ala Ser Val Gly
1               5                   10                  15

Asp Arg Val Ile Ile Thr Cys Arg Ala Ser Gln Arg Ile Ser Ser Trp
            20                  25                  30

Leu Ala Trp Tyr Gln Gln Lys Pro Gly Lys Ala Pro Asn Leu Leu Ile
        35                  40                  45

Tyr Lys Ala Ser Ile Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43

```
cagaggatta gtagctgg                                                   18
```

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

```
Gln Arg Ile Ser Ser Trp
1               5
```

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45

```
aaggcgtct                                                              9
```

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Lys Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
caacagtata atagttattc gtacact                                          27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln Gln Tyr Asn Ser Tyr Ser Tyr Thr
1               5

<210> SEQ ID NO 49
<211> LENGTH: 348
<212> TYPE: DNA
<213> ORGANISM: Artificial Sequence
<220> FEATURE:
<223> OTHER INFORMATION: Synthetic

<400> SEQUENCE: 49
gaggtgcagc tgttggcgtc tgggggaggc ttggtacaga ctggggggtc cctgagactc      60
tcctgtgcag cctctggatt cacctttagt agctttgcca tgagctgggt ccgccaggct     120
ccagggaagg ggctggagtg ggtctcaggt attagtggta gtggtggtag cacatactac     180
gcagactccg tgaagggccg gttcaccatc tccagagaca attccaagaa cacgctgtat     240
ctgcaaatga acagcctgag agccgaggac acggccgcat attattgtgc gaaagaggcc     300
tataaatggc agccctgggg ccagggaatc cgggtcaccg tctcctca                 348

<210> SEQ ID NO 50
<211> LENGTH: 116
<212> TYPE: PRT
<213> ORGANISM: Artificial Sequence
<220> FEATURE:
<223> OTHER INFORMATION: Synthetic

<400> SEQUENCE: 50

Glu Val Gln Leu Leu Ala Ser Gly Gly Gly Leu Val Gln Thr Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

```
Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Ala Tyr Tyr Cys
                 85                  90                  95

Ala Lys Glu Ala Tyr Lys Trp Gln Pro Trp Gly Gln Gly Ile Arg Val
            100                 105                 110

Thr Val Ser Ser
        115

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct ttagtagctt tgcc                                            24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Ser Phe Ala
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
attagtggta gtggtggtag caca                                            24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Ser Gly Ser Gly Gly Ser Thr
1               5

<210> SEQ ID NO 55
<211> LENGTH: 27
<212> TYPE: DNA
<213> ORGANISM: Artificial Sequence
<220> FEATURE:
<223> OTHER INFORMATION: Synthetic

<400> SEQUENCE: 55
gcgaaagagg cctataaatg gcagccc                                         27

<210> SEQ ID NO 56
```

```
<211> LENGTH: 9
<212> TYPE: PRT
<213> ORGANISM: Artificial Sequence
<220> FEATURE:
<223> OTHER INFORMATION: Synthetic

<400> SEQUENCE: 56

Ala Lys Glu Ala Tyr Lys Trp Gln Pro
1               5

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccttccacc ctgtctgctt ctgtgggaga cagagtcacc      60
atcacttgcc gggccagtca gagtattagt agctggttgg cctggtatca gcagaaacca     120
gggaaagccc ctaacctcct gatctataag acgtctaatt tagaaagtgg ggtcccatca     180
aggttcagcg gcagtggatc tgggacagaa ttcactctca ccatcagcag cctgcagcct     240
gatgattttg caacttatta ctgccaacag tataatagtt attcgtacac ttttggccag     300
gggaccaagc tggagatcaa a                                               321

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Asn Leu Leu Ile
        35                  40                  45

Tyr Lys Thr Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagagtatta gtagctgg                                                    18

<210> SEQ ID NO 60
<211> LENGTH: 6
```

<212> TYPE: PRT
<213> ORGANISM: Artificial Sequence
<220> FEATURE:
<223> OTHER INFORMATION: Synthetic

<400> SEQUENCE: 60

Gln Ser Ile Ser Ser Trp
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 aagacgtct                                                                  9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Thr Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata atagttattc gtacact                                             27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Ser Tyr Ser Tyr Thr
1               5

<210> SEQ ID NO 65
<211> LENGTH: 366
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtccagc ctgggggtc cctgaaactc          60 tcctgtgcag cctctggatt cacctttagt agcttttgga tgagctgggt ccgccaggct        120
ccagggaagg ggctggagtg ggtggccaat ataaagcaaa atggaagtga gacatactat        180
gtggactctg tgaagggccg attcaccatc tccagagaca caccaagaa ctcactgtat        240 ctgcaaatga acagcctgag agccgaggac acggctatat attactgtgc gagagggggg       300

```
cggatacagc tatggtctag ctggttcgac ccctggggcc agggaaccct ggtcaccgtc      360
tcctca                                                                 366
```

```
<210> SEQ ID NO 66
<211> LENGTH: 122
<212> TYPE: PRT
<213> ORGANISM: Artificial Sequence
<220> FEATURE:
<223> OTHER INFORMATION: Synthetic

<400> SEQUENCE: 66
```

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Asn Ile Lys Gln Asn Gly Ser Glu Thr Tyr Tyr Val Asp Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Arg Ile Gln Leu Trp Ser Ser Trp Phe Asp Pro Trp
            100                 105                 110

Gly Gln Gly Thr Leu Val Thr Val Ser Ser
        115                 120
```

```
<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct ttagtagctt ttgg                                              24
```

```
<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Ser Phe Trp
1               5
```

```
<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
ataaagcaaa atggaagtga gaca                                              24
```

```
<210> SEQ ID NO 70
<211> LENGTH: 8
```

<212> TYPE: PRT
<213> ORGANISM: Artificial Sequence
<220> FEATURE:
<223> OTHER INFORMATION: Synthetic

<400> SEQUENCE: 70

Ile Lys Gln Asn Gly Ser Glu Thr
1               5

<210> SEQ ID NO 71
<211> LENGTH: 45
<212> TYPE: DNA
<213> ORGANISM: Artificial Sequence
<220> FEATURE:
<223> OTHER INFORMATION: Synthetic

<400> SEQUENCE: 71
gcgagagggg ggcggataca gctatggtct agctggttcg acccc                45

<210> SEQ ID NO 72
<211> LENGTH: 15
<212> TYPE: PRT
<213> ORGANISM: Artificial Sequence
<220> FEATURE:
<223> OTHER INFORMATION: Synthetic

<400> SEQUENCE: 72

Ala Arg Gly Gly Arg Ile Gln Leu Trp Ser Ser Trp Phe Asp Pro
1               5                   10                  15

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcctcc ctgtcagcat ctgtaggaga cagagtcacc      60
atcacttgcc gggcaagtca gagcattaaa aactatttaa attggtatca gcagaaatca     120
gggaaagccc ctaaactcct gatctatgct gcatccagtt tgcaaagtgg ggtcccatca     180
agggtcagtg gcagtggatc tgggacagat ttcactctca ccatcagcag tctgcaccct     240
gaagattttg cagcttacta ctgtcaacag agtttcagtg ccccgctcac tttcggcgga     300
gggaccaagg tggagatcaa a                                               321

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys Asn Tyr
            20                  25                  30

Leu Asn Trp Tyr Gln Gln Lys Ser Gly Lys Ala Pro Lys Leu Leu Ile
        35                  40                  45

Tyr Ala Ala Ser Ser Leu Gln Ser Gly Val Pro Ser Arg Val Ser Gly
    50                  55                  60

Ser Gly Ser Gly Thr Asp Phe Thr Leu Thr Ile Ser Ser Leu His Pro
65                  70                  75                  80

Glu Asp Phe Ala Ala Tyr Tyr Cys Gln Gln Ser Phe Ser Ala Pro Leu
                85                  90                  95

Thr Phe Gly Gly Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagagcatta aaaactat                                                    18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Ser Ile Lys Asn Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc                                                               9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
caacagagtt tcagtgcccc gctcact                                          27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Ser Phe Ser Ala Pro Leu Thr
1               5

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
gaggagctag tgttggaatc tggggaggc ttggtacagc ctgggggtc cctgagactc    60 tcctgtgcag cctctggatt catgtttagc acctatgcca tgagctgggt ccgccaggct   120
ccagggaagg gctggagtg gtctcactt attagtggtc gtgacggtag cacatactat   180
gcagactccg tgaagggccg gttcaccatc tccagagaca tttccaggaa cacgctctat   240
ctacacttga acagcctgcg agccgaggac acggccgtat attactgtgc gaaagataca   300
gctgtggttc ctggctacgg tttggacgtc tggggccaag ggaccacggt caccgtctcc   360
tca                                                                363

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Glu Glu Leu Val Leu Glu Ser Gly Gly Gly Leu Val Gln Pro Gly Gly
1               5                   10                  15

Ser Leu Arg Leu Ser Cys Ala Ala Ser Gly Phe Met Phe Ser Thr Tyr
            20                  25                  30

Ala Met Ser Trp Val Arg Gln Ala Pro Gly Lys Gly Leu Glu Trp Val
        35                  40                  45

Ser Leu Ile Ser Gly Arg Asp Gly Ser Thr Tyr Tyr Ala Asp Ser Val
    50                  55                  60

Lys Gly Arg Phe Thr Ile Ser Arg Asp Ile Ser Arg Asn Thr Leu Tyr
65                  70                  75                  80

Leu His Leu Asn Ser Leu Arg Ala Glu Asp Thr Ala Val Tyr Tyr Cys
                85                  90                  95

Ala Lys Asp Thr Ala Val Val Pro Gly Tyr Gly Leu Asp Val Trp Gly
            100                 105                 110

Gln Gly Thr Thr Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcatgt ttagcaccta tgcc                                          24

<210> SEQ ID NO 84
<211> LENGTH: 8
<212> TYPE: PRT

```
<213> ORGANISM: Artificial Sequence
<220> FEATURE:
<223> OTHER INFORMATION: Synthetic

<400> SEQUENCE: 84

Gly Phe Met Phe Ser Thr Tyr Ala
1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attagtggtc gtgacggtag caca                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Gly Arg Asp Gly Ser Thr
1               5

<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87
gcgaaagata cagctgtggt tcctggctac ggtttggacg tc                      42

<210> SEQ ID NO 88
<211> LENGTH: 14
<212> TYPE: PRT
<213> ORGANISM: Artificial Sequence
<220> FEATURE:
<223> OTHER INFORMATION: Synthetic

<400> SEQUENCE: 88

Ala Lys Asp Thr Ala Val Val Pro Gly Tyr Gly Leu Asp Val
1               5                   10

<210> SEQ ID NO 89
<211> LENGTH: 321
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tcctgccacc ctgtctgcat ctgtaggaga cagagtcacc    60
atcacttgcc gggccagtca gactattagt aactggttgg cctggtatca gcagagacca   120
gggaaagccc ctaagctcct gatctataag gcgtctagtt tagaaactgg ggtcccatca   180
aggttcagcg gcagtggatc tgggacagaa ttcactctca ccatcagcag cctgcagcct   240
gatgattttg caagttatta ctgccaacag tataatagtt attcgtggac gttcggccaa   300
```

```
gggaccaagg tggaaatcaa a                                              321
```

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

```
Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Thr Ile Ser Asn Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asn Ser Tyr Ser Trp
                85                  90                  95

Thr Phe Gly Gln Gly Thr Lys Val Glu Ile Lys
            100                 105
```

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91

```
cagactatta gtaactgg                                                   18
```

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

```
Gln Thr Ile Ser Asn Trp
1               5
```

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93

```
aaggcgtct                                                              9
```

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Lys Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: Synthetic

<400> SEQUENCE: 95
caacagtata atagttattc gtggacg                                    27

<210> SEQ ID NO 96
<211> LENGTH: 9
<212> TYPE: PRT
<213> ORGANISM: Artificial Sequence
<220> FEATURE:
<223> OTHER INFORMATION: Synthetic

<400> SEQUENCE: 96

Gln Gln Tyr Asn Ser Tyr Ser Trp Thr
1               5

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97
gaggagctag tgttggaatc tgggggaggc ttggtacagc ctgggggtc cctgagactc      60 tcctgtgcag cctctggatt catgtttagc acctatgcca tgagctgggt ccgccaggct    120
ccagggaagg ggctggagtg ggtctcactt attagtggtc gtgacggtaa cacatactat    180
gcagactccg tgaagggccg gttcaccatc tccagagaca attccaggaa cacgctctat    240
ctacaattga acagcctgcg agccgaggac acggccttat attactgtgc gaaagataca    300
gctgtggttc ctggctacgg tatggacgtc tggggccaag ggaccacggt caccgtctcc    360
tca                                                                  363

<210> SEQ ID NO 98
<211> LENGTH: 121
<212> TYPE: PRT
<213> ORGANISM: Artificial Sequence
<220> FEATURE:
<223> OTHER INFORMATION: Synthetic

<400> SEQUENCE: 98

Glu Glu Leu Val Leu Glu Ser Gly Gly Gly Leu Val Gln Pro Gly Gly
1               5                   10                  15

Ser Leu Arg Leu Ser Cys Ala Ala Ser Gly Phe Met Phe Ser Thr Tyr
            20                  25                  30

Ala Met Ser Trp Val Arg Gln Ala Pro Gly Lys Gly Leu Glu Trp Val
        35                  40                  45

Ser Leu Ile Ser Gly Arg Asp Gly Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Leu Asn Ser Leu Arg Ala Glu Asp Thr Ala Leu Tyr Tyr Cys 85                  90                  95
Ala Lys Asp Thr Ala Val Val Pro Gly Tyr Gly Met Asp Val Trp Gly
            100                 105                 110

Gln Gly Thr Thr Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcatgt ttagcaccta tgcc                                          24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Met Phe Ser Thr Tyr Ala
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggtc gtgacggtaa caca                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Arg Asp Gly Asn Thr
1               5

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gcgaaagata cagctgtggt tcctggctac ggtatggacg tc                      42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Ala Lys Asp Thr Ala Val Val Pro Gly Tyr Gly Met Asp Val
1               5                   10

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tcctgccacc ctgtctgcat ctgtaggaga cagagtcacc    60
atcacttgcc gggccagtca gactattagt aactggttgg cctggtatca gcagagacca   120
gggaaagccc ctaagctcct gatctataag gcgtctagtt tagaaactgg ggtcccatca   180
aggttcagcg gcagtggatc tgggacagaa ttcactctca ccatcagcag cctgcagcct   240
gatgattttg caagttatta ctgccaacag tataatagtt attcgtggac gttcggccaa   300
gggaccaagg tggaaatcaa a                                             321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ala Thr Leu Ser Ala Ser Val Gly
1               5                   10                  15

Asp Arg Val Thr Ile Thr Cys Arg Ala Ser Gln Thr Ile Ser Asn Trp
            20                  25                  30

Leu Ala Trp Tyr Gln Gln Arg Pro Gly Lys Ala Pro Lys Leu Leu Ile
        35                  40                  45

Tyr Lys Ala Ser Ser Leu Glu Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asn Ser Tyr Ser Trp
                85                  90                  95

Thr Phe Gly Gln Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagactatta gtaactgg                                                  18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 aaggcgtct                                                                                      9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Lys Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
caacagtata atagttattc gtggacg                                                                 27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Gln Gln Tyr Asn Ser Tyr Ser Trp Thr
1               5

<210> SEQ ID NO 113
<211> LENGTH: 366
<212> TYPE: DNA
<213> ORGANISM: Artificial Sequence
<220> FEATURE:
<223> OTHER INFORMATION: Synthetic

<400> SEQUENCE: 113
gaggtgcagc tggtggagtc tgggggaggc ttggtccagc ctggggggtc cctgaaactc      60
tcctgtgcag cctctggatt cacctttagt agcttttgga tgagctgggt ccgccaggct     120
ccagggaagg ggctggagtg ggtggccaat ataaagcaaa atggaagtga gacatactat     180
gtggactctg tgaagggccg attcaccatc tccagagaca caccaagaa ctcactgtat      240 ctgcaaatga acagcctgag agccgaggac acggctatat attactgtgc gagaggggg     300 cggatacagc tatggtctag ctggttcgac ccctgggcc agggaaccct ggtcaccgtc      360
tcctca                                                                                    366

<210> SEQ ID NO 114

Gln Thr Ile Ser Asn Trp
1               5

```
<211> LENGTH: 122
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Asn Ile Lys Gln Asn Gly Ser Glu Thr Tyr Tyr Val Asp Ser Val
    50                  55                  60

Lys Gly Arg Phe Thr Ile Ser Arg Asp Asn Thr Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Arg Gly Gly Arg Ile Gln Leu Trp Ser Ser Trp Phe Asp Pro Trp
            100                 105                 110

Gly Gln Gly Thr Leu Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttagtagctt ttgg                                          24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Ser Ser Phe Trp
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
ataaagcaaa atggaagtga gaca                                          24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118
```

Ile Lys Gln Asn Gly Ser Glu Thr
1               5

<210> SEQ ID NO 119
<211> LENGTH: 45
<212> TYPE: DNA
<213> ORGANISM: Artificial Sequence
<220> FEATURE:
<223> OTHER INFORMATION: Synthetic

<400> SEQUENCE: 119
gcgagagggg ggcggataca gctatggtct agctggttcg acccc      45

<210> SEQ ID NO 120
<211> LENGTH: 15
<212> TYPE: PRT
<213> ORGANISM: Artificial Sequence
<220> FEATURE:
<223> OTHER INFORMATION: Synthetic

<400> SEQUENCE: 120

Ala Arg Gly Gly Arg Ile Gln Leu Trp Ser Ser Trp Phe Asp Pro
1               5                   10                  15

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121
gccatccaga tgacccagtc tccatcctcc ctgtctgcat ctgtaggaga cagagtcacc      60
attacttgcc gggcaagtca gggcattagc aatgatttag ctggtatca gcagaaacca     120
gggaaagccc ctaaactcct gatctatggt gcatccagtt tacaaactgg ggtcccatca    180
aggttcagcg gcagtggatc tggcacagat ttcactctca ccatcagcag cctgcagcct    240
gaagattttg caacttatta ctgtctacaa gatttcaatt acccgtacac ttttggccag    300
gggaccaaac tggagatcaa a                                              321

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asp
                20                  25                  30

Leu Gly Trp Tyr Gln Gln Lys Pro Gly Lys Ala Pro Lys Leu Leu Ile
            35                  40                  45

Tyr Gly Ala Ser Ser Leu Gln Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Phe Asn Tyr Pro Tyr
                85                  90                  95

Thr Phe Gly Gln Gly Thr Lys Leu Glu Ile Lys

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cagggcatta gcaatgat                                                    18

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

Gln Gly Ile Ser Asn Asp
1               5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 ggtgcatcc                                                               9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Gly Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
ctacaagatt tcaattaccc gtacact                                          27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Leu Gln Asp Phe Asn Tyr Pro Tyr Thr
1               5

<210> SEQ ID NO 129

<211> LENGTH: 348
<212> TYPE: DNA
<213> ORGANISM: Artificial Sequence
<220> FEATURE:
<223> OTHER INFORMATION: Synthetic

<400> SEQUENCE: 129

```
gaggtgcagc tgttggcgtc tgggggaggc ttggtacagc ctggggggtc cctgagactc      60
tcctgtgcag cctctggatt cacctttagt agctttgcca tgagctgggt ccgccaggct     120
ccagggaagg ggctggagtg ggtctcaggt attagtggta gtggtgttag cacatactac     180
gcagactccg tgaagggccg gttcaccatc tccagagaca attccaagaa cacgctgtat     240
ctgcaaatga acagcctgag agccgaggac acggccgcat attattgtgc gaaagaggcc     300
tataaatggc agccctgggg ccagggaatc cgggtcaccg tctcctca                  348
```

<210> SEQ ID NO 130
<211> LENGTH: 116
<212> TYPE: PRT
<213> ORGANISM: Artificial Sequence
<220> FEATURE:
<223> OTHER INFORMATION: Synthetic

<400> SEQUENCE: 130

```
Glu Val Gln Leu Leu Ala Ser Gly Gly Gly Leu Val Gln Pro Gly Gly
1               5                   10                  15
Ser Leu Arg Leu Ser Cys Ala Ala Ser Gly Phe Thr Phe Ser Ser Phe
            20                  25                  30
Ala Met Ser Trp Val Arg Gln Ala Pro Gly Lys Gly Leu Glu Trp Val
        35                  40                  45
Ser Gly Ile Ser Gly Ser Gly Val Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Ala Tyr Tyr Cys
                85                  90                  95
Ala Lys Glu Ala Tyr Lys Trp Gln Pro Trp Gly Gln Gly Ile Arg Val
            100                 105                 110
Thr Val Ser Ser
        115
```

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131

```
ggattcacct ttagtagctt tgcc                                              24
```

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

```
Gly Phe Thr Phe Ser Ser Phe Ala
1               5
```

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attagtggta gtggtgttag caca                                          24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Ser Gly Ser Gly Val Ser Thr
1               5

<210> SEQ ID NO 135
<211> LENGTH: 27
<212> TYPE: DNA
<213> ORGANISM: Artificial Sequence
<220> FEATURE:
<223> OTHER INFORMATION: Synthetic

<400> SEQUENCE: 135
gcgaaagagg cctataaatg gcagccc                                       27

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Ala Lys Glu Ala Tyr Lys Trp Gln Pro
1               5

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccttccacc ctgtctgcat ctgtgggaga cagagtcacc    60
atcacttgcc gggccagtca gagtattagt agctggttgg cctggtatca gcagaaacca   120
gggaaagccc ctaagctcct aatctataag gcgtctaatt tagaaagtgg ggtcccatca   180
aggttcagcg gcagtggatc tgggacagaa ttcactctca ccatcagcag cctgcagcct   240
gatgattttg caacttatta ctgccaacag tataatagtt attcgtacac ttttggccag   300
gggaccaagc tggagatcaa a                                             321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagagtatta gtagctgg                                              18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Ser Ile Ser Ser Trp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 aaggcgtct                                                         9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Lys Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
caacagtata atagttattc gtacact            27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Gln Gln Tyr Asn Ser Tyr Ser Tyr Thr
1               5

<210> SEQ ID NO 145
<211> LENGTH: 348
<212> TYPE: DNA
<213> ORGANISM: Artificial Sequence
<220> FEATURE:
<223> OTHER INFORMATION: Synthetic

<400> SEQUENCE: 145
gaggtgcagc tgttggcgtc tgggggaggc ttggtacagc ctgggggtc cctgagactc      60 tcctgtgcag cctctggatt cacctttagt agctttgcca tgagctgggt ccgccaggct    120
ccagggaagg ggctggagtg ggtctcaggt attagtggta gtggtgttag cacatactac    180
gcagactccg tgaagggccg gttcaccatc tccagagaca attccaagaa cacgctgtat    240
ctgcaaatga acagcctgag agccgaggac acggccgcat attattgtgc gaaagaggcc    300
tataaatggc agccctgggg ccagggaacc ctggtcaccg tctcctca                 348

<210> SEQ ID NO 146
<211> LENGTH: 116
<212> TYPE: PRT
<213> ORGANISM: Artificial Sequence
<220> FEATURE:
<223> OTHER INFORMATION: Synthetic

<400> SEQUENCE: 146

Glu Val Gln Leu Leu Ala Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Val Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ala Tyr Lys Trp Gln Pro Trp Gly Gln Gly Thr Leu Val
            100                 105                 110

Thr Val Ser Ser
        115

<210> SEQ ID NO 147
<211> LENGTH: 24

```
<212> TYPE: DNA
<213> ORGANISM: Artificial Sequence
<220> FEATURE:
<223> OTHER INFORMATION: Synthetic

<400> SEQUENCE: 147
ggattcacct ttagtagctt tgcc                                          24

<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Thr Phe Ser Ser Phe Ala
1               5

<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149
attagtggta gtggtgttag caca                                          24

<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Gly Ser Gly Val Ser Thr
1               5

<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151
gcgaaagagg cctataaatg gcagccc                                       27

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Ala Lys Glu Ala Tyr Lys Trp Gln Pro
1               5

<210> SEQ ID NO 153
<211> LENGTH: 321
<212> TYPE: DNA
<213> ORGANISM: Artificial Sequence
<220> FEATURE:
<223> OTHER INFORMATION: Synthetic
```

<400> SEQUENCE: 153

```
gacatccaga tgacccagtc tccttccacc ctgtctgcat ctgtgggaga cagagtcacc     60
atcacttgcc gggccagtca gagtattagt agctggttgg cctggtatca gcagaaacca    120
gggaaagccc ctaagctcct aatctataag gcgtctaatt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtacac ttttggccag    300
gggaccaagc tggagatcaa a                                              321
```

<210> SEQ ID NO 154
<211> LENGTH: 107
<212> TYPE: PRT
<213> ORGANISM: Artificial Sequence
<220> FEATURE:
<223> OTHER INFORMATION: Synthetic

<400> SEQUENCE: 154

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: Synthetic

<400> SEQUENCE: 155

```
cagagtatta gtagctgg                                                   18
```

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

```
Gln Ser Ile Ser Ser Trp
1               5
```

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 aaggcgtct                                                                                          9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Lys Ala Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caacagtata atagttattc gtacact                                                                     27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

Gln Gln Tyr Asn Ser Tyr Ser Tyr Thr
1               5

<210> SEQ ID NO 161
<211> LENGTH: 363
<212> TYPE: DNA
<213> ORGANISM: Artificial Sequence
<220> FEATURE:
<223> OTHER INFORMATION: Synthetic

<400> SEQUENCE: 161
gaggtgcagc tgttggagtc tgggggggtc ttggtacagc ctgggggggtc cctgagactc           60 tcctgtgcag cctctggatt caattttaac aactatgaca tgagctgggt ccgccaggct          120
ccagggaagg ggctggagtg ggtctcagtc attagtgcaa gtggtcgtaa cacatactac          180
gcagactccg tgaagggccg gttcaccatc tccagagaca attccaagat cagtctgtat          240
ctgcaaatga acagcctgag acccgaggac acggccgtat attactgtgc gaaagatcac          300
ctcgtccact actactacgg tatggacgtc tggggccaag ggaccacggt caccgtctcc          360
tct                                                                        363

<210> SEQ ID NO 162
<211> LENGTH: 121
<212> TYPE: PRT
<213> ORGANISM: Artificial Sequence
<220> FEATURE:
<223> OTHER INFORMATION: Synthetic

<400> SEQUENCE: 162

Glu Val Gln Leu Leu Glu Ser Gly Gly Val Leu Val Gln Pro Gly Gly
1               5                   10                  15

Ser Leu Arg Leu Ser Cys Ala Ala Ser Gly Phe Asn Phe Asn Asn Tyr
            20                  25                  30

Asp Met Ser Trp Val Arg Gln Ala Pro Gly Lys Gly Leu Glu Trp Val
        35                  40                  45

Ser Val Ile Ser Ala Ser Gly Arg Asn Thr Tyr Tyr Ala Asp Ser Val
    50                  55                  60

Lys Gly Arg Phe Thr Ile Ser Arg Asp Asn Ser Lys Ile Ser Leu Tyr
65                  70                  75                  80

Leu Gln Met Asn Ser Leu Arg Pro Glu Asp Thr Ala Val Tyr Tyr Cys
                85                  90                  95

Ala Lys Asp His Leu Val His Tyr Tyr Tyr Gly Met Asp Val Trp Gly
            100                 105                 110

Gln Gly Thr Thr Val Thr Val Ser Ser
        115                 120

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggattcaatt ttaacaacta tgac                                          24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Phe Asn Phe Asn Asn Tyr Asp
1               5

<210> SEQ ID NO 165
<211> LENGTH: 24
<212> TYPE: DNA
<213> ORGANISM: Artificial Sequence
<220> FEATURE:
<223> OTHER INFORMATION: Synthetic

<400> SEQUENCE: 165
attagtgcaa gtggtcgtaa caca                                          24

<210> SEQ ID NO 166
<211> LENGTH: 8
<212> TYPE: PRT
<213> ORGANISM: Artificial Sequence
<220> FEATURE:
<223> OTHER INFORMATION: Synthetic

<400> SEQUENCE: 166

Ile Ser Ala Ser Gly Arg Asn Thr
1               5

<210> SEQ ID NO 167
<211> LENGTH: 42
<212> TYPE: DNA
<213> ORGANISM: Artificial Sequence
<220> FEATURE:
<223> OTHER INFORMATION: Synthetic

<400> SEQUENCE: 167

```
gcgaaagatc acctcgtcca ctactactac ggtatggacg tc                         42
```

<210> SEQ ID NO 168
<211> LENGTH: 14
<212> TYPE: PRT
<213> ORGANISM: Artificial Sequence
<220> FEATURE:
<223> OTHER INFORMATION: Synthetic

<400> SEQUENCE: 168

```
Ala Lys Asp His Leu Val His Tyr Tyr Tyr Gly Met Asp Val
1               5                   10
```

<210> SEQ ID NO 169
<211> LENGTH: 336
<212> TYPE: DNA
<213> ORGANISM: Artificial Sequence
<220> FEATURE:
<223> OTHER INFORMATION: Synthetic

<400> SEQUENCE: 169

```
gatattatga tgactcagtc tccactctcc ctgtccgtca cccctggaga gccggcctcc      60
atctcctgca ggtctagtca gagcctcctg catagtaatg gatacaacta tttggattgg    120
tacctccaga agtcaggaca gtctccacac ctcctgatct atttgggttc aatcgggcc     180 tccggggtcc ctgacaggtt cagtggcagt ggatcaggca cagattttac actgaaaatc    240
agcagagtgg aggctgagga tgtgggggtt tattactgca tgcaagctct acaaactcct    300
cggacgttcg gccaagggac caaggtggaa atcaaa                              336
```

<210> SEQ ID NO 170
<211> LENGTH: 112
<212> TYPE: PRT
<213> ORGANISM: Artificial Sequence
<220> FEATURE:
<223> OTHER INFORMATION: Synthetic

<400> SEQUENCE: 170

```
Asp Ile Met Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Ser Gly Gln Ser
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Gly Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110
```

<210> SEQ ID NO 171
<211> LENGTH: 33
<212> TYPE: DNA
<213> ORGANISM: Artificial Sequence
<220> FEATURE:
<223> OTHER INFORMATION: Synthetic

<400> SEQUENCE: 171

```
cagagcctcc tgcatagtaa tggatacaac tat                                    33
```

<210> SEQ ID NO 172
<211> LENGTH: 11
<212> TYPE: PRT
<213> ORGANISM: Artificial Sequence
<220> FEATURE:
<223> OTHER INFORMATION: Synthetic

<400> SEQUENCE: 172

```
Gln Ser Leu Leu His Ser Asn Gly Tyr Asn Tyr
1               5                   10
```

<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

```
ttgggttct                                                                9
```

<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

```
Leu Gly Ser
1
```

<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175

```
atgcaagctc tacaaactcc tcggacg                                           27
```

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

```
Met Gln Ala Leu Gln Thr Pro Arg Thr
1               5
```

<210> SEQ ID NO 177
<211> LENGTH: 363
<212> TYPE: DNA
<213> ORGANISM: Artificial Sequence
<220> FEATURE:
<223> OTHER INFORMATION: Synthetic

<400> SEQUENCE: 177

```
gaggaccgag tgttggaatc tggggaggc ttggtacagc ctgggggtc cctgagactc         60 tcctgtgcag cctctggatt catgtttagc agctatgcca tgagctgggt ccgccaggct      120
```
ccagggaagg ggctggagtg ggtctcactt attagtggtc gtgacggtaa cacatactat    180
gcagactccg tgaagggccg gttcaccatc tccagagaca attccaggaa cacgctctat    240
ctacaattga acagcctgcg agccgaggac acggccgtat attactgtgc gaaagataca    300
gctgtggttc ctggctacgg tatggacgtc tggggccaag gaccacggt caccgtctcc    360 tca                                                                  363

```
<210> SEQ ID NO 178
<211> LENGTH: 121
<212> TYPE: PRT
<213> ORGANISM: Artificial Sequence
<220> FEATURE:
<223> OTHER INFORMATION: Synthetic

<400> SEQUENCE: 178
```

Glu Asp Arg Val Leu Glu Ser Gly Gly Gly Leu Val Gln Pro Gly Gly
1               5                   10                  15

Ser Leu Arg Leu Ser Cys Ala Ala Ser Gly Phe Met Phe Ser Ser Tyr
            20                  25                  30

Ala Met Ser Trp Val Arg Gln Ala Pro Gly Lys Gly Leu Glu Trp Val
        35                  40                  45

Ser Leu Ile Ser Gly Arg Asp Gly Asn Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Leu Asn Ser Leu Arg Ala Glu Asp Thr Ala Val Tyr Tyr Cys
                85                  90                  95

Ala Lys Asp Thr Ala Val Val Pro Gly Tyr Gly Met Asp Val Trp Gly
            100                 105                 110

Gln Gly Thr Thr Val Thr Val Ser Ser
        115                 120

```
<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179
```
ggattcatgt ttagcagcta tgcc                                            24

```
<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180
```

Gly Phe Met Phe Ser Ser Tyr Ala
1               5

```
<210> SEQ ID NO 181
<211> LENGTH: 24
<212> TYPE: DNA
<213> ORGANISM: Artificial Sequence
<220> FEATURE:
<223> OTHER INFORMATION: Synthetic

<400> SEQUENCE: 181
```

```
attagtggtc gtgacggtaa caca                                                24
```

<210> SEQ ID NO 182
<211> LENGTH: 8
<212> TYPE: PRT
<213> ORGANISM: Artificial Sequence
<220> FEATURE:
<223> OTHER INFORMATION: Synthetic

<400> SEQUENCE: 182

Ile Ser Gly Arg Asp Gly Asn Thr
1               5

<210> SEQ ID NO 183
<211> LENGTH: 42
<212> TYPE: DNA
<213> ORGANISM: Artificial Sequence
<220> FEATURE:
<223> OTHER INFORMATION: Synthetic

<400> SEQUENCE: 183

```
gcgaaagata cagctgtggt tcctggctac ggtatggacg tc                            42
```

<210> SEQ ID NO 184
<211> LENGTH: 14
<212> TYPE: PRT
<213> ORGANISM: Artificial Sequence
<220> FEATURE:
<223> OTHER INFORMATION: Synthetic

<400> SEQUENCE: 184

Ala Lys Asp Thr Ala Val Val Pro Gly Tyr Gly Met Asp Val
1               5                   10

<210> SEQ ID NO 185
<211> LENGTH: 321
<212> TYPE: DNA
<213> ORGANISM: Artificial Sequence
<220> FEATURE:
<223> OTHER INFORMATION: Synthetic

<400> SEQUENCE: 185

```
gacatccaga tgacccagtc tccttccacc ctgtctgcat ctgtaggaga cagagtcacc         60
atcacttgcc gggccagtca gagtattagt aactggttgg cctggtatca gcagagacca        120
gggaaagccc ctaagctcct gatctataag gcgtctagtt tagaaagtgg ggtcccatca        180
aggttcagcg gcagtggatc tgggacagaa ttcactctca ccatcagcag cctgcagcct        240
gatgattttg caagttatta ctgccaacag tataatagtt attcgtggac gttcggccaa        300
gggaccaagg tggaaatcaa a                                                  321
```

<210> SEQ ID NO 186
<211> LENGTH: 107
<212> TYPE: PRT
<213> ORGANISM: Artificial Sequence
<220> FEATURE:
<223> OTHER INFORMATION: Synthetic

<400> SEQUENCE: 186

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Asn Trp
            20                  25                  30

-continued

```
Leu Ala Trp Tyr Gln Gln Arg Pro Gly Lys Ala Pro Lys Leu Leu Ile
            35                  40                  45

Tyr Lys Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Ser Tyr Tyr Cys Gln Gln Tyr Asn Ser Tyr Ser Trp
                 85                  90                  95

Thr Phe Gly Gln Gly Thr Lys Val Glu Ile Lys
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187
cagagtatta gtaactgg                                                   18

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

Gln Ser Ile Ser Asn Trp
1               5

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189 aaggcgtct                                                              9

<210> SEQ ID NO 190
<211> LENGTH: 3
<212> TYPE: PRT
<213> ORGANISM: Artificial Sequence
<220> FEATURE:
<223> OTHER INFORMATION: Synthetic

<400> SEQUENCE: 190

Lys Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
caacagtata atagttattc gtggacg                                         27

<210> SEQ ID NO 192

<211> LENGTH: 9
<212> TYPE: PRT
<213> ORGANISM: Artificial Sequence
<220> FEATURE:
<223> OTHER INFORMATION: Synthetic

<400> SEQUENCE: 192

Gln Gln Tyr Asn Ser Tyr Ser Trp Thr
1               5

<210> SEQ ID NO 193
<211> LENGTH: 348
<212> TYPE: DNA
<213> ORGANISM: Artificial Sequence
<220> FEATURE:
<223> OTHER INFORMATION: Synthetic

<400> SEQUENCE: 193

```
gaggtgcagc tgttggcgtc tgggggaggc ttggtacagc ctgggggtc cctgagactc      60 tcctgtgcag cctctggatt cacctttagc agctttgcca tgagctgggt ccgccaggct    120
ccagggaagg ggctggagtg ggtctcaggt attagtggta gtggtggtag cacatactac    180
gcagactccg tgaagggccg gttcaccatc tccagagaca attccaaaaa cacgctgtat    240
ctgcaaatga acagcctgag agccgaggac acggccgcat attactgtgc gaaagaggcc    300
tataaatggc agccctgggg ccagggaatc cgggtcaccg tctcctca                 348
```

<210> SEQ ID NO 194
<211> LENGTH: 116
<212> TYPE: PRT
<213> ORGANISM: Artificial Sequence
<220> FEATURE:
<223> OTHER INFORMATION: Synthetic

<400> SEQUENCE: 194

Glu Val Gln Leu Leu Ala Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ala Tyr Tyr Cys
                85                  90                  95

Ala Lys Glu Ala Tyr Lys Trp Gln Pro Trp Gly Gln Gly Ile Arg Val
            100                 105                 110

Thr Val Ser Ser
        115

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggattcacct ttagcagctt tgcc      24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Ser Ser Phe Ala
1               5

<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197
attagtggta gtggtggtag caca                                         24

<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Gly Ser Gly Gly Ser Thr
1               5

<210> SEQ ID NO 199
<211> LENGTH: 27
<212> TYPE: DNA
<213> ORGANISM: Artificial Sequence
<220> FEATURE:
<223> OTHER INFORMATION: Synthetic

<400> SEQUENCE: 199
gcgaaagagg cctataaatg gcagccc                                      27

<210> SEQ ID NO 200
<211> LENGTH: 9
<212> TYPE: PRT
<213> ORGANISM: Artificial Sequence
<220> FEATURE:
<223> OTHER INFORMATION: Synthetic

<400> SEQUENCE: 200

Ala Lys Glu Ala Tyr Lys Trp Gln Pro
1               5

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccttccacc ctgtctgcat ctgtgggaga cagagtctcc    60
atcacttgcc gggccagtca gagtattagt agctggttgg cctggtatca gcagaaacca   120
gggaaagccc ctaagctcct gatctataag gcgtctaatt tagacagtgg ggtcccatca   180
aggttcagcg gcagtggatc tgggacagat ttcactctca ccatcagcag cctgcagcct    240
gatgattttg caacttatta ctgccaacag tataatagtt attcgtacac ttttggccag    300
gggaccaagc tggagatcaa a    321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Thr Leu Ser Ala Ser Val Gly
1               5                   10                  15

Asp Arg Val Ser Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatta gtagctgg    18

<210> SEQ ID NO 204
<211> LENGTH: 6
<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Trp
1               5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggcgtct    9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ala Ser
1

<210> SEQ ID NO 207
<211> LENGTH: 27
<212> TYPE: DNA
<213> ORGANISM: Artificial Sequence
<220> FEATURE:
<223> OTHER INFORMATION: Synthetic

<400> SEQUENCE: 207
caacagtata atagttattc gtacact                                        27

<210> SEQ ID NO 208
<211> LENGTH: 9
<212> TYPE: PRT
<213> ORGANISM: Artificial Sequence
<220> FEATURE:
<223> OTHER INFORMATION: Synthetic

<400> SEQUENCE: 208

Gln Gln Tyr Asn Ser Tyr Ser Tyr Thr
1               5

<210> SEQ ID NO 209
<211> LENGTH: 387
<212> TYPE: DNA
<213> ORGANISM: Artificial Sequence
<220> FEATURE:
<223> OTHER INFORMATION: Synthetic

<400> SEQUENCE: 209
gaggtgcagc tgttggagtc tgggggaggc ttggtacagc cggggggtc  cctgagactc      60 tcctgtgcag cctctggatt caccttaga aactatgcca tgagctgggt ccgccaggct     120
ccaggaaagg ggctggagtg ggtctcagct attaatggtg gtggtgatag cacatactac    180
gcagactccg tgaagggccg gttcaccatc tccagagaca attccaagaa tacgctgtat    240
ctgcaaatga acagcctgag agccgaggac acggccgtat attactgtgc gaaagaggag    300
ggagactgga actacgtggg atatggttac tactactact acggtatgga cgtctggggc    360
caagggacca cggtcaccgt ctcctca                                        387

<210> SEQ ID NO 210
<211> LENGTH: 129
<212> TYPE: PRT
<213> ORGANISM: Artificial Sequence
<220> FEATURE:
<223> OTHER INFORMATION: Synthetic

<400> SEQUENCE: 210

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met Ser Trp Val Arg Gln Ala Pro Gly Lys Gly Leu Glu Trp Val
        35                  40                  45

Ser Ala Ile Asn Gly Gly Gly Asp Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Glu Gly Asp Trp Asn Tyr Val Gly Tyr Gly Tyr Tyr Tyr
            100                 105                 110

Tyr Tyr Gly Met Asp Val Trp Gly Gln Gly Thr Thr Val Thr Val Ser
        115                 120                 125

Ser

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct ttagaaacta tgcc                                              24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Arg Asn Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attaatggtg gtggtgatag caca                                              24

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Ile Asn Gly Gly Gly Asp Ser Thr
1               5

<210> SEQ ID NO 215
<211> LENGTH: 66
<212> TYPE: DNA
<213> ORGANISM: Artificial Sequence
<220> FEATURE:
<223> OTHER INFORMATION: Synthetic

<400> SEQUENCE: 215
gcgaaagagg agggagactg gaactacgtg ggatatggtt actactacta ctacggtatg       60
gacgtc                                                                  66
```

```
<210> SEQ ID NO 216
<211> LENGTH: 22
<212> TYPE: PRT
<213> ORGANISM: Artificial Sequence
<220> FEATURE:
<223> OTHER INFORMATION: Synthetic

<400> SEQUENCE: 216

Ala Lys Glu Glu Gly Asp Trp Asn Tyr Val Gly Tyr Gly Tyr Tyr Tyr
1               5                   10                  15

Tyr Tyr Gly Met Asp Val
            20

<210> SEQ ID NO 217
<211> LENGTH: 321
<212> TYPE: DNA
<213> ORGANISM: Artificial Sequence
<220> FEATURE:
<223> OTHER INFORMATION: Synthetic

<400> SEQUENCE: 217
gacatccaga tgacccagtc tccatcttcc atgtctgcat ctgtaggaga cagagtcacc      60
atcacttgtc gggcgagtca gggtattagc agctggttag cctggtatca gcagaaacca    120
gggaaagccc ctaagctcct gatctatgct gcatccagtt tgcaaagtgg ggtcccatca    180
aggttcagcg gcagtggatc tgggacagat ttcactctca ccatcaggag cctgcagcct    240
gaagattttg caacttacta ttgtcaacag gctaacagtt tcccgtacac ttttggccag    300
gggaccaagc tggagatcaa a                                              321

<210> SEQ ID NO 218
<211> LENGTH: 107
<212> TYPE: PRT
<213> ORGANISM: Artificial Sequence
<220> FEATURE:
<223> OTHER INFORMATION: Synthetic

<400> SEQUENCE: 218

Asp Ile Gln Met Thr Gln Ser Pro Ser Ser Met Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219
cagggtatta gcagctgg                                                   18
```

<210> SEQ ID NO 220
<211> LENGTH: 6
<212> TYPE: PRT
<213> ORGANISM: Artificial Sequence
<220> FEATURE:
<223> OTHER INFORMATION: Synthetic

<400> SEQUENCE: 220

Gln Gly Ile Ser Ser Trp
1               5

<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221 gctgcatcc                                                                 9

<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Ala Ala Ser
1

<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223
caacaggcta acagtttccc gtacact                                            27

<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Gln Ala Asn Ser Phe Pro Tyr Thr
1               5

<210> SEQ ID NO 225
<211> LENGTH: 369
<212> TYPE: DNA
<213> ORGANISM: Artificial Sequence
<220> FEATURE:
<223> OTHER INFORMATION: Synthetic

<400> SEQUENCE: 225
caggtgcagc tggtggagtc tgggggaggc gtggtccagc ctggagggtc cctgagactc        60
tcctgtgaag cctctggttt caccttcgga agctatggca tgcactgggt ccgccaggct       120
ccaggcaagg ggctggagtg gatggcagtt atatcatatg atggaaatag tagatactct       180

```
gcagactccg tgaagggccg attcaccatc tccagagaca attccaagaa tacgctgtat    240
ctgcagatga acagcctgag agctgaggac acggctctgt attactgtgc gaaagaaaat    300
catatagcag ctcgtcgtcc cggaggtctg acgtctggg gccaagggac cacggtcacc    360
gtctcctca                                                             369
```

<210> SEQ ID NO 226
<211> LENGTH: 123
<212> TYPE: PRT
<213> ORGANISM: Artificial Sequence
<220> FEATURE:
<223> OTHER INFORMATION: Synthetic

<400> SEQUENCE: 226

```
Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Gly Ser Tyr
            20                  25                  30

Gly Met His Trp Val Arg Gln Ala Pro Gly Lys Gly Leu Glu Trp Met
        35                  40                  45

Ala Val Ile Ser Tyr Asp Gly Asn Ser Arg Tyr Ser Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Glu Asn His Ile Ala Ala Arg Arg Pro Gly Gly Leu Asp Val
            100                 105                 110

Trp Gly Gln Gly Thr Thr Val Thr Val Ser Ser
        115                 120
```

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227

```
ggtttcacct tcggaagcta tggc                                            24
```

<210> SEQ ID NO 228
<211> LENGTH: 8
<212> TYPE: PRT
<213> ORGANISM: Artificial Sequence
<220> FEATURE:
<223> OTHER INFORMATION: Synthetic

<400> SEQUENCE: 228

```
Gly Phe Thr Phe Gly Ser Tyr Gly
1               5
```

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229

```
atatcatatg atggaaatag taga                                            24
```

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Tyr Asp Gly Asn Ser Arg
1               5

<210> SEQ ID NO 231
<211> LENGTH: 48
<212> TYPE: DNA
<213> ORGANISM: Artificial Sequence
<220> FEATURE:
<223> OTHER INFORMATION: Synthetic

<400> SEQUENCE: 231
gcgaaagaaa atcatatagc agctcgtcgt cccggaggtc tggacgtc                    48

<210> SEQ ID NO 232
<211> LENGTH: 16
<212> TYPE: PRT
<213> ORGANISM: Artificial Sequence
<220> FEATURE:
<223> OTHER INFORMATION: Synthetic

<400> SEQUENCE: 232

Ala Lys Glu Asn His Ile Ala Ala Arg Arg Pro Gly Gly Leu Asp Val
1               5                   10                  15

<210> SEQ ID NO 233
<211> LENGTH: 321
<212> TYPE: DNA
<213> ORGANISM: Artificial Sequence
<220> FEATURE:
<223> OTHER INFORMATION: Synthetic

<400> SEQUENCE: 233
gacatccaga tgacccagtc tccatcctcc ctgtctgcat ctgtaggaga cagagtcacc        60
atcacttgcc gggcgagtca gggcattagc atttatttag cctggtatca acagaaacca      120
gggaaagttc ctaagctcct gatctatgct gcatccagtt tgcaatcagg ggtcccatct      180
cggttcagtg gcagtggatc tgggacagat ttcactctca ccatcagcag cctgcagcct      240
gaagatgttg caacttattt ctgtcaaaac tataacattg ccccgtggac gctcggccaa      300
gggaccaagg tggaaatcaa a                                                 321

<210> SEQ ID NO 234
<211> LENGTH: 107
<212> TYPE: PRT
<213> ORGANISM: Artificial Sequence
<220> FEATURE:
<223> OTHER INFORMATION: Synthetic

<400> SEQUENCE: 234

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ile Tyr
            20                  25                  30

Leu Ala Trp Tyr Gln Gln Lys Pro Gly Lys Val Pro Lys Leu Leu Ile
        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                  70                  75                  80

Glu Asp Val Ala Thr Tyr Phe Cys Gln Asn Tyr Asn Ile Ala Pro Trp
                 85                  90                  95

Thr Leu Gly Gln Gly Thr Lys Val Glu Ile Lys
            100                 105

<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235
cagggcatta gcatttat                                           18

<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Gly Ile Ser Ile Tyr
 1               5

<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237 gctgcatcc                                                      9

<210> SEQ ID NO 238
<211> LENGTH: 3
<212> TYPE: PRT
<213> ORGANISM: Artificial Sequence
<220> FEATURE:
<223> OTHER INFORMATION: Synthetic

<400> SEQUENCE: 238

Ala Ala Ser
 1

<210> SEQ ID NO 239
<211> LENGTH: 24
<212> TYPE: DNA
<213> ORGANISM: Artificial Sequence
<220> FEATURE:
<223> OTHER INFORMATION: Synthetic

<400> SEQUENCE: 239
caaaactata acattgcccc gtgg                                    24

<210> SEQ ID NO 240
<211> LENGTH: 8
<212> TYPE: PRT

<213> ORGANISM: Artificial Sequence
<220> FEATURE:
<223> OTHER INFORMATION: Synthetic

<400> SEQUENCE: 240

Gln Asn Tyr Asn Ile Ala Pro Trp
1               5

<210> SEQ ID NO 241
<211> LENGTH: 384
<212> TYPE: DNA
<213> ORGANISM: Artificial Sequence
<220> FEATURE:
<223> OTHER INFORMATION: Synthetic

<400> SEQUENCE: 241
gaggtgcagc tgttggagtc tgggggaggc ttggtgcagc ctggggggtc cctgagactc      60
tcctgtgcag cctctggatt catctttacc aattatgcca tgacctggct ccgccaggct     120
ccagggaagg gctggagtg gtctcagct cttagtggtt ctggtggtac cacatactac       180
gcagactccg tgaagggccg gttcaccacc tccagagaca attccaagaa cactctgtat     240
ctgcaaatga acagcctgag agccgaggac acggccgtct attactgtgc gaaagatccc     300
cattactatg gtcggggaa tgattacttc tactactacg gtttggacgt ctggggccga     360
gggaccacgg tcaccgtctc ctca                                            384

<210> SEQ ID NO 242
<211> LENGTH: 128
<212> TYPE: PRT
<213> ORGANISM: Artificial Sequence
<220> FEATURE:
<223> OTHER INFORMATION: Synthetic

<400> SEQUENCE: 242

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Thr Asn Tyr
            20                  25                  30

Ala Met Thr Trp Leu Arg Gln Ala Pro Gly Lys Gly Leu Glu Trp Val
        35                  40                  45

Ser Ala Leu Ser Gly Ser Gly Gly Thr Thr Tyr Tyr Ala Asp Ser Val
    50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro His Tyr Tyr Gly Ser Gly Asn Asp Tyr Phe Tyr Tyr
            100                 105                 110

Tyr Gly Leu Asp Val Trp Gly Arg Gly Thr Thr Val Thr Val Ser Ser
        115                 120                 125

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcatct ttaccaatta tgcc                                            24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Ile Phe Thr Asn Tyr Ala
1               5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
cttagtggtt ctggtggtac caca                                           24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Leu Ser Gly Ser Gly Gly Thr Thr
1               5

<210> SEQ ID NO 247
<211> LENGTH: 63
<212> TYPE: DNA
<213> ORGANISM: Artificial Sequence
<220> FEATURE:
<223> OTHER INFORMATION: Synthetic

<400> SEQUENCE: 247
gcgaaagatc cccattacta tgggtcgggg aatgattact tctactacta cggtttggac    60
gtc                                                                  63

<210> SEQ ID NO 248
<211> LENGTH: 21
<212> TYPE: PRT
<213> ORGANISM: Artificial Sequence
<220> FEATURE:
<223> OTHER INFORMATION: Synthetic

<400> SEQUENCE: 248

Ala Lys Asp Pro His Tyr Tyr Gly Ser Gly Asn Asp Tyr Phe Tyr Tyr
1               5                   10                  15

Tyr Gly Leu Asp Val
            20

<210> SEQ ID NO 249
<211> LENGTH: 336
<212> TYPE: DNA
<213> ORGANISM: Artificial Sequence
<220> FEATURE:
<223> OTHER INFORMATION: Synthetic

<400> SEQUENCE: 249
gatattgtga tgactcagtc tccactctcc ctgcccgtca cccctggaga gccggcctcc    60

```
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaggctct acaaactccg    300
tacacttttg gccaggggac caagctggag atcaaa                              336
```

```
<210> SEQ ID NO 250
<211> LENGTH: 112
<212> TYPE: PRT
<213> ORGANISM: Artificial Sequence
<220> FEATURE:
<223> OTHER INFORMATION: Synthetic

<400> SEQUENCE: 250

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

```
<210> SEQ ID NO 251
<211> LENGTH: 33
<212> TYPE: DNA
<213> ORGANISM: Artificial Sequence
<220> FEATURE:
<223> OTHER INFORMATION: Synthetic

<400> SEQUENCE: 251
cagagcctcc tgcatagtaa tggatacaac tat                                 33
```

```
<210> SEQ ID NO 252
<211> LENGTH: 11
<212> TYPE: PRT
<213> ORGANISM: Artificial Sequence
<220> FEATURE:
<223> OTHER INFORMATION: Synthetic

<400> SEQUENCE: 252

Gln Ser Leu Leu His Ser Asn Gly Tyr Asn Tyr
1               5                   10
```

```
<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 ttgggttct                                                            9
```

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Leu Gly Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
atgcaggctc tacaaactcc gtacact                                         27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Ala Leu Gln Thr Pro Tyr Thr
1               5

<210> SEQ ID NO 257
<211> LENGTH: 357
<212> TYPE: DNA
<213> ORGANISM: Artificial Sequence
<220> FEATURE:
<223> OTHER INFORMATION: Synthetic

<400> SEQUENCE: 257
gaggtgcagc tggtggagtc tgggggaggt ttggtccagt ctgggggtc cctgagactc      60 tcttgtgcag cctctggatt cacctttagt agatattgga tgagctgggt ccgccaggct    120
ccagggaagg ggctggagtg ggtggccaac ataaaacaag atggaagtga aaagattat     180 gtggactctg tgaagggccg attcaccatt tccagagaca acaccaagag ctcactgttt    240
ctgcaaatga atagcctgag agccgaggac acggctgtgt attactgtgc gaaggagaga    300
tggaactgga acttctttga ctactggggc cagggaaccc tggtcactgt ctcctca      357

<210> SEQ ID NO 258
<211> LENGTH: 119
<212> TYPE: PRT
<213> ORGANISM: Artificial Sequence
<220> FEATURE:
<223> OTHER INFORMATION: Synthetic

<400> SEQUENCE: 258

Glu Val Gln Leu Val Glu Ser Gly Gly Gly Leu Val Gln Ser Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

```
Ala Asn Ile Lys Gln Asp Gly Ser Glu Lys Asp Tyr Val Asp Ser Val
    50                  55                  60

Lys Gly Arg Phe Thr Ile Ser Arg Asp Asn Lys Ser Ser Leu Phe
65                  70                  75                  80

Leu Gln Met Asn Ser Leu Arg Ala Glu Asp Thr Ala Val Tyr Tyr Cys
                85                  90                  95

Ala Lys Glu Arg Trp Asn Trp Asn Phe Phe Asp Tyr Trp Gly Gln Gly
            100                 105                 110

Thr Leu Val Thr Val Ser Ser
            115
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
ggattcacct ttagtagata ttgg              24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

Gly Phe Thr Phe Ser Arg Tyr Trp
1               5

<210> SEQ ID NO 261
<211> LENGTH: 24
<212> TYPE: DNA
<213> ORGANISM: Artificial Sequence
<220> FEATURE:
<223> OTHER INFORMATION: Synthetic

<400> SEQUENCE: 261
ataaaacaag atggaagtga gaaa              24

<210> SEQ ID NO 262
<211> LENGTH: 8
<212> TYPE: PRT
<213> ORGANISM: Artificial Sequence
<220> FEATURE:
<223> OTHER INFORMATION: Synthetic

<400> SEQUENCE: 262

Ile Lys Gln Asp Gly Ser Glu Lys
1               5

<210> SEQ ID NO 263
<211> LENGTH: 36
<212> TYPE: DNA
<213> ORGANISM: Artificial Sequence
<220> FEATURE:
<223> OTHER INFORMATION: Synthetic

<400> SEQUENCE: 263
gcgaaggaga gatggaactg gaacttcttt gactac              36

<210> SEQ ID NO 264

<211> LENGTH: 12
<212> TYPE: PRT
<213> ORGANISM: Artificial Sequence
<220> FEATURE:
<223> OTHER INFORMATION: Synthetic

<400> SEQUENCE: 264

Ala Lys Glu Arg Trp Asn Trp Asn Phe Phe Asp Tyr
1               5                   10

<210> SEQ ID NO 265
<211> LENGTH: 318
<212> TYPE: DNA
<213> ORGANISM: Artificial Sequence
<220> FEATURE:
<223> OTHER INFORMATION: Synthetic

<400> SEQUENCE: 265
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcatctagtt tagaaagtgg ggtcccatca    180
aggttcagcg gcagtggatc tgggacagaa ttcactctca ccatcagcag cctgcagcct    240
gatgattttg caacttatta ctgccagcag tttaatagtt attccacttt tggccagggg    300
accaagctgg agatcaaa                                                   318

<210> SEQ ID NO 266
<211> LENGTH: 106
<212> TYPE: PRT
<213> ORGANISM: Artificial Sequence
<220> FEATURE:
<223> OTHER INFORMATION: Synthetic

<400> SEQUENCE: 266

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Asn Ser Tyr Ser Thr
                85                  90                  95

Phe Gly Gln Gly Thr Lys Leu Glu Ile Lys
            100                 105

<210> SEQ ID NO 267
<211> LENGTH: 18
<212> TYPE: DNA
<213> ORGANISM: Artificial Sequence
<220> FEATURE:
<223> OTHER INFORMATION: Synthetic

<400> SEQUENCE: 267
cagagtatta gtagctgg                                                    18

<210> SEQ ID NO 268
<211> LENGTH: 6

```
<212> TYPE: PRT
<213> ORGANISM: Artificial Sequence
<220> FEATURE:
<223> OTHER INFORMATION: Synthetic

<400> SEQUENCE: 268

Gln Ser Ile Ser Ser Trp
1               5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 aaggcatct                                                            9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Lys Ala Ser
1

<210> SEQ ID NO 271
<211> LENGTH: 24
<212> TYPE: DNA
<213> ORGANISM: Artificial Sequence
<220> FEATURE:
<223> OTHER INFORMATION: Synthetic

<400> SEQUENCE: 271
cagcagttta atagttattc cact                                          24

<210> SEQ ID NO 272
<211> LENGTH: 8
<212> TYPE: PRT
<213> ORGANISM: Artificial Sequence
<220> FEATURE:
<223> OTHER INFORMATION: Synthetic

<400> SEQUENCE: 272

Gln Gln Phe Asn Ser Tyr Ser Thr
1               5

<210> SEQ ID NO 273
<211> LENGTH: 369
<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggagac ttaatacagc cggggggtc cctgagactc     60 tcctgtatag cctctggatt cacctttaga ggctatgcca tgagttgggt ccgccaggct  120
ccaggggagg ggctggactg ggtctcaggt attagttctg gtggcgggaa cacatattac  180
gcagactccg tgaagggccg gttcaccatc tccagagaca attccaagaa cacgctgtat  240
ttgcaaatga acagtctgag agtcgaggac acggccgtat attactgtgc gaaagacaga  300
```

```
ggggtgtaa gggactttta ctacggtttg gacgtctggg gccagggac cacggtcacc      360 gtctcctca                                                             369
```

<210> SEQ ID NO 274
<211> LENGTH: 123
<212> TYPE: PRT
<213> ORGANISM: Artificial Sequence
<220> FEATURE:
<223> OTHER INFORMATION: Synthetic

<400> SEQUENCE: 274

```
Glu Val Gln Leu Val Glu Ser Gly Gly Asp Leu Ile Gln Pro Gly Gly
1               5                   10                  15

Ser Leu Arg Leu Ser Cys Ile Ala Ser Gly Phe Thr Phe Arg Gly Tyr
            20                  25                  30

Ala Met Ser Trp Val Arg Gln Ala Pro Gly Glu Gly Leu Asp Trp Val
        35                  40                  45

Ser Gly Ile Ser Ser Gly Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Arg Gly Gly Val Arg Asp Phe Tyr Tyr Gly Leu Asp Val
            100                 105                 110

Trp Gly Gln Gly Thr Thr Val Thr Val Ser Ser
        115                 120
```

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275

```
ggattcacct ttagaggcta tgcc                                            24
```

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

```
Gly Phe Thr Phe Arg Gly Tyr Ala
1               5
```

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277

```
attagttctg gtggcgggaa caca                                            24
```

<210> SEQ ID NO 278
<211> LENGTH: 8

```
<212> TYPE: PRT
<213> ORGANISM: Artificial Sequence
<220> FEATURE:
<223> OTHER INFORMATION: Synthetic

<400> SEQUENCE: 278

Ile Ser Ser Gly Gly Gly Asn Thr
1               5

<210> SEQ ID NO 279
<211> LENGTH: 48
<212> TYPE: DNA
<213> ORGANISM: Artificial Sequence
<220> FEATURE:
<223> OTHER INFORMATION: Synthetic

<400> SEQUENCE: 279
gcgaaagaca gagggggtgt aagggacttt tactacggtt tggacgtc                48

<210> SEQ ID NO 280
<211> LENGTH: 16
<212> TYPE: PRT
<213> ORGANISM: Artificial Sequence
<220> FEATURE:
<223> OTHER INFORMATION: Synthetic

<400> SEQUENCE: 280

Ala Lys Asp Arg Gly Gly Val Arg Asp Phe Tyr Tyr Gly Leu Asp Val
1               5                   10                  15

<210> SEQ ID NO 281
<211> LENGTH: 321
<212> TYPE: DNA
<213> ORGANISM: Artificial Sequence
<220> FEATURE:
<223> OTHER INFORMATION: Synthetic

<400> SEQUENCE: 281
gacatccaga tgacccagtc tccttccacc ctgtctgcat ctgtaggaga cagagtcacc       60
atcacttgcc gggccagtca gagtatttat agttggttgg cctggtatca gcagaaacca      120
gggaaagccc ctaaactcct gatctataag gcgtctagtt tagaaagtgg ggtcccgtca      180
aggttcagcg gcagtggatc tgggacagat ttcactctca ccatcagcag cctgcagcct      240
gatgatttta caacttatta ctgccaacaa tatcttagtt attctcggac gttcggccaa      300
gggaccaagg tggaaatcaa a                                                321

<210> SEQ ID NO 282
<211> LENGTH: 107
<212> TYPE: PRT
<213> ORGANISM: Artificial Sequence
<220> FEATURE:
<223> OTHER INFORMATION: Synthetic

<400> SEQUENCE: 282

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Tyr Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Asp Asp Phe Thr Thr Tyr Tyr Cys Gln Gln Tyr Leu Ser Tyr Ser Arg
                 85                  90                  95

Thr Phe Gly Gln Gly Thr Lys Val Glu Ile Lys
            100                 105
```

<210> SEQ ID NO 283
<211> LENGTH: 18
<212> TYPE: DNA
<213> ORGANISM: Artificial Sequence
<220> FEATURE:
<223> OTHER INFORMATION: Synthetic

<400> SEQUENCE: 283
cagagtattt atagttgg                                                  18

<210> SEQ ID NO 284
<211> LENGTH: 6
<212> TYPE: PRT
<213> ORGANISM: Artificial Sequence
<220> FEATURE:
<223> OTHER INFORMATION: Synthetic

<400> SEQUENCE: 284

```
Gln Ser Ile Tyr Ser Trp
1               5
```

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 aaggcgtct                                                             9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

```
Lys Ala Ser
1
```

<210> SEQ ID NO 287
<211> LENGTH: 27
<212> TYPE: DNA
<213> ORGANISM: Artificial Sequence
<220> FEATURE:
<223> OTHER INFORMATION: Synthetic

<400> SEQUENCE: 287
caacaatatc ttagttattc tcggacg                                        27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Gln Gln Tyr Leu Ser Tyr Ser Arg Thr
1               5

<210> SEQ ID NO 289
<211> LENGTH: 378
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggcaggtc cctgagactc      60
tcctttgcag cctctggatt cacctttgat gattatgcca tgcactgggt ccggcaagct     120
ccagggaagg gcctggagtg gtctcaggt attagttgga atagtggtag cataggctat      180
gcggactctg tgaagggccg attcaccatc tccagagaca acgccaagaa ctccctgtat     240
ctgcaaatga acagtctgag agctgaggac acggccttgt attactgtgc aaaagcccgt     300
ggatacagct atggttacgg ggagtactac tacggtatgg acgtctgggg ccaagggacc     360
acggtcaccg tctcctca                                                   378

<210> SEQ ID NO 290
<211> LENGTH: 126
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Arg
1               5                   10                  15

Ser Leu Arg Leu Ser Phe Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Ala Arg Gly Tyr Ser Tyr Gly Tyr Gly Glu Tyr Tyr Tyr Gly
            100                 105                 110

Met Asp Val Trp Gly Gln Gly Thr Thr Val Thr Val Ser Ser
        115                 120                 125

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttgatgatta tgcc                                             24

<210> SEQ ID NO 292
<211> LENGTH: 8
<212> TYPE: PRT

```
<213> ORGANISM: Artificial Sequence
<220> FEATURE:
<223> OTHER INFORMATION: Synthetic

<400> SEQUENCE: 292

Gly Phe Thr Phe Asp Asp Tyr Ala
1               5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attagttgga atagtggtag cata                                          24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Ser Trp Asn Ser Gly Ser Ile
1               5

<210> SEQ ID NO 295
<211> LENGTH: 57
<212> TYPE: DNA
<213> ORGANISM: Artificial Sequence
<220> FEATURE:
<223> OTHER INFORMATION: Synthetic

<400> SEQUENCE: 295
gcaaaagccc gtggatacag ctatggttac ggggagtact actacggtat ggacgtc      57

<210> SEQ ID NO 296
<211> LENGTH: 19
<212> TYPE: PRT
<213> ORGANISM: Artificial Sequence
<220> FEATURE:
<223> OTHER INFORMATION: Synthetic

<400> SEQUENCE: 296

Ala Lys Ala Arg Gly Tyr Ser Tyr Gly Tyr Gly Glu Tyr Tyr Tyr Gly
1               5                   10                  15

Met Asp Val

<210> SEQ ID NO 297
<211> LENGTH: 321
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcctcc ctgtctgcat ctgtaggaga cagagtcacc   60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
```

```
gaagattttg caacttacta ctgtcaacag agttacagta ccccgtacac ttttggccag    300
gggaccaagc tggagatcaa a                                              321
```

<210> SEQ ID NO 298
<211> LENGTH: 107
<212> TYPE: PRT
<213> ORGANISM: Artificial Sequence
<220> FEATURE:
<223> OTHER INFORMATION: Synthetic

<400> SEQUENCE: 298

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299

```
cagagcatta gcagctat                                                   18
```

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

```
Gln Ser Ile Ser Ser Tyr
1               5
```

<210> SEQ ID NO 301
<211> LENGTH: 9
<212> TYPE: DNA
<213> ORGANISM: Artificial Sequence
<220> FEATURE:
<223> OTHER INFORMATION: Synthetic

<400> SEQUENCE: 301

```
gctgcatcc                                                              9
```

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacagagtt acagtacccc gtacact                                         27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Ser Tyr Ser Thr Pro Tyr Thr
1               5

<210> SEQ ID NO 305
<211> LENGTH: 351
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctggggaggtc cctgagactc     60 tcctgtgcag cgtctggatt caccttcagt aactatggca tgcactgggt ccgccaggct    120
ccaggcaagg ggctggagtg ggtggcagtt atattgtatg atggaagtaa taaatactat    180
acagactccg tgaagggccg attcaccatc tccagagaca attccaagaa cacgctgtat    240
ctgcaaatga acagcctgag agccgaggac acggctgtgt attactgtgc gagagataac    300
tggaactctt ttgactactg gggccaggga accctggtca ccgtctcctc a             351

<210> SEQ ID NO 306
<211> LENGTH: 117
<212> TYPE: PRT
<213> ORGANISM: Artificial Sequence
<220> FEATURE:
<223> OTHER INFORMATION: Synthetic

<400> SEQUENCE: 306

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Leu Tyr Asp Gly Ser Asn Lys Tyr Tyr Thr Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Arg Asp Asn Trp Asn Ser Phe Asp Tyr Trp Gly Gln Gly Thr Leu
        100                 105                 110

Val Thr Val Ser Ser
        115

<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307
ggattcacct tcagtaacta tggc                                          24

<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Thr Phe Ser Asn Tyr Gly
1               5

<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309
atattgtatg atggaagtaa taaa                                          24

<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Leu Tyr Asp Gly Ser Asn Lys
1               5

<210> SEQ ID NO 311
<211> LENGTH: 30
<212> TYPE: DNA
<213> ORGANISM: Artificial Sequence
<220> FEATURE:
<223> OTHER INFORMATION: Synthetic

<400> SEQUENCE: 311
gcgagagata actggaactc ttttgactac                                    30

<210> SEQ ID NO 312
<211> LENGTH: 10
<212> TYPE: PRT
<213> ORGANISM: Artificial Sequence
<220> FEATURE:
<223> OTHER INFORMATION: Synthetic

<400> SEQUENCE: 312
```

Ala Arg Asp Asn Trp Asn Ser Phe Asp Tyr
1               5                   10

<210> SEQ ID NO 313
<211> LENGTH: 321
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatact gcatccagtt tacaaagtgg ggtcccatca     180
aggttcagtg gcagtggatc tgggacagat ttcactctca ccatcagcag tctgcaacct     240
gaagattttg caacttacta ctgtcaacag agttacacta ccccattcac tttcggccct     300
gggaccaaag tggatatcaa a                                                321

<210> SEQ ID NO 314
<211> LENGTH: 107
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Phe
                85                  90                  95

Thr Phe Gly Pro Gly Thr Lys Val Asp Ile Lys
            100                 105

<210> SEQ ID NO 315
<211> LENGTH: 18
<212> TYPE: DNA
<213> ORGANISM: Artificial Sequence
<220> FEATURE:
<223> OTHER INFORMATION: Synthetic

<400> SEQUENCE: 315
cagagcatta gcagctat                                                    18

<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Ser Ile Ser Ser Tyr
1               5

<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317 actgcatcc                                                                   9

<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Thr Ala Ser
1

<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319
caacagagtt acactacccc attcact                                              27

<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Gln Ser Tyr Thr Thr Pro Phe Thr
1               5

<210> SEQ ID NO 321
<211> LENGTH: 375
<212> TYPE: DNA
<213> ORGANISM: Artificial Sequence
<220> FEATURE:
<223> OTHER INFORMATION: Synthetic

<400> SEQUENCE: 321
gaggtgcagc tggtggagtc tgggggaggc ttggtccagc ctggggggtc cctgagactc          60
tcctgtgcag cctctggatt cacctttagt agctattgga tgagctgggt ccgccaggct         120
ccagggaagg ggctggagtg ggtggccaac ataaagcaag atggaagtga aaatactat          180 gtggactctg tgaagggccg attcaccatc tccagagaca acgccaagaa ctcactgtat         240
ctgcaaatga acagcctgag agccgaggac acggctgtgt attactgtgc gagagagagg         300
gtagtagtac cagctgctat accccactgg tacttcgatc tctggggccg tggcaccctg         360
gtcaccgtct cctca                                                         375

<210> SEQ ID NO 322

```
<211> LENGTH: 125
<212> TYPE: PRT
<213> ORGANISM: Artificial Sequence
<220> FEATURE:
<223> OTHER INFORMATION: Synthetic

<400> SEQUENCE: 322
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Val Val Val Pro Ala Ala Ile Pro His Trp Tyr Phe
            100                 105                 110

Asp Leu Trp Gly Arg Gly Thr Leu Val Thr Val Ser Ser
        115                 120                 125

```
<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323
ggattcacct ttagtagcta ttgg                                        24

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324
```

Gly Phe Thr Phe Ser Ser Tyr Trp
1               5

```
<210> SEQ ID NO 325
<211> LENGTH: 24
<212> TYPE: DNA
<213> ORGANISM: Artificial Sequence
<220> FEATURE:
<223> OTHER INFORMATION: Synthetic

<400> SEQUENCE: 325
ataaagcaag atggaagtga gaaa                                        24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326
```

```
Ile Lys Gln Asp Gly Ser Glu Lys
1               5
```

<210> SEQ ID NO 327
<211> LENGTH: 54
<212> TYPE: DNA
<213> ORGANISM: Artificial Sequence
<220> FEATURE:
<223> OTHER INFORMATION: Synthetic

<400> SEQUENCE: 327

```
gcgagagaga gggtagtagt accagctgct atacccact ggtacttcga tctc       54
```

<210> SEQ ID NO 328
<211> LENGTH: 18
<212> TYPE: PRT
<213> ORGANISM: Artificial Sequence
<220> FEATURE:
<223> OTHER INFORMATION: Synthetic

<400> SEQUENCE: 328

```
Ala Arg Glu Arg Val Val Val Pro Ala Ala Ile Pro His Trp Tyr Phe
1               5                   10                  15

Asp Leu
```

<210> SEQ ID NO 329
<211> LENGTH: 339
<212> TYPE: DNA
<213> ORGANISM: Artificial Sequence
<220> FEATURE:
<223> OTHER INFORMATION: Synthetic

<400> SEQUENCE: 329

```
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttatagtact   300
cctcggacgt tcggccaagg gaccaaggtg gaaatcaaa                          339
```

<210> SEQ ID NO 330
<211> LENGTH: 113
<212> TYPE: PRT
<213> ORGANISM: Artificial Sequence
<220> FEATURE:
<223> OTHER INFORMATION: Synthetic

<400> SEQUENCE: 330

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95
```

Tyr Tyr Ser Thr Pro Arg Thr Phe Gly Gln Gly Thr Lys Val Glu Ile
            100                 105                 110
Lys

<210> SEQ ID NO 331
<211> LENGTH: 36
<212> TYPE: DNA
<213> ORGANISM: Artificial Sequence
<220> FEATURE:
<223> OTHER INFORMATION: Synthetic

<400> SEQUENCE: 331
cagagtgttt tatacagctc caacaataag aactac                                36

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332

Gln Ser Val Leu Tyr Ser Ser Asn Asn Lys Asn Tyr
1               5                   10

<210> SEQ ID NO 333
<211> LENGTH: 9
<212> TYPE: DNA
<213> ORGANISM: Artificial Sequence
<220> FEATURE:
<223> OTHER INFORMATION: Synthetic

<400> SEQUENCE: 333 tgggcatct                                                               9

<210> SEQ ID NO 334
<211> LENGTH: 3
<212> TYPE: PRT
<213> ORGANISM: Artificial Sequence
<220> FEATURE:
<223> OTHER INFORMATION: Synthetic

<400> SEQUENCE: 334

Trp Ala Ser
1

<210> SEQ ID NO 335
<211> LENGTH: 27
<212> TYPE: DNA
<213> ORGANISM: Artificial Sequence
<220> FEATURE:
<223> OTHER INFORMATION: Synthetic

<400> SEQUENCE: 335
cagcaatatt atagtactcc tcggacg                                           27

<210> SEQ ID NO 336
<211> LENGTH: 9
<212> TYPE: PRT
<213> ORGANISM: Artificial Sequence
<220> FEATURE:
<223> OTHER INFORMATION: Synthetic

<400> SEQUENCE: 336

Gln Gln Tyr Tyr Ser Thr Pro Arg Thr

```
<210> SEQ ID NO 337
<211> LENGTH: 375
<212> TYPE: DNA
<213> ORGANISM: Artificial Sequence
<220> FEATURE:
<223> OTHER INFORMATION: Synthetic

<400> SEQUENCE: 337
caggttcagc tggtgcagtc tggagctgag gtgaagaagc ctggggcctc agtgaaggtc      60
tcctgcaagg cttctggtta cacctttacc agctatggta tcagctgggt gcgacaggcc     120
cctggacaag gcttgagtg gatgggatgg atcagcgctt acaatggtaa cacaaactat      180
gcacagaagc tccagggcag agtcaccatg accacagaca catccacgag cacagcctac     240
atggagctga ggagcctgag atctgacgac acggccgtgt attactgtgc gagagcgtat     300
tacgatattt tgactggtta ttactactac ggtatggacg tctggggcca agggaccacg     360
gtcaccgtct cctca                                                      375

<210> SEQ ID NO 338
<211> LENGTH: 125
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ala Tyr Tyr Asp Ile Leu Thr Gly Tyr Tyr Tyr Tyr Gly Met
            100                 105                 110

Asp Val Trp Gly Gln Gly Thr Thr Val Thr Val Ser Ser
        115                 120                 125

<210> SEQ ID NO 339
<211> LENGTH: 24
<212> TYPE: DNA
<213> ORGANISM: Artificial Sequence
<220> FEATURE:
<223> OTHER INFORMATION: Synthetic

<400> SEQUENCE: 339
ggttacacct ttaccagcta tggt                                             24

<210> SEQ ID NO 340
<211> LENGTH: 8
<212> TYPE: PRT
<213> ORGANISM: Artificial Sequence
<220> FEATURE:
<223> OTHER INFORMATION: Synthetic
```

```
<400> SEQUENCE: 340

Gly Tyr Thr Phe Thr Ser Tyr Gly
1               5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atcagcgctt acaatggtaa caca                                              24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ser Ala Tyr Asn Gly Asn Thr
1               5

<210> SEQ ID NO 343
<211> LENGTH: 54
<212> TYPE: DNA
<213> ORGANISM: Artificial Sequence
<220> FEATURE:
<223> OTHER INFORMATION: Synthetic

<400> SEQUENCE: 343
gcgagagcgt attacgatat tttgactggt tattactact acggtatgga cgtc             54

<210> SEQ ID NO 344
<211> LENGTH: 18
<212> TYPE: PRT
<213> ORGANISM: Artificial Sequence
<220> FEATURE:
<223> OTHER INFORMATION: Synthetic

<400> SEQUENCE: 344

Ala Arg Ala Tyr Tyr Asp Ile Leu Thr Gly Tyr Tyr Tyr Gly Met
1               5                   10                  15

Asp Val

<210> SEQ ID NO 345
<211> LENGTH: 333
<212> TYPE: DNA
<213> ORGANISM: Artificial Sequence
<220> FEATURE:
<223> OTHER INFORMATION: Synthetic

<400> SEQUENCE: 345
gacatccaga tgacccagtc tccatcctcc ctgtctgcat ctgtaggaga cagagtcacc       60
atcacttgcc aggcgagtca ggacattagc aactatttaa attggtatca gcagaaacca      120
gggaaagccc ctaagctcct gatctacgat gcatccaatt tggaaacagg ggtcccatca      180
aggttcagtg gaagtggatc tgggacagat tttactttca ccatcagcag cctgcagcct      240
gaagatattg caacatatta ctgtcaacag tatgataatc tccctccggg gggttcattc      300
actttcggcc ctgggaccaa agtggatatc aaa                                   333
```

```
<210> SEQ ID NO 346
<211> LENGTH: 111
<212> TYPE: PRT
<213> ORGANISM: Artificial Sequence
<220> FEATURE:
<223> OTHER INFORMATION: Synthetic

<400> SEQUENCE: 346
```

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Pro
                85                  90                  95

Gly Gly Ser Phe Thr Phe Gly Pro Gly Thr Lys Val Asp Ile Lys
            100                 105                 110

```
<210> SEQ ID NO 347
<211> LENGTH: 18
<212> TYPE: DNA
<213> ORGANISM: Artificial Sequence
<220> FEATURE:
<223> OTHER INFORMATION: Synthetic

<400> SEQUENCE: 347
caggacatta gcaactat                                                       18

<210> SEQ ID NO 348
<211> LENGTH: 6
<212> TYPE: PRT
<213> ORGANISM: Artificial Sequence
<220> FEATURE:
<223> OTHER INFORMATION: Synthetic

<400> SEQUENCE: 348
```

Gln Asp Ile Ser Asn Tyr
1               5

```
<210> SEQ ID NO 349
<211> LENGTH: 9
<212> TYPE: DNA
<213> ORGANISM: Artificial Sequence
<220> FEATURE:
<223> OTHER INFORMATION: Synthetic

<400> SEQUENCE: 349 gatgcatcc                                                                  9

<210> SEQ ID NO 350
<211> LENGTH: 3
<212> TYPE: PRT
<213> ORGANISM: Artificial Sequence
<220> FEATURE:
<223> OTHER INFORMATION: Synthetic

<400> SEQUENCE: 350
```

Asp Ala Ser
1

<210> SEQ ID NO 351
<211> LENGTH: 39
<212> TYPE: DNA
<213> ORGANISM: Artificial Sequence
<220> FEATURE:
<223> OTHER INFORMATION: Synthetic

<400> SEQUENCE: 351
caacagtatg ataatctccc tccgggggt tcattcact                    39

<210> SEQ ID NO 352
<211> LENGTH: 13
<212> TYPE: PRT
<213> ORGANISM: Artificial Sequence
<220> FEATURE:
<223> OTHER INFORMATION: Synthetic

<400> SEQUENCE: 352

Gln Gln Tyr Asp Asn Leu Pro Pro Gly Gly Ser Phe Thr
1               5                   10

<210> SEQ ID NO 353
<211> LENGTH: 360
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtacagc ctgggggtc cctgagactc     60 tcctgtgcag cctctggatt cacctttagc agtatgcca tgagctgggt ccgccaggct    120
ccagggaagg ggctggaatg ggtctcaggt cttagtggta gtggtggtag cacatactac    180
gcagactccg tgaagggccg gttcaccatc tccagagaca attccaagaa cacgctgtat    240
ctgcaaatga acagcctgag agccgaggac acggccgtat attattgtgc gaaagagaaa    300
tataattgga aatttcactt tgactactgg ggccaggaa ccctggtcac cgtctcctca    360

<210> SEQ ID NO 354
<211> LENGTH: 120
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Leu Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Lys Tyr Asn Trp Lys Phe His Phe Asp Tyr Trp Gly Gln

```
                100               105               110
Gly Thr Leu Val Thr Val Ser Ser
        115                 120

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttagcagtta tgcc                                          24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Gly Phe Thr Phe Ser Ser Tyr Ala
1               5

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
cttagtggta gtggtggtag caca                                          24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Leu Ser Gly Ser Gly Gly Ser Thr
1               5

<210> SEQ ID NO 359
<211> LENGTH: 39
<212> TYPE: DNA
<213> ORGANISM: Artificial Sequence
<220> FEATURE:
<223> OTHER INFORMATION: Synthetic

<400> SEQUENCE: 359
gcgaaagaga aatataattg gaaatttcac tttgactac                          39

<210> SEQ ID NO 360
<211> LENGTH: 13
<212> TYPE: PRT
<213> ORGANISM: Artificial Sequence
<220> FEATURE:
<223> OTHER INFORMATION: Synthetic

<400> SEQUENCE: 360

Ala Lys Glu Lys Tyr Asn Trp Lys Phe His Phe Asp Tyr
1               5                   10
```

<210> SEQ ID NO 361
<211> LENGTH: 321
<212> TYPE: DNA
<213> ORGANISM: Artificial Sequence
<220> FEATURE:
<223> OTHER INFORMATION: Synthetic

<400> SEQUENCE: 361

```
gacatccaga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg aagtggatc tgggacagat tttactttca ccatcagcag cctgcagcct     240
gaagatattg caacatatta ctgtcaacag tatgataatc tcccgctcac tttcggcgga     300
gggaccaagg tggagatcaa a                                               321
```

<210> SEQ ID NO 362
<211> LENGTH: 107
<212> TYPE: PRT
<213> ORGANISM: Artificial Sequence
<220> FEATURE:
<223> OTHER INFORMATION: Synthetic

<400> SEQUENCE: 362

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105
```

<210> SEQ ID NO 363
<211> LENGTH: 18
<212> TYPE: DNA
<213> ORGANISM: Artificial Sequence
<220> FEATURE:
<223> OTHER INFORMATION: Synthetic

<400> SEQUENCE: 363

```
caggacatta gcaactat                                                    18
```

<210> SEQ ID NO 364
<211> LENGTH: 6
<212> TYPE: PRT
<213> ORGANISM: Artificial Sequence
<220> FEATURE:
<223> OTHER INFORMATION: Synthetic

<400> SEQUENCE: 364

```
Gln Asp Ile Ser Asn Tyr
1               5
```

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 gatgcatcc                                                                 9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Asp Ala Ser
1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
caacagtatg ataatctccc gctcact                                            27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Tyr Asp Asn Leu Pro Leu Thr
1               5

<210> SEQ ID NO 369
<211> LENGTH: 354
<212> TYPE: DNA
<213> ORGANISM: Artificial Sequence
<220> FEATURE:
<223> OTHER INFORMATION: Synthetic

<400> SEQUENCE: 369
caggttcagc tggtgcagtc tggagctgag gtgaagaagc ctggggcctc agtgaaggtc        60
tcctgcaagg cttctggtta cacctttacc agctatggta tcagctgggt gcgacaggcc      120
cctggacaag gcttgagtg gatgggatgg atcagcgctt acaatggtaa cacaaactat       180
gcacagaagc tccagggcag agtcaccatg accacagaca catccacgag cacagcctac      240
atggagctga ggagcctgag atctgacgac acggccgtgt attactgtgc gagagatggg      300
agctactcct ggttcgaccc ctggggccag gaaccctgg tcaccgtctc ctca              354

<210> SEQ ID NO 370
<211> LENGTH: 118
<212> TYPE: PRT
<213> ORGANISM: Artificial Sequence
<220> FEATURE:
<223> OTHER INFORMATION: Synthetic

<400> SEQUENCE: 370

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Gly Ser Tyr Ser Trp Phe Asp Pro Trp Gly Gln Gly Thr
            100                 105                 110

Leu Val Thr Val Ser Ser
        115

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggttacacct ttaccagcta tggt                                    24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Tyr Thr Phe Thr Ser Tyr Gly
1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
atcagcgctt acaatggtaa caca                                    24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Ala Tyr Asn Gly Asn Thr
1               5

<210> SEQ ID NO 375

```
<211> LENGTH: 33
<212> TYPE: DNA
<213> ORGANISM: Artificial Sequence
<220> FEATURE:
<223> OTHER INFORMATION: Synthetic

<400> SEQUENCE: 375
gcgagagatg ggagctactc ctggttcgac ccc                                    33

<210> SEQ ID NO 376
<211> LENGTH: 11
<212> TYPE: PRT
<213> ORGANISM: Artificial Sequence
<220> FEATURE:
<223> OTHER INFORMATION: Synthetic

<400> SEQUENCE: 376

Ala Arg Asp Gly Ser Tyr Ser Trp Phe Asp Pro
1               5                   10

<210> SEQ ID NO 377
<211> LENGTH: 321
<212> TYPE: DNA
<213> ORGANISM: Artificial Sequence
<220> FEATURE:
<223> OTHER INFORMATION: Synthetic

<400> SEQUENCE: 377
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcaacag agttacagta ccccgctcac tttcggcgga      300
gggaccaagg tggagatcaa a                                                321

<210> SEQ ID NO 378
<211> LENGTH: 107
<212> TYPE: PRT
<213> ORGANISM: Artificial Sequence
<220> FEATURE:
<223> OTHER INFORMATION: Synthetic

<400> SEQUENCE: 378

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 379
<211> LENGTH: 18
```

<212> TYPE: DNA
<213> ORGANISM: Artificial Sequence
<220> FEATURE:
<223> OTHER INFORMATION: Synthetic

<400> SEQUENCE: 379
cagagcatta gcagctat                                                      18

<210> SEQ ID NO 380
<211> LENGTH: 6
<212> TYPE: PRT
<213> ORGANISM: Artificial Sequence
<220> FEATURE:
<223> OTHER INFORMATION: Synthetic

<400> SEQUENCE: 380

Gln Ser Ile Ser Ser Tyr
1               5

<210> SEQ ID NO 381
<211> LENGTH: 9
<212> TYPE: DNA
<213> ORGANISM: Artificial Sequence
<220> FEATURE:
<223> OTHER INFORMATION: Synthetic

<400> SEQUENCE: 381 gctgcatcc                                                                 9

<210> SEQ ID NO 382
<211> LENGTH: 3
<212> TYPE: PRT
<213> ORGANISM: Artificial Sequence
<220> FEATURE:
<223> OTHER INFORMATION: Synthetic

<400> SEQUENCE: 382

Ala Ala Ser
1

<210> SEQ ID NO 383
<211> LENGTH: 27
<212> TYPE: DNA
<213> ORGANISM: Artificial Sequence
<220> FEATURE:
<223> OTHER INFORMATION: Synthetic

<400> SEQUENCE: 383
caacagagtt acagtacccc gctcact                                            27

<210> SEQ ID NO 384
<211> LENGTH: 9
<212> TYPE: PRT
<213> ORGANISM: Artificial Sequence
<220> FEATURE:
<223> OTHER INFORMATION: Synthetic

<400> SEQUENCE: 384

Gln Gln Ser Tyr Ser Thr Pro Leu Thr
1               5

<210> SEQ ID NO 385
<211> LENGTH: 360
<212> TYPE: DNA
<213> ORGANISM: Artificial Sequence
<220> FEATURE:
<223> OTHER INFORMATION: Synthetic

<400> SEQUENCE: 385

```
caggtgcagc tgcaggagtc gggcccagga ctggtgaagc cttcggagac cctgtccctc    60
acctgcactg tctctggtgg ctccatcagt agttactact ggagctggat ccggcagccc   120
ccagggaagg gactggagtg gattgggtat atctattaca gtgggagcac caagtacaac   180
ccctccctca gagtcgagt  caccatatca gtagacacgt ccaagaacca gttctccctg   240
aagctgagct ctgtgaccgc cgaagacacg gccgtgtatt actgtgggag acaaagtggg   300
agctactact actacggtat ggacgtctgg ggccaaggga ccacggtcac cgtctcctca   360
```

<210> SEQ ID NO 386
<211> LENGTH: 120
<212> TYPE: PRT
<213> ORGANISM: Artificial Sequence
<220> FEATURE:
<223> OTHER INFORMATION: Synthetic

<400> SEQUENCE: 386

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Glu Asp Thr Ala Val Tyr Tyr Cys Gly
                85                  90                  95

Arg Gln Ser Gly Ser Tyr Tyr Tyr Tyr Gly Met Asp Val Trp Gly Gln
            100                 105                 110

Gly Thr Thr Val Thr Val Ser Ser
        115                 120
```

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387

```
ggtggctcca tcagtagtta ctac                                           24
```

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

```
Gly Gly Ser Ile Ser Ser Tyr Tyr
1               5
```

<210> SEQ ID NO 389
<211> LENGTH: 21
<212> TYPE: DNA
<213> ORGANISM: Artificial Sequence

```
<220> FEATURE:
<223> OTHER INFORMATION: Synthetic

<400> SEQUENCE: 389
atctattaca gtgggagcac c                                              21

<210> SEQ ID NO 390
<211> LENGTH: 7
<212> TYPE: PRT
<213> ORGANISM: Artificial Sequence
<220> FEATURE:
<223> OTHER INFORMATION: Synthetic

<400> SEQUENCE: 390

Ile Tyr Tyr Ser Gly Ser Thr
1               5

<210> SEQ ID NO 391
<211> LENGTH: 42
<212> TYPE: DNA
<213> ORGANISM: Artificial Sequence
<220> FEATURE:
<223> OTHER INFORMATION: Synthetic

<400> SEQUENCE: 391
gggagacaaa gtgggagcta ctactactac ggtatggacg tc                       42

<210> SEQ ID NO 392
<211> LENGTH: 14
<212> TYPE: PRT
<213> ORGANISM: Artificial Sequence
<220> FEATURE:
<223> OTHER INFORMATION: Synthetic

<400> SEQUENCE: 392

Gly Arg Gln Ser Gly Ser Tyr Tyr Tyr Tyr Gly Met Asp Val
1               5                   10

<210> SEQ ID NO 393
<211> LENGTH: 321
<212> TYPE: DNA
<213> ORGANISM: Artificial Sequence
<220> FEATURE:
<223> OTHER INFORMATION: Synthetic

<400> SEQUENCE: 393
gacatccaga tgacccagtc tccatcctcc ctgtctgcat ctgtaggaga cagagtcacc    60
atcacttgcc gggcaagtca aagcattagc agctatttaa attggtatca gcagaaacca   120
gggaaagccc ctaagctcct gatctatgct gcatccagtt tgcaaagtgg agtcccatca   180
aggttcagtg gcagtggatc tgggacagat ttcactctca ccatcagcag tctgcaacct   240
gaagattttg caacttacta ctgtcaacag agttacagta ccccgtacac ttttggccag   300
gggaccaagc tggagatcaa a                                             321

<210> SEQ ID NO 394
<211> LENGTH: 107
<212> TYPE: PRT
<213> ORGANISM: Artificial Sequence
<220> FEATURE:
<223> OTHER INFORMATION: Synthetic

<400> SEQUENCE: 394

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 395
<211> LENGTH: 18
<212> TYPE: DNA
<213> ORGANISM: Artificial Sequence
<220> FEATURE:
<223> OTHER INFORMATION: Synthetic

<400> SEQUENCE: 395
caaagcatta gcagctat                                                   18

<210> SEQ ID NO 396
<211> LENGTH: 6
<212> TYPE: PRT
<213> ORGANISM: Artificial Sequence
<220> FEATURE:
<223> OTHER INFORMATION: Synthetic

<400> SEQUENCE: 396

```
Gln Ser Ile Ser Ser Tyr
1               5
```

<210> SEQ ID NO 397
<211> LENGTH: 9
<212> TYPE: DNA
<213> ORGANISM: Artificial Sequence
<220> FEATURE:
<223> OTHER INFORMATION: Synthetic

<400> SEQUENCE: 397 gctgcatcc                                                              9

<210> SEQ ID NO 398
<211> LENGTH: 3
<212> TYPE: PRT
<213> ORGANISM: Artificial Sequence
<220> FEATURE:
<223> OTHER INFORMATION: Synthetic

<400> SEQUENCE: 398

```
Ala Ala Ser
1
```

<210> SEQ ID NO 399
<211> LENGTH: 27
<212> TYPE: DNA
<213> ORGANISM: Artificial Sequence
<220> FEATURE:
<223> OTHER INFORMATION: Synthetic

<400> SEQUENCE: 399

```
caacagagtt acagtacccc gtacact                                              27
```

<210> SEQ ID NO 400
<211> LENGTH: 9
<212> TYPE: PRT
<213> ORGANISM: Artificial Sequence
<220> FEATURE:
<223> OTHER INFORMATION: Synthetic
<400> SEQUENCE: 400

Gln Gln Ser Tyr Ser Thr Pro Tyr Thr
1               5

<210> SEQ ID NO 401
<211> LENGTH: 528
<212> TYPE: PRT
<213> ORGANISM: Homo sapiens
<400> SEQUENCE: 401

Met Glu Leu Lys Ala Glu Glu Val Gly Gly Val Gln Pro Val
1               5                   10                  15

Ser Ile Gln Ala Phe Ala Ser Ser Thr Leu His Gly Leu Ala His
                20                  25                  30

Ile Phe Ser Tyr Glu Arg Leu Ser Leu Lys Arg Ala Leu Trp Ala Leu
            35                  40                  45

Cys Phe Leu Gly Ser Leu Ala Val Leu Leu Cys Val Cys Thr Glu Arg
        50                  55                  60

Val Gln Tyr Tyr Phe His Tyr His His Val Thr Lys Leu Asp Glu Val
65                  70                  75                  80

Ala Ala Ser Gln Leu Thr Phe Pro Ala Val Thr Leu Cys Asn Leu Asn
                85                  90                  95

Glu Phe Arg Phe Ser Gln Val Ser Lys Asn Asp Leu Tyr His Ala Gly
                100                 105                 110

Glu Leu Leu Ala Leu Leu Asn Asn Arg Tyr Glu Ile Pro Asp Thr Gln
            115                 120                 125

Met Ala Asp Glu Lys Gln Leu Glu Ile Leu Gln Asp Lys Ala Asn Phe
    130                 135                 140

Arg Ser Phe Lys Pro Lys Pro Phe Asn Met Arg Glu Phe Tyr Asp Arg
145                 150                 155                 160

Ala Gly His Asp Ile Arg Asp Met Leu Leu Ser Cys His Phe Arg Gly
                165                 170                 175

Glu Val Cys Ser Ala Glu Asp Phe Lys Val Val Phe Thr Arg Tyr Gly
            180                 185                 190

Lys Cys Tyr Thr Phe Asn Ser Gly Arg Asp Gly Arg Pro Arg Leu Lys
        195                 200                 205

Thr Met Lys Gly Gly Thr Gly Asn Gly Leu Glu Ile Met Leu Asp Ile
    210                 215                 220

Gln Gln Asp Glu Tyr Leu Pro Val Trp Gly Glu Thr Asp Glu Thr Ser
225                 230                 235                 240

Phe Glu Ala Gly Ile Lys Val Gln Ile His Ser Gln Asp Glu Pro Pro
                245                 250                 255

Phe Ile Asp Gln Leu Gly Phe Gly Val Ala Pro Gly Phe Gln Thr Phe
            260                 265                 270

Val Ala Cys Gln Glu Gln Arg Leu Ile Tyr Leu Pro Pro Pro Trp Gly
        275                 280                 285

Thr Cys Lys Ala Val Thr Met Asp Ser Asp Leu Asp Phe Phe Asp Ser
    290                 295                 300

```
Tyr Ser Ile Thr Ala Cys Arg Ile Asp Cys Glu Thr Arg Tyr Leu Val
305                 310                 315                 320

Glu Asn Cys Asn Cys Arg Met Val His Met Pro Gly Asp Ala Pro Tyr
            325                 330                 335

Cys Thr Pro Glu Gln Tyr Lys Glu Cys Ala Asp Pro Ala Leu Asp Phe
            340                 345                 350

Leu Val Glu Lys Asp Gln Glu Tyr Cys Val Cys Glu Met Pro Cys Asn
            355                 360                 365

Leu Thr Arg Tyr Gly Lys Glu Leu Ser Met Val Lys Ile Pro Ser Lys
        370                 375                 380

Ala Ser Ala Lys Tyr Leu Ala Lys Lys Phe Asn Lys Ser Glu Gln Tyr
385                 390                 395                 400

Ile Gly Glu Asn Ile Leu Val Leu Asp Ile Phe Phe Glu Val Leu Asn
                405                 410                 415

Tyr Glu Thr Ile Glu Gln Lys Lys Ala Tyr Glu Ile Ala Gly Leu Leu
            420                 425                 430

Gly Asp Ile Gly Gly Gln Met Gly Leu Phe Ile Gly Ala Ser Ile Leu
            435                 440                 445

Thr Val Leu Glu Leu Phe Asp Tyr Ala Tyr Glu Val Ile Lys His Lys
        450                 455                 460

Leu Cys Arg Arg Gly Lys Cys Gln Lys Glu Ala Lys Arg Ser Ser Ala
465                 470                 475                 480

Asp Lys Gly Val Ala Leu Ser Leu Asp Asp Val Lys Arg His Asn Pro
                485                 490                 495

Cys Glu Ser Leu Arg Gly His Pro Ala Gly Met Thr Tyr Ala Ala Asn
            500                 505                 510

Ile Leu Pro His His Pro Ala Arg Gly Thr Phe Glu Asp Phe Thr Cys
        515                 520                 525
```

ANTI-ASIC1 ANTIBODIES AND USES THEREOF

CROSS-REFERENCE TO RELATED APPLICATIONS

This application is a continuation of U.S. patent application Ser. No. 14/848,452, filed on Sep. 9, 2015, entitled "Anti-ASIC1 Antibodies and Uses Thereof". U.S. patent application Ser. No. 14/848,452 is a continuation of U.S. patent application Ser. No. 13/753,836, filed on Jan. 30, 2013, now U.S. Pat. No. 9,150,648, which claims the benefit under 35 U.S.C. § 119(e) of U.S. provisional application Nos. 61/592,837, filed on Jan. 31, 2012; 61/644,038, filed on May 8, 2012; and 61/692,925, filed on Aug. 24, 2012, which applications are herein specifically incorporated by reference in their entirety.

FIELD OF THE INVENTION

The present invention relates to antibodies, and antigen-binding fragments thereof, which are specific for human ASIC1, and methods of use thereof.

BACKGROUND

Acid sensing ion channels (ASICs) are proton-gated cationic channels expressed in the central and peripheral nervous systems. The ASIC family in humans includes ASIC1, ASIC2, ASIC3 and ASIC4 subunits which arrange into homo- or heteromultimeric ion channels in neuronal membranes. ASIC1, ASIC2 and ASIC3 are significantly expressed in the small and medium nociceptive sensory neurons that are able to detect noxious chemical, thermal, and high threshold mechanical stimuli. ASIC2 and ASIC3 are also expressed in large neurons that mostly correspond to low threshold mechanoreceptors.

ASICs are permeable to $Na^+$ and $Ca^{2+}$ ions and are activated by external pH variations ranging from pH 6.8 to 4.0. ASICs are believed to play an important role in sensing local acidosis. Local tissue acidosis is a hallmark of pain and inflammation, and inflamed tissues frequently exhibit low pH (as low as ~4.7). Blockage of ASICs has been proposed as a method for treating a variety of disorders and conditions. Blockage of ASIC1 in particular has been proposed as a means for treating conditions such as pain, neurodegenerative diseases, and psychiatric diseases.

Pharmacologic inhibitors of ASIC1 include the tarantula peptide Psalmotoxin-1 (PcTx1) which specifically inhibits ASIC1 homomers, and the small molecule, non-selective ASIC inhibitors amiloride and A-317567. The 40-amino acid peptide toxin APETx2, isolated from sea anemone, has been shown to inhibit ASIC3 homomers as well as ASIC3/1 and ASIC3/2 heteromers.

Currently, there are no known antibodies that specifically block ASICs. Thus, there is a need in the art for novel ASIC inhibitors, such as anti-ASIC1 antibodies, that can be used to treat diseases and conditions mediated by ASIC signaling.

BRIEF SUMMARY OF THE INVENTION

The present invention provides antibodies that specifically bind human ASIC1, including, e.g., antibodies that specifically bind cell surface-expressed ASIC1. The antibodies of the present invention, according to certain embodiments, inhibit acid-induced, ASIC1-mediated ion currents in cells expressing human ASIC1. The antibodies of the invention are useful, inter alia, for inhibiting ASIC1-mediated signaling and for treating diseases and disorders caused by or related to ASIC1 activity and/or signaling. For example, the antibodies of the present invention can be administered to a patient for the treatment or alleviation of pain and related conditions.

The antibodies of the invention can be full-length (for example, an IgG1 or IgG4 antibody) or may comprise only an antigen-binding portion (for example, a Fab, $F(ab')_2$ or scFv fragment), and may be modified to affect functionality, e.g., to eliminate residual effector functions (Reddy et al., 2000, J. Immunol. 164:1925-1933).

The present invention provides an antibody or antigen-binding fragment of an antibody comprising a heavy chain variable region (HCVR) having an amino acid sequence selected from the group consisting of SEQ ID NO: 2, 18, 34, 50, 66, 82, 98, 114, 130, 146, 162, 178, 194, 210, 226, 242, 258, 274, 290, 306, 322, 338, 354, 370, and 386, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 106, 122, 138, 154, 170, 186, 202, 218, 234, 250, 266, 282, 298, 314, 330, 346, 362, 378, and 394, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, and 386/394.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 120, 136, 152, 168, 184, 200, 216, 232, 248, 264, 280, 296, 312, 328, 344, 360, 376, and 392, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 112, 128, 144, 160, 176, 192, 208, 224, 240, 256, 272, 288, 304, 320, 336, 352, 368, 384, and 400, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/112, 120/128, 136/144, 152/160, 168/176, 184/192, 200/208, 216/224, 232/240, 248/256, 264/272, 280/288, 296/304, 312/320, 328/336, 344/352, 360/368, 376/384, and 392/400.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 116, 132, 148, 164, 180, 196, 212, 228, 244, 260, 276, 292, 308, 324, 340, 356, 372, and 388, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 118, 134, 150, 166, 182, 198, 214, 230, 246, 262, 278, 294, 310, 326, 342, 358, 374, and 390, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 108, 124, 140, 156, 172, 188, 204, 220, 236, 252, 268, 284, 300, 316, 332, 348, 364, 380, and 396, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 110, 126, 142, 158, 174, 190, 206, 222, 238, 254, 270, 286, 302, 318, 334, 350, 366, 382, and 398, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H1M6712N); 20-22-24-28-30-32 (e.g. H1M6716N); 36-38-40-44-46-48 (e.g. H1M6718N); 52-54-56-60-62-64 (e.g. H1M7101N); 68-70-72-76-78-80 (e.g. H2M7103N); 84-86-88-92-94-96 (e.g. H3M6713N); 100-102-104-108-110-112 (e.g. H3M6715N); 116-118-120-124-126-128 (e.g. H3M6720N); 132-134-136-140-142-144 (e.g. H3M6721 N); 148-150-152-156-158-160 (e.g., H3M6721N2); 164-166-168-172-174-176 (e.g. H3M6726N); 180-182-184-188-190-192 (e.g., H3M6760N); 196-198-200-204-206-208 (e.g. H3M7102N); 212-214-216-220-222-224 (e.g. H3M7118N); 228-230-232-236-238-240 (e.g. H4H6362P); 244-246-248-252-254-256 (e.g. H4H6363P); 260-262-264-268-270-272 (e.g. H4H6364P); 276-278-280-284-286-288 (e.g. H4H6366P); 292-294-296-300-302-304 (e.g. H4H6372P); 308-310-312-316-318-320 (e.g. H4H6374P); 324-326-328-332-334-336 (e.g. H4H6375P); 340-342-344-348-350-352 (e.g. H4H6379P); 356-358-360-364-366-368 (e.g. H4H6380P); 372-374-376-380-382-384 (e.g. H4H6381P); and 388-390-392-396-398-400 (e.g. H4H6383P).

In a related embodiment, the invention includes an antibody or antigen-binding fragment of an antibody which specifically binds ASIC1 (e.g., cell surface-expressed ASIC1), wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/106, 114/122, 130/138, 146/154, 162/170, 178/186, 194/202, 210/218, 226/234, 242/250, 258/266, 274/282, 290/298, 306/314, 322/330, 338/346, 354/362, 370/378, and 386/394. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In another aspect, the invention provides nucleic acid molecules encoding anti-ASIC1 antibodies or fragments thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

In one embodiment, the invention provides an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 289, 305, 321, 337, 353, 369, and 385, or a substantially identical sequence having at least 90%, at least 95%, at least 98%, or at least 99% homology thereof.

The present invention also provides an antibody or fragment thereof comprising a LCVR encoded by a nucleic acid sequence selected from the group consisting of SEQ ID NO: 9, 25, 41, 57, 73, 89, 105, 121, 137, 153, 169, 185, 201, 217, 233, 249, 265, 281, 297, 313, 329, 345, 361, 377, and 393, or a substantially identical sequence having at least 90%, at least 95%, at least 98%, or at least 99% homology thereof.

The present invention also provides an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 295, 311, 327, 343, 359, 375, and 391, or a substantially identical sequence having at least 90%, at least 95%, at least 98%, or at least 99% homology thereof; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, 287, 303, 319, 335, 351, 367, 383, and 399, or a substantially identical sequence having at least 90%, at least 95%, at least 98%, or at least 99% homology thereof.

The present invention also provides an antibody or fragment thereof which further comprises a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 291, 307, 323, 339, 355, 371, and 387, or a substantially identical sequence having at least 90%, at least 95%, at least 98%, or at least 99% homology thereof; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 293, 309, 325, 341, 357, 373, and 389, or a substantially identical sequence having at least 90%, at least 95%, at least 98%, or at least 99% homology thereof; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, 283, 299, 315, 331, 347, 363, 379, and 395, or a substantially identical sequence having at least 90%, at least 95%, at least 98%, or at least 99% homology thereof; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, 285, 301, 317, 333, 349, 365, 381, and 397, or a substantially identical sequence having at least 90%, at least 95%, at least 98%, or at least 99% homology thereof.

According to certain embodiments, the antibody or fragment thereof comprises the heavy and light chain CDR sequences encoded by the nucleic acid sequences of SEQ ID NOs: 1 and 9 (e.g. H1M6712N), 17 and 25 (e.g. H1M6716N), 33 and 41 (e.g. H1M6718N), 49 and 57 (e.g. H1M7101N), 65 and 73 (e.g. H2M7103N), 81 and 89 (e.g. H3M6713N), 97 and 105 (e.g. H3M6715N), 113 and 121 (e.g. H3M6720N), 129 and 137 (e.g. H3M6721N), 145 and 153 (e.g. H3M6721N2), 161 and 169 (e.g. H3M6726N), 177 and 185 (e.g. H3M6760N), 193 and 201 (e.g. H3M7102N), 209 and 217 (e.g. H3M7118N), 225 and 233 (e.g. H4H6362P), 241 and 249 (e.g. H4H6363P), 257 and 265 (e.g. H4H6364P), 273 and 281 (e.g. H4H6366P), 289 and 297 (e.g. H4H6372P), 305 and 313 (e.g. H4H6374P), 321 and 329 (e.g. H4H6375P), 337 and 345 (e.g. H4H6379P), 353 and 361 (e.g. H4H6380P), 369 and 377 (e.g. H4H6381 P), 385 and 393 (e.g. H4H6383P).

The present invention includes anti-ASIC1 antibodies having a modified glycosylation pattern. In some applications, modification to remove undesirable glycosylation sites may be useful, or an antibody lacking a fucose moiety present on the oligosaccharide chain.

In another aspect, the invention provides a pharmaceutical composition comprising a recombinant human antibody or fragment thereof which specifically binds ASIC1 (e.g., cell surface-expressed ASIC1) and a pharmaceutically acceptable carrier. In a related aspect, the invention features a composition which is a combination of an anti-ASIC1 antibody and a second therapeutic agent. In one embodiment, the second therapeutic agent is any agent that is advantageously combined with an anti-ASIC1 antibody. Exemplary agents that may be advantageously combined with an anti-ASIC1 antibody include, without limitation, other agents that inhibit ASIC1 activity (including other antibodies or antigen-binding fragments thereof, peptide inhibitors, small molecule antagonists, etc.) and/or agents which do not directly bind ASIC1 but nonetheless interfere with, block or attenuate ASIC1-mediated ion currents in cells.

In yet another aspect, the invention provides methods for inhibiting ASIC1-mediated ion currents using an anti-ASIC1 antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of ASIC1-mediated ion currents. The anti-ASIC1 antibodies or antibody fragments of the invention may function to block acid-induced ASIC1-mediated currents, or otherwise inhibit the signaling activity of ASIC1.

The present invention also includes the use of an anti-ASIC1 antibody or antigen binding portion of an antibody of the invention in the manufacture of a medicament for the treatment of a disease or disorder related to or caused by ASIC1-mediated ion currents in a patient.

Other embodiments will become apparent from a review of the ensuing detailed description.

DETAILED DESCRIPTION

Figure 1:
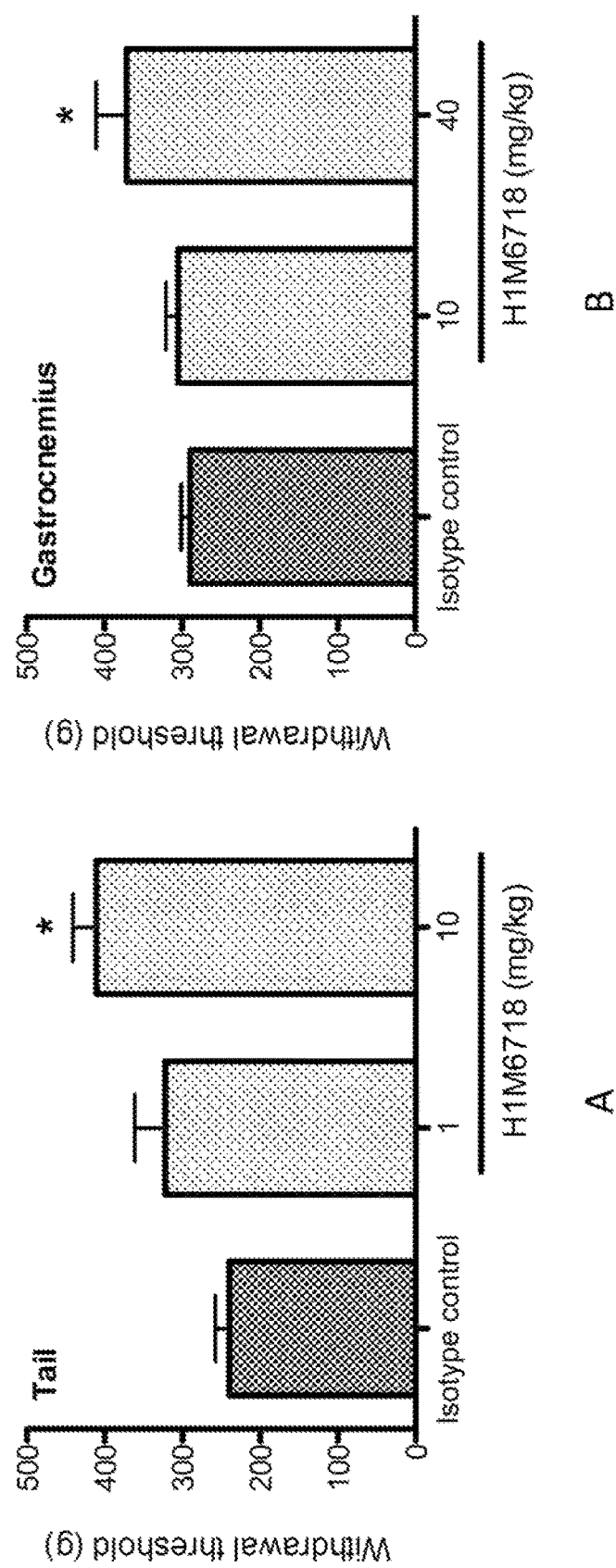
FIG. 1 (panels A and B) depicts the withdrawal thresholds of mice treated with an anti-ASIC1 antibody (H1M6718N), or isotype control antibody, in response to a mechanical pinch of the tail (panel A) or the gastrocnemius muscle (panel B). Results are expressed in terms of withdrawal threshold to the pinch in grams (mean±SEM for each cohort of mice).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expressions "ASIC1" and "ASIC1 fragment," as used herein refer to the human ASIC1 protein or fragment unless specified as being from a non-human species (e.g., "mouse ASIC1," "mouse ASIC1 fragment," "monkey ASIC1," "monkey ASIC1 fragment," etc.). Human ASIC1 has the amino acid sequence as set forth in SEQ ID NO:401). The expression "ASIC1," as used herein, includes soluble fragments of the ASIC1 extracellular domain (e.g., polypeptides comprising or consisting of at least 30 contiguous amino acids found within amino acids 63 to 424 of SEQ ID NO:401), as well as cell surface-expressed ASIC1 (as that term is defined herein below).

As used herein, "an antibody that binds ASIC1" or an "anti-ASIC1 antibody" includes antibodies, and antigen-binding fragments thereof, that bind a soluble fragment of an ASIC1 protein (e.g., a portion of the extracellular domain of ASIC1) and/or cell surface-expressed ASIC1. The expression "cell surface-expressed ASIC1" means one or more ASIC1 protein(s) that is/are expressed on the surface of a cell in vitro or in vivo, such that at least a portion of the ASIC1 protein (e.g., amino acids 63 to 424 of SEQ ID NO:401) is exposed to the extracellular side of the cell membrane and accessible to an antigen-binding portion of an antibody. "Cell surface-expressed ASIC1" includes ASIC1 protein contained within the context of a functional ASIC1 ion channel in the membrane of a cell. In some instances, "cell surface-expressed ASIC1" is an ASIC1 protein that is expressed as part of a heteromultimer on the surface of a cell (e.g., an ASIC1/2, ASIC1/3 or ASIC1/4 heteromultimer). In other instances, "cell surface-expressed ASIC1" is an ASIC1 protein that is expressed as part of a homomultimer on the surface of a cell. Moreover, "cell surface-expressed ASIC1" can comprise or consist of ASIC1 protein expressed on the surface of a cell which normally expressed ASIC1 protein. Alternatively, "cell surface-expressed ASIC1" can comprise or consist of ASIC1 protein expressed on the surface of a cell that normally does not express human ASIC1 on its surface but has been artificially engineered to express ASIC1 on its surface.

The term "antibody", as used herein, means any antigen-binding molecule or molecular complex comprising at least one complementarity determining region (CDR) that specifically binds to or interacts with a particular antigen (e.g., ASIC1). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-ASIC1 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

A "neutralizing" or "blocking" antibody, as used herein, is intended to refer to an antibody whose binding to ASIC1 reduces or detectably inhibits acid-induced ASIC1-mediated ion currents. The inhibition caused by an ASIC1 neutralizing or blocking antibody need not be complete so long as it is detectable using an appropriate assay. Exemplary assays for detecting ASIC1 inhibition are described elsewhere herein.

The anti-ASIC1 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ASIC1 antibodies comprising variants of any of the HCVR, LCVR, and/or CDR amino acid sequences disclosed herein having one or more conservative substitutions. For example, the present invention includes anti-ASIC1 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Biological Characteristics of the Antibodies

The present invention includes antibodies that specifically bind cell surface expressed ASIC1. As used herein, an antibody specifically binds cell surface expressed ASIC1 if the antibody shows detectable binding to a cell that naturally or artificially expresses ASIC1 but does not show detectable binding to an equivalent cell that does not express ASIC1. One exemplary assay format that can be used to determine whether an antibody specifically binds cell surface-expressed ASIC1 is fluorescence activated cell sorting (FACS), as illustrated in Example 3 herein. Qualitative positive FACS binding of an antibody to cells which express ASIC1, as shown in Table 2, can be used to identify an antibody as specifically binding cell surface-expressed ASIC1. FACS can also be used to quantitatively assess antibody binding to cell which express ASIC1 in terms of an $EC_{50}$ value, as shown in Example 3, Table 3. Thus, according to certain embodiments of the present invention, an antibody "specifically binds cell surface-expressed ASIC1" if the antibody, when tested in the FACS assay format of Example 3 or a substantially similar assay format, exhibits an $EC_{50}$ value of about 5 nM or less (e.g., about 5.0 nM, 4.5 nM, 4.0 nM, 3.5 nM, 3.0 nM, 2.5 nM, 2.0 nM, 1.5 nM, 1.4 nM, 1.3 nM, 1.2 nM, 1.1 nM, 1.0 nM, 900 pM, 800 pM, 700 pM, 600 pM, 500 pM, 400 pM, 300 pM, 200 pM, 100 pM, 90 pM, 85 pM, 80 pM, 75 pM, 70 pM, or less).

The antibodies of the present invention, according to certain embodiments, may also (or alternatively) function to inhibit acid-induced, ASIC1-mediated ion currents in cells expressing human ASIC1. As used herein, the expression "inhibits acid-induced, ASIC1-mediated ion currents" means that, in an assay in which acid-induced cellular ion currents or flux can be detected and/or quantified, the addition of an antibody of the invention detectably reduces or inhibits the acid-induced ion currents as compared to the ion currents observed in the absence of the antibody (e.g., in the presence of a non-specific negative control antibody). A non-limiting exemplary assay that can be used to determine if an antibody "inhibits acid-induced, ASIC1-mediated ion currents" is illustrated in Example 4 herein. In this Example, low pH-activated calcium flux is measured in ASIC1-expressing cells in the presence of anti-ASIC1 antibodies ("FLIPR assay"). By varying the amount of antibody used in this assay format, the amount of antibody required to block 50% of low pH-induced ion flux can be calculated and expressed as an $IC_{50}$ value (see, e.g., Example 4, Table 5). The present invention includes anti-ASIC1 antibodies that inhibit acid-induced, ASIC1-mediated ion currents with an $IC_{50}$ of less than about 10 nM when tested in a FLIPR assay at pH of about 5.0 to about 6.0 (e.g., at pH 5.0, 5.1, 5.2, 5.3, 5.4, 5.5, 5.6, 5.7, 5.8, 5.9, or 6.0) as described above, or a substantially similar assay. For example, the invention includes anti-ASIC1 antibodies that exhibit an $IC_{50}$ of less than about 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, or less, when tested in a FLIPR assay at pH 5.5 as described above, or a substantially similar assay.

Other exemplary assay formats that can be used to determine whether an antibody "inhibits acid-induced, ASIC1-mediated ion currents" are illustrated in Examples 5 and 6 herein. In these Examples, automated voltage-clamp, patch-clamp assays are used to measure and/or assess the inhibition of current flux in cells that express ASIC1 at acidic pH in the presence of an anti-ASIC1 antibody, as compared to the current flux observed under equivalent circumstances in the absence of the antibody (e.g., in the presence of a non-specific negative control antibody). An antibody is deemed to "inhibit acid-induced, ASIC1-mediated ion currents" if the antibody, when tested in a voltage-clamp, patch-clamp assay at an antibody concentration of about 1 nM to about 100 nM, at a pH of about 5.0 to about 6.0 (e.g., at pH 5.0, 5.1, 5.2, 5.3, 5.4, 5.5, 5.6, 5.7, 5.8, 5.9, or 6.0), causes at least a 10% current inhibition (e.g., at least about 10%, 15%, 20%, 25%, 30%, 35%, 40%, 45%, 50%, 55%, 60%, 65%, 70%, 75%, 80%, 85%, 90%, 95%, or greater inhibition of current flux; see, e.g., Example 5, Table 6). In some instances, the antibodies of the invention completely inhibit current flux (100% inhibition) at 10 nM or higher (e.g., 100 nM), when tested in a patch-clamp assay format as described above, or a substantially similar assay.

The present invention also includes antibodies that inhibit or reduce pain response(s) in various animal pain models. Exemplary animal pain models useful for characterizing the anti-ASIC1 antibodies of the present invention are illustrated in Examples 7-9, herein. For example, the present invention includes anti-ASIC1 antibodies that attenuate or inhibit pain responses to acid-induced visceral pain in a mouse model. (see, e.g., Example 7). In particular, the present invention includes anti-ASIC1 antibodies that exhibit at least a 20% inhibition of visceral pain responses (e.g., abdominal constrictions in response to an intraperitoneal injection of 0.6% acetic acid) when administered at a dose of about 1 or 10 mg/kg to a mouse model as shown in Example 7, or a substantially similar model. In certain instances, the percent inhibition in pain responses due to the administration of an antibody of the present invention can be as high as about 30%, 35%, 40%, 45%, 50%, or higher when tested in the mouse animal pain model of Example 7, or a substantially similar model. Other animal pain models that can be used to characterize the anti-ASIC antibodies of the present invention include, e.g., the mechanical nociception pain response models of Example 8, the muscle pain models of Example 9, and other similar animal models available in the art. Thus, the present invention includes anti-ASIC1 antibodies capable of attenuating or inhibiting pain responses to noxious mechanical stimuli (see, e.g., Example 8); and/or acidic-saline- or carrageenan-induced muscle hyperalgesia (see, e.g., Example 9), as demonstrated in appropriate animal models as exemplified herein.

Epitope Mapping and Related Technologies

The present invention includes anti-ASIC1 antibodies which interact with one or more amino acids found within the extracellular domain of human ASIC1 (amino acids 63 to 424 of SEQ ID NO:401). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the extracellular domain of ASIC1. Alternatively, the epitope may consist of a plurality of non-contiguous amino acids (or amino acid sequences) located within the extracellular domain of ASIC1.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

The present invention further includes anti-ASIC1 antibodies that bind to the same epitope as any of the specific exemplary antibodies described herein (e.g. H1M6712N, H1M6716N, H1M6718N, H1M7101N, H2M7103N, H3M6713N, H3M6715N, H3M6720N, H3M6721N, H3M6721N2, H3M6726N, H3M6760N, H3M7102N, H3M7118N, H4H6362P, H4H6363P, H4H6364P, H4H6366P, H4H6372P, H4H6374P, H4H6375P, H4H6379P, H4H6380P, H4H6381P, H4H6383P etc.). Likewise, the present invention also includes anti-ASIC1 antibodies that compete for binding to ASIC1 or to cell surface-expressed ASIC1 with any of the specific exemplary antibodies described herein (e.g. H1M6712N, H1M6716N, H1M6718N, H1M7101N, H2M7103N, H3M6713N, H3M6715N, H3M6720N, H3M6721N, H3M6721 N2, H3M6726N, H3M6760N, H3M7102N, H3M7118N, H4H6362P, H4H6363P, H4H6364P, H4H6366P, H4H6372P, H4H6374P, H4H6375P, H4H6379P, H4H6380P, H4H6381P, H4H6383P etc.).

One can easily determine whether an antibody binds to the same epitope as, or competes for binding with, a reference anti-ASIC1 antibody by using routine methods known in the art. For example, to determine if a test antibody binds to the same epitope as a reference anti-ASIC1 antibody of the invention, the reference antibody is allowed to bind to an ASIC1 protein (e.g., cell surface-expressed ASIC1). Next, the ability of a test antibody to bind to the ASIC1 molecule is assessed. If the test antibody is able to bind to ASIC1 following saturation binding with the reference anti-ASIC1 antibody, it can be concluded that the test antibody binds to a different epitope than the reference anti-ASIC1 antibody. On the other hand, if the test antibody is not able to bind to the ASIC1 molecule following saturation binding with the reference anti-ASIC1 antibody, then the test antibody may bind to the same epitope as the epitope bound by the reference anti-ASIC1 antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990: 50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding with a reference anti-ASIC1 antibody, the above-described binding methodology is performed in two orientations: In a first orientation, the reference antibody is allowed to bind to an ASIC1 molecule (e.g., cell surface-expressed ASIC1) under saturating conditions followed by assessment of binding of the test antibody to the ASIC1 molecule. In a second orientation, the test antibody is allowed to bind to an ASIC1 molecule under saturating conditions followed by assessment of binding of the reference antibody to the ASIC1 molecule. If, in both orientations, only the first (saturating) antibody is capable of binding to the ASIC1 molecule, then it is concluded that the test antibody and the reference antibody compete for binding to ASIC1. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

Methods for generating monoclonal antibodies, including fully human monoclonal antibodies are known in the art. Any such known methods can be used in the context of the present invention to make human antibodies that specifically bind to human ASIC1.

Using VELOCIMMUNE™ technology or any other known method for generating monoclonal antibodies, high affinity chimeric antibodies to ASIC1 are initially isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

Bioequivalents

The anti-ASIC1 antibodies and antibody fragments of the present invention encompass proteins having amino acid sequences that vary from those of the described antibodies but that retain the ability to bind human ASIC1. Such variant antibodies and antibody fragments comprise one or more additions, deletions, or substitutions of amino acids when compared to parent sequence, but exhibit biological activity that is essentially equivalent to that of the described antibodies. Likewise, the anti-ASIC1 antibody-encoding DNA sequences of the present invention encompass sequences that comprise one or more additions, deletions, or substitutions of nucleotides when compared to the disclosed sequence, but that encode an anti-ASIC1 antibody or antibody fragment that is essentially bioequivalent to an anti-ASIC1 antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-ASIC1 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-ASIC1 antibody variants comprising amino acid changes which modify the glycosylation characteristics of the antibodies, e.g., mutations which eliminate or remove glycosylation.

Species Selectivity and Species Cross-Reactivity

According to certain embodiments of the invention, the anti-ASIC1 antibodies bind to human ASIC1 but not to ASIC1 from other species. The present invention also includes anti-ASIC1 antibodies that bind to human ASIC1 and to ASIC1 from one or more non-human species. For example, the anti-ASIC1 antibodies of the invention may bind to human ASIC1 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee ASIC1. The present invention also includes anti-ASIC1 antibodies that selectively block acid-induced ion currents through human ASIC1 channels (but not through non-human ASIC1 channels). Alternatively, according to certain embodiments, anti-ASIC1 antibodies are provided that block acid-induced ion currents through human ASIC1 channels as well as through non-human (e.g., mouse, rat, etc.) ASIC1 channels (See, e.g., Example 5, herein).

Immunoconjugates

The invention encompasses anti-ASIC1 monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-ASIC1 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human ASIC1 or a fragment thereof, and the other arm of the immunoglobulin is specific for a second therapeutic target or is conjugated to a therapeutic moiety.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

Therapeutic Formulation and Administration

The invention provides pharmaceutical compositions comprising the anti-ASIC1 antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with ASIC1 activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-ASIC1 antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition of the present invention include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by ASIC1 activity or treatable by blocking or attenuating acid-induced, ASIC1-mediated ion currents in neuronal cells of an individual. Exemplary diseases and disorders that can be treated with the anti-ASIC1 antibodies of the present invention include pain conditions such as nociceptive pain and visceral pain (e.g., pain from inflammatory bowel disease/irritable bowel syndrome, interstitial cystitis, pancreatitis, endometriosis, chronic pelvic pain syndrome, etc.), as well as pain associated with inflammation (e.g., inflammatory muscle pain), polymyositis, post-operative incision (e.g., post-surgical pain), neuropathy (e.g., diabetic neuropathy), sciatica, post-herpetic neuralgia, myofascial pain syndromes (e.g., chronic myofascial pain), arthritis, sickle cell, enteric nerve ischemia, claudication pain, bone fracture, burn, osteoporotic fracture, gout, migraine headache, fibromyalgia, complex regional pain syndrome, acute herpetic pain, etc. The antibodies of the invention may also be used to treat, prevent and/or ameliorate conditions such as, e.g., neurodegenerative diseases (e.g., demyelinating diseases such as multiple sclerosis, amyotrophic lateral sclerosis, etc.), brain injury (e.g., stroke, traumatic brain injury, brain acidosis), neurological disorders (e.g., seizures, seizure disorders), and psychiatric diseases (e.g., depression, anxiety disorders, post-traumatic stress disorder, panic disorder, etc.).

The anti-ASIC1 antibodies of the present invention are also useful for treating or preventing cancer-associated pain. "Cancer-associated pain" includes, e.g., bone cancer pain, including pain from cancer that has metastasized to bone (e.g., breast cancer, prostate cancer, lung cancer, sarcoma, kidney cancer, multiple myeloma, etc.). "Cancer-associated pain" also includes pain more generally associated with cancerous conditions such as, e.g., renal cell carcinoma, pancreatic carcinoma, breast cancer, head and neck cancer, prostate cancer, malignant gliomas, osteosarcoma, colorectal cancer, gastric cancer, malignant mesothelioma, multiple myeloma, ovarian cancer, small cell lung cancer, non-small cell lung cancer, synovial sarcoma, thyroid cancer, or melanoma. The anti-ASIC1 antibodies of the present invention are also useful for treating or preventing pain caused by or associated with cancer therapy or anti-cancer medical treatments, e.g., chemotherapy-induced neuropathic pain such as pain caused by or associated with treatment with paclitaxel (Taxol™), docetaxel (Taxotere®); nitrosourea, cyclophosphamide, doxorubicin, epirubicin, 5-fluorouracil, topotecan, irinotecan, carmustine, estramustine, and platinum-based chemotherapeutic compounds, such as cisplatin, carboplatin, and iproplatin.

Combination Therapies

The present invention includes therapeutic administration regimens which comprise administering an anti-ASIC1 antibody of the present invention in combination with at least one additional therapeutically active component. Non-limiting examples of such additional therapeutically active components include other ASIC inhibitors such as, e.g., a second anti-ASIC1 antibody, an antibody directed against a different ASIC component (e.g., anti-ASIC2 antibody, anti-ASIC3 antibody, anti-ASIC4 antibody, etc.), a peptide ASIC inhibitor (e.g., psalmotoxin-1 [PcTx1], APETx2, etc.), and/or a small molecule ASIC inhibitor (e.g., amiloride, A-317567, etc.).

Other agents that may be beneficially administered in combination with the anti-ASIC1 antibodies of the invention include cytokine inhibitors (including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors), antivirals, antibiotics, analgesics, corticosteroids and/or NSAIDs.

The additional therapeutically active component(s) may be administered prior to, concurrent with, or after the administration of an anti-ASIC1 antibody of the present invention; (for purposes of the present disclosure, such administration regimens are considered the administration of an anti-ASIC1 antibody "in combination with" an additional therapeutically active component).

Diagnostic Uses of the Antibodies

The anti-ASIC1 antibodies of the present invention may also be used to detect and/or measure ASIC1, or ASIC1-expressing cells in a sample, e.g., for diagnostic purposes. For example, an anti-ASIC1 antibody, or fragment thereof, may be used to diagnose a condition or disease characterized by aberrant expression (e.g., over-expression, under-expression, lack of expression, etc.) of ASIC1. Exemplary diagnostic assays for ASIC1 may comprise, e.g., contacting a sample, obtained from a patient, with an anti-ASIC1 antibody of the invention, wherein the anti-ASIC1 antibody is labeled with a detectable label or reporter molecule. Alternatively, an unlabeled anti-ASIC1 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure ASIC1 in a sample include enzyme-linked immunosorbent assay (ELISA), radioimmunoassay (RIA), and fluorescence-activated cell sorting (FACS).

Samples that can be used in ASIC1 diagnostic assays according to the present invention include any tissue or fluid sample obtainable from a patient which contains detectable quantities of ASIC1 protein, or fragments thereof, under normal or pathological conditions. Generally, levels of ASIC1 in a particular sample obtained from a healthy patient (e.g., a patient not afflicted with a disease or condition associated with abnormal ASIC1 levels or activity) will be measured to initially establish a baseline, or standard, level of ASIC1. This baseline level of ASIC1 can then be compared against the levels of ASIC1 measured in samples obtained from individuals suspected of having a ASIC1 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Human ASIC1

To generate anti-human ASIC1 antibodies, a DNA immunization procedure was used in which a DNA plasmid encoding full-length human ASIC1, together with a separate plasmid encoding adjuvant, were injected intradermally into a VELOCIMMUNE® mouse (Regeneron Pharmaceuticals, Inc., Tarrytown, N.Y.). The site of injection was then electroporated to induce host cell transfection of the plasmids. The VELOCIMMUNE® mice used for the immunization comprise DNA encoding human Immunoglobulin heavy and kappa light chain variable regions and lack the endogenous mouse asic1 a gene. The antibody immune response was monitored by a cell binding assay using cells engineered to express human ASIC1. When a desired immune response was achieved, splenocytes were harvested and fused with mouse myeloma cells to preserve their viability and form hybridoma cell lines. The hybridoma cell lines were screened and selected to identify cell lines that produce ASIC1-specific antibodies. Using this technique several anti-ASIC1 chimeric antibodies (i.e., antibodies possessing human variable domains and mouse constant domains) were obtained; exemplary antibodies generated in this manner were designated as follows: H1M6712N, H1M6716N, H1M6718N, H1M7101N, H2M7103N, H3M6713N, H3M6715N, H3M6720N, H3M6721N, H3M6721N2, H3M6726N, H3M6760N, H3M7102N, and H3M7118N.

Anti-ASIC1 antibodies were also isolated directly from antigen-positive B cells without fusion to myeloma cells, as described in US 2007/0280945A1. Using this method, several fully human anti-ASIC1 antibodies (i.e., antibodies possessing human variable domains and human constant domains) were obtained; exemplary antibodies generated in this manner were designated as follows: H4H6362P, H4H6363P, H4H6364P, H4H6366P, H4H6372P, H4H6374P, H4H6375P, H4H6379P, H4H6380P, H4H6381P, and H4H6383P.

Certain biological properties of the exemplary anti-ASIC1 antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-ASIC1 antibodies and their corresponding antibody identifiers.

TABLE 1

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| 6712N | 2 | 4 | 6 | 8 | 10 | 12 | 14 | 16 |
| 6716N | 18 | 20 | 22 | 24 | 26 | 28 | 30 | 32 |
| 6718N | 34 | 36 | 38 | 40 | 42 | 44 | 46 | 48 |
| 7101N | 50 | 52 | 54 | 56 | 58 | 60 | 62 | 64 |
| 7103N | 66 | 68 | 70 | 72 | 74 | 76 | 78 | 80 |
| 6713N | 82 | 84 | 86 | 88 | 90 | 92 | 94 | 96 |
| 6715N | 98 | 100 | 102 | 104 | 106 | 108 | 110 | 112 |
| 6720N | 114 | 116 | 118 | 120 | 122 | 124 | 126 | 128 |
| 6721N | 130 | 132 | 134 | 136 | 138 | 140 | 142 | 144 |
| 6721N2 | 146 | 148 | 150 | 152 | 154 | 156 | 158 | 160 |
| 6726N | 162 | 164 | 166 | 168 | 170 | 172 | 174 | 176 |
| 6760N | 178 | 180 | 182 | 184 | 186 | 188 | 190 | 192 |
| 7102N | 194 | 196 | 198 | 200 | 202 | 204 | 206 | 208 |
| 7118N | 210 | 212 | 214 | 216 | 218 | 220 | 222 | 224 |
| 6362P | 226 | 228 | 230 | 232 | 234 | 236 | 238 | 240 |
| 6363P | 242 | 244 | 246 | 248 | 250 | 252 | 254 | 256 |
| 6364P | 258 | 260 | 262 | 264 | 266 | 268 | 270 | 272 |
| 6366P | 274 | 276 | 278 | 280 | 282 | 284 | 286 | 288 |
| 6372P | 290 | 292 | 294 | 296 | 298 | 300 | 302 | 304 |
| 6374P | 306 | 308 | 310 | 312 | 314 | 316 | 318 | 320 |
| 6375P | 322 | 324 | 326 | 328 | 330 | 332 | 334 | 336 |
| 6379P | 338 | 340 | 342 | 344 | 346 | 348 | 350 | 352 |
| 6380P | 354 | 356 | 358 | 360 | 362 | 364 | 366 | 368 |
| 6381P | 370 | 372 | 374 | 376 | 378 | 380 | 382 | 384 |
| 6383P | 386 | 388 | 390 | 392 | 394 | 396 | 398 | 400 |

Antibodies are typically referred to herein according to the following nomenclature: Fc prefix (e.g. "H4H", "H1M", "H2M"), followed by a numerical identifier (e.g. "6712" or "6362" as shown in Table 1), followed by a "P" or "N" suffix. Thus, according to this nomenclature, an antibody may be referred to herein as, e.g., "H1M6712N" or "H4H6362P". The H4H, H1M, and H3M prefixes on the antibody designations used herein indicate the particular Fc region of the antibody. For example, an "H1M" antibody has a mouse IgG1 Fc, whereas an "H4H" antibody has a human IgG4 Fc. As will be appreciated by a person of ordinary skill in the art, an H1M or H3M antibody can be converted to an H4H antibody, and vice versa, but in any event, the variable domains (including the CDRs)—which are indicated by the numerical identifiers shown in Table 1—will remain the same.

Example 3

Antibody Binding to Cells Expressing Full-Length Human or Mouse ASIC1

To further characterize anti-ASIC1 antibodies, their ability to bind either (a) a mouse fibroblast 3T3 cell line stably transfected to overexpress full length human ASIC1 (3T3/hASIC1; amino acids 1-528 of NCBI accession number NP_001086.2 [SEQ ID NO:401]), (b) a 3T3 cell line stably transfected to over express full length mouse ASIC1a (3T3/mASIC1a; amino acids 1-526 of NCBI accession number NP_033727), or (c) a ND7 cell line (ECACC, #92090903) that is a fusion cell line of mouse neuroblastoma and rat dorsal root ganglia that endogenously expresses rat ASIC1, was determined using flow cytometry (FACS). ND7 cells were differentiated by replacing the culture media with low-serum media (0.5% FBS) containing 1 mM dibutyryl-cAMP (Cat. No. sc-201567A, Santa Cruz Biotechnology, Inc., Santa Cruz, Calif.). FACS binding was tested for some antibodies on both undifferentiated ND7 cells and differentiated ND7 cells.

To perform the FACS binding experiments, adherent cells were collected using 1 mM EDTA in PBS, then washed, and re-suspended in cold PBS containing 5% FBS. For each binding experiment, each anti-ASIC1 antibody (at final concentrations of 10 nM of purified antibodies or 3.3 nM for antibody supernatants for binding to 3T3/hASIC1 cells and 5nM for binding to 3T3/mASIC1a or ND7 cells) was added to 250,000 cells in 500 µL of PBS with 5% FBS. After incubation for 20 minutes at room temperature, a secondary antibody which recognizes human Fc (Cat. No. 109-136-098, Jackson ImmunoResearch Laboratories, Inc., West Grove, Pa.) or mouse Fc (Cat. No. 550826, BD Biosciences, San Jose, Calif.) and is conjugated to allophycocyanin, was then added to the cell mixture at a final concentration of 13.3 nM. After incubating for 20 minutes on ice, the cells were washed and resuspended in PBS containing 5% FBS, then sorted and analyzed on a flow cytometer (FACSCalibur, BD Biosciences, San Jose, Calif.) to determine relative binding by the candidate antibodies to the tested cell lines. Histograms of cells stained with anti-ASIC1 antibodies were compared with those of cells stained with secondary antibody alone. Percentage of ASIC1 signal over secondary antibody alone was calculated using FlowJo software (Tree Star, Ashland, Oreg.). The samples stained with anti-ASIC1 antibodies were recorded as FACS positive when gated greater than 10%. The samples stained with anti-ASIC1 antibodies were recorded as FACS negative when gated lower than 1%. The samples stained with anti-ASIC1 antibody were recorded as weak when gated between 1%-10%. The binding specificities of the anti-ASIC1 antibodies to 3T3/hASIC1 cells, 3T3/mASIC1a cells and ND7 cells are summarized in Table 2 (ND=not determined).

TABLE 2

Binding Specificity of Anti-ASIC1 Antibodies As Determined by FACS

| Antibody | FACS Binding to 3T3/hASIC1 | FACS Binding to 3T3/mASIC1a | FACS Binding to Undifferentiated ND7 cells | FACS Binding to Differentiated ND7 cells |
|---|---|---|---|---|
| H1M6712N | Positive | ND | ND | ND |
| H3M6721N | Positive | Positive | Negative | ND |
| H1M6718N | Positive | Positive | Positive | Positive |
| H4H6372P | Negative | ND | ND | ND |
| H4H6374P | Negative | ND | ND | ND |
| H4H6375P | Negative | ND | ND | ND |
| H4H6379P | Negative | ND | ND | ND |
| H4H6380P | Negative | ND | ND | ND |
| H4H6381P | Negative | ND | ND | ND |
| H4H6383P | Negative | ND | ND | ND |
| H4H6362P | Negative | ND | ND | ND |
| H4H6363P | Positive | ND | ND | ND |
| H4H6364P | Positive | ND | ND | ND |
| H1M7101N | Positive | Positive | Positive | ND |
| H1M6716N | Positive | ND | ND | ND |
| H3M6726N | Positive | Positive | Positive | Positive |
| H3M6720N | Positive | Negative | Negative | Negative |
| H3M6713N | Positive | ND | ND | ND |
| H3M7102N | Positive | Positive | Positive | ND |
| H3M6760N | Positive | ND | ND | ND |
| H2M7103N | Positive | Positive | Negative | Negative |
| H3M6715N | Positive | ND | ND | ND |
| H3M7118N | Positive | Weak | Weak | Positive |
| H4H6366P | Positive | Positive | Positive | Positive |
| H4H6721N2 | Positive | Positive | Positive | Positive |

Binding affinity of selected antibodies to 3T3/hASIC1 cells was further examined by FACS using multiple antibody concentrations (67 nM, 6.7 nM, 0.67 nM, 67 pM, and 6.7 pM) from which approximate $EC_{50}$ values were calculated. The mean fluorescence intensity (MFI) signal observed for the anti-ASIC1 antibodies was subtracted by the background signal (secondary antibody alone) and plotted as a function of antibody concentration to determine $EC_{50}$ values using GraphPad Prism (Table 3).

TABLE 3

$EC_{50}$ Values for Select Anti-ASIC1 Antibodies Binding to 3T3/hASIC1 Cells

| Antibody | $EC_{50}$ |
|---|---|
| H1M6712N | <100 pM |
| H3M6721N | 85 pM |
| H1M6718N | 550 pM |
| H4H6363P | 836 pM |
| H3M6713N | 215 pM |
| H3M6715N | 72 pM |
| H1M6716N | 23 pM |
| H3M6720N | 1.1 nM |
| H3M6726N | 2.6 nM |
| H3M6760N | 853 pM |
| H1M7101N | 720 pM |
| H3M7102N | 5.4 nM |
| H3M7118N | >67 nM |
| H2M7103N | 1.7 nM |
| H4H6364P | 1.5 nM |
| H4H6366P | 1.0 nM |
| H4H6721N2 | 1.7 nM |

As shown in Table 2, seventeen of the 25 antibodies tested demonstrated specific binding to 3T3/hASIC1 cell line; eight of 10 antibodies tested demonstrated positive binding to the 3T3/mASIC1a cells; six of 10 antibodies tested demonstrated positive binding to the undifferentiated ND7 cell line; and five of 7 antibodies tested demonstrated positive binding to the differentiated ND7 cell line. Notably, one antibody (H3M7118N) demonstrated weak binding to both 3T3/mASIC1a and undifferentiated ND7 cell lines but positive binding to 3T3/hASIC1 cells. As shown in Table 3, the anti-ASIC1 antibodies tested at multiple antibody concentrations demonstrated high affinity FACS binding with approximate $EC_{50}$ values as low as 23 pM for binding to the 3T3/hASIC1 cells.

Example 4

Anti-ASIC1 Antibodies Block Acid-Mediated Cell Signaling in a Cellular Calcium Flux Assay To characterize functional blocking of acid-mediated cell signaling by anti-ASIC1 antibodies, an assay that measures cellular calcium flux was implemented using a cell line, HEK293 CL:1F10 (1F10), that was transiently transfected to express human ASIC1 (amino acids 1-528 of NCBI accession number NP_0010862.2 [SEQ ID NO:401]). This cell line was created from the parental line HEK293/D9 that was stably transfected to express human Par2. Transfected cells were incubated at 37° C., 5% $CO_2$ for 2 days before replating into a 96-well black, clear bottom assay plate at a concentration of 100,000 cells per well. Cells were allowed to adhere to the plate at room temperature for 20 minutes then incubated overnight at 37° C., 5% $CO_2$.

The Fluo-4 NW calcium assay kit (Invitrogen, #F36206) was used to determine the level of intracellular calcium flux within cells activated by low pH buffers. Assay buffer was prepared according to the manufacturer's specifications. Fifty µL of probenecid (77 µg/µL) was added to 5 mL of buffer C (2× HBSS), which was then added to component A (Fluo-4 dye). Anti-ASIC1 antibodies were diluted in the Fluo-4 dye to a concentration of 250 nM for the single point blocking assay. The antibodies that blocked calcium flux stimulated by low pH buffers were further characterized in this assay using multiple antibody concentrations. Anti-ASIC1 antibodies were diluted to a concentration of 250 nM in the dye and an 8 point 1:3 dilution series (ranging from 250 to 0.1 nM) was used to determine the blocking $IC_{50}$ of each antibody. The cell culture media was removed from the assay plate containing cells and 50 µL of the Fluo-4 dye containing anti-ASIC1 antibody was then added. The plates were incubated at 37° C., 5% $CO_2$ for 1 hour before reading by FLIPR Tetra (Molecular Devices).

The pH of buffer C was adjusted to pH 5.0 or pH 5.5 and added to a reservoir plate before addition to the cells. The FLIPR Tetra then added 50 µL of the low pH buffer from the reservoir plate to the cells in the assay plate at a speed of 50 µl per second. The calcium signal produced by each well for 10 seconds prior to buffer addition (pre-read) and for 100 seconds after buffer addition was measured by FLIPR Tetra using an excitation wavelength setting of 470-490 nm and an emission wavelength setting of 515-575 nm. The difference between the maximum observed value obtained after buffer addition and the minimum value during the entire assay including both the pre-read and after buffer addition was calculated and graphed using Graph Pad Prism. Results are shown in Tables 4 and 5.

TABLE 4

Blocking of Acid-Mediated Cellular Calcium Flux by
250 nM of Anti-ASIC1 Antibodies at pH 5.5 and 5.0
FLIPR

| | 250 nM Single Point | |
|---|---|---|
| Antibody | pH 5.5 | pH 5.0 |
| H1M6712N | Weak | Neg |
| H3M6721N | Pos | Pos |
| H1M6718N | Pos | Pos |
| H1M7101N | Neg | Neg |
| H1M6716N | Weak | Weak |
| H3M6726N | Neg | Neg |
| H3M6720N | Neg | Neg |
| H3M6713N | Weak | Weak |
| H3M7102N | Neg | Neg |
| H3M6760N | Pos | Weak |
| H2M7103N | Neg | Neg |
| H3M6715N | Weak | Weak |
| H3M7118N | Neg | Neg |
| H4H6372P | Weak | Neg |
| H4H6374P | Weak | Neg |
| H4H6375P | Weak | Weak |
| H4H6379P | Neg | Neg |
| H4H6380P | Weak | Neg |
| H4H6381P | Weak | Neg |
| H4H6383P | Neg | Neg |
| H4H6362P | Neg | Neg |
| H4H6363P | Neg | Neg |
| H4H6364P | Neg | Neg |
| H4H6366P | Neg | Neg |

TABLE 5

Dose dependent blocking of acid-mediated cellular calcium
flux by anti-ASIC1 antibodies at pH 5.5 and 5.0

| | FLIPR Dose Curve | | | |
|---|---|---|---|---|
| Antibody | pH 5.5% Block | pH 5.5 $IC_{50}$ nM | pH 5.0% Block | pH 5.0 $IC_{50}$ nM |
| H1M6712N | 64% | 6 nM | 10%, No dose dep. | No dose dep. |
| H3M6721N | 44% | 0.3 nM | 25% | IC* |
| H1M6718N | 78% | 0.6 nM | 48% | IC* |
| H3M6713N | 63% | 0.2 nM | 23%, No dose dep. | No dose dep. |
| H3M6715N | 39% | 0.1 nM | 10%, No dose dep. | No dose dep. |
| H1M6716N | 37% | 1.1 nM | 25%, No dose dep. | No dose dep. |
| H3M6760N | 71% | 0.9 nM | 56% | 1 nM |
| H4H6375P | 27% | 0.1 nM | 10%, No dose dep. | No dose dep. |
| H4H6380P | Neg | Neg | Neg | Neg |
| H4H6381P | Neg | Neg | Neg | Neg |

As shown in Table 4, two of the 24 antibodies, H3M6721N and H1M6718N, exhibited greater than 30% blockade of the calcium flux (Pos) at the single concentration of 250 nM at both pH 5.5 and pH 5.0, and one antibody (H3M6760N) exhibited greater than 30% block at only pH 5.5. Twelve of the 24 antibodies at pH 5.5 and 17 of the 24 antibodies at pH 5.0 tested at the single concentration of 250 nM did not exhibit measurable blockade (Neg). Nine of the 24 antibodies at pH 5.5, and 5 of the 24 antibodies at pH 5.0, tested at the single concentration of 250 nM exhibited a reduction in calcium flux between 10-30% (Weak).

As shown in Table 5, eight of the 10 antibodies tested for dose dependent blocking at pH 5.5 exhibited a percent blockade of the calcium flux ranging from 27% to 78% and $IC_{50}$ values ranging from 0.1 nM to 6 nM. Two of the antibodies tested for dose dependent calcium flux blockade at pH 5.5, H4H6380P and H4H6381P, exhibited no measurable blockade. Two of the 10 antibodies tested for dose dependent blocking at pH 5.0, H3M6721N and H1M6718N, exhibited a 25% and 48% blockade of the calcium flux, respectively, but $IC_{50}$ values could not be determined (IC*) despite showing dose dependence. One of the 10 antibodies tested for dose dependent blocking at pH 5.0, H3M6760N, exhibited a 56% blockade of the calcium flux and an $IC_{50}$ value of 1 nM. Five of the 10 antibodies tested for dose dependent calcium flux blockade at pH 5.0 exhibited no dose dependent blockade but blocked between 10% and 25% of the calcium flux at each of the antibody concentrations tested. Two of the 10 antibodies tested for dose dependent blocking at pH 5.0, H4H6380P and H4H6381P, exhibited no measurable blockade.

Example 5

Anti-ASIC1 Antibodies Block Acid-Induced ASIC1 Ion Currents in an Automated Voltage-Clamp Patch-Clamp Assay [Q-Patch]

The Q-Patch (Sophion Bioscience, Inc., Ballerup, Denmark), a microchip-based automated patch-clamp system, was used to determine the ability of the anti-ASIC1 antibodies to inhibit either the human ASIC1 current in a stably transfected HEK293 cell line expressing the full length human ASIC1 channel (HEK/hASIC1; amino acids 1-528 of NCBI accession number NP_001086.2) or the mouse ASIC1a current in a stably transfected 3T3 cell line expressing the full-length mouse ASIC1a channel (3T3/mASIC1a; amino acids 1-526 of NCBI accession number NP_033727).

HEK/hASIC1 cells were cultured in DMEM high glucose media, 10% fetal bovine serum (FBS), 1% non-essential amino acids and 500 μg/mL Geneticin® (Invitrogen, #10131). 3T3/mASIC1a cells were cultured in DMEM high glucose media, 10% FBS, 1% penicillin/streptomycin/glutamine (Invitrogen, #10378-016), and 400 ug/mL Geneticin®. On the day of the recordings, cells were harvested with Detachin cell detachment solution (Genlantis, San Diego, Calif., #T100100), centrifuged and resuspended in 1.4 mL serum free solution [CHO-SFM-II media (Invitrogen, #31033), HEPES 25 mM and penicillin/streptomycin 100 units/mL]. The cell suspension was then incubated on a shaker for 40 minutes at room temperature (RT). Two or three anti-ASIC1 antibodies and a control antibody were run in parallel in one experiment. Thus, at the end of the incubation, the cell suspension was dispensed into 4 tubes (approximately $5 \times 10^5$ cells in 300 μL/tube) and the antibodies were diluted to a final concentration of 100 nM directly in the tubes for single point experiments, or at a range of concentrations for dose response experiments and then incubated on a shaker for 20 minutes at RT. At the end of the incubation, cells were loaded on the Q-Patch.

Cells were first perfused with a buffer at pH 7.4 (NaCl 140 mM, KCl 4 mM, $MgCl_2$ 1 mM, $CaCl_2$ 2 mM, glucose 5 mM and HEPES 10 mM) containing 0.2% (w/v) bovine serum albumin (extracellular buffer) and the antibody of interest at a final concentration of 100 nM for single point experiments, or at a range of concentrations for dose response experiments, was added and allowed to incubate for about 3 minutes. Then, the human ASIC1 current was elicited for one second by the addition of the extracellular buffer adjusted to pH 6.0 while cells were maintained at a holding potential of −80 mV. Thirty μM of amiloride was added after each recording on the Q-Patch to demonstrate that the cells were responsive through the duration of the assay. The composition of the intracellular recording solution was CsCl 140 mM, $MgCl_2$ 4 mM, EGTA 10 mM and HEPES 10 mM; adjusted to pH 7.3 with CsOH.

All anti-ASIC1 antibodies were tested in quadruplicate in parallel with the control irrelevant antibody. Channel blocking was measured as percent inhibition of current flux in the presence of anti-ASIC1 antibody relative to current flux in the presence of the control irrelevant antibody, averaged over multiple blocking experiments. Results are summarized in Table 6.

TABLE 6

Percent Inhibition of Acid-Induced Human ASIC1 Currents by Anti-ASIC1 Antibodies at 100 nM

| Antibody | Number of wells tested | Antibody concentration (nM) | Current inhibition (%) |
|---|---|---|---|
| H1M6712N | 10 | 100 | 0 |
| H3M6715N | 7 | 100 | 30 |
| H3M6720N | 7 | 100 | 82 |
| H3M6726N | 3 | 100 | 85 |
| H3M6721N | 14 | 100 | 100 |
| H1M6718N | 8 | 100 | 100 |
| H4H6372P | 4 | 100 | 0 |
| H4H6374P | 8 | 100 | 0 |
| H4H6375P | 5 | 100 | 0 |
| H4H6379P | 4 | 100 | 30 |
| H4H6380P | 5 | 100 | 0 |
| H4H6381P | 6 | 100 | 25 |
| H4H6383P | 4 | 100 | 15 |
| H4H6362P | 4 | 100 | 29 |
| H4H6363P | 4 | 100 | 0 |
| H4H6364P | 2 | 100 | 0 |
| H4H6366P | 8 | 100 | 72 |
| H3M7099N | 4 | 100 | 25 |
| H1M7101N | 4 | 100 | 97 |
| H3M7102N | 3 | 100 | 100 |
| H2bM7103N | 7 | 100 | 92 |
| H3M7104N | 7 | 100 | 35 |
| H1M7117N | 4 | 100 | 30 |

As shown in Table 6, seventeen of the 23 antibodies tested at 100 nM on the Q-Patch demonstrated functional inhibition of human ASIC1 current with 9 of the 17 antibodies showing a blockade greater than 70%. Eleven antibodies (H1M6718N, H3M6720N, H3M6721N, H3M6726N, H4H6366P, H1M7101N, H3M7102N, H2bM7103N, H3M7118N, H4H6718N, and H4H6721N2) were further tested for their ability to inhibit the human ASIC1 current at different concentrations on the Q-Patch, and nine antibodies (H4H6718N, H3M6720N, H3M6721N, H1M7101N, H3M7102N, H2bM7103N, H3M6726N, H4H6366P, and H3M7118N) were tested for their ability to inhibit the mouse ASIC1 current. The percentage of blockade observed for these antibodies is summarized in Table 7 (human ASIC1) and Table 8 (mouse ASIC1).

TABLE 7

Percent Inhibition of Acid-Induced Human ASIC1 Currents by Anti-ASIC1 Antibodies at Various Antibody Concentrations

| Antibody | Number of wells tested | Antibody concentration (nM) | % Current inhibition ± SEM |
|---|---|---|---|
| H1M6718N | 4 | 100 | 100 ± 0 |
|  | 18 | 10 | 99 ± 1 |
|  | 13 | 1 | 63 ± 13 |
|  | 8 | 0.1 | 0 ± 0 |
| H3M6720N | 13 | 100 | 83 ± 9 |
|  | 8 | 50 | 88 ± 6 |
|  | 3 | 10 | 70 |
|  | 4 | 1 | 0 |

TABLE 7-continued

Percent Inhibition of Acid-Induced Human ASIC1 Currents by Anti-ASIC1 Antibodies at Various Antibody Concentrations

| Antibody | Number of wells tested | Antibody concentration (nM) | % Current inhibition ± SEM |
|---|---|---|---|
| H3M6721N | 14 | 100 | 100 |
|  | 8 | 50 | 100 |
|  | 11 | 10 | 75 ± 10 |
|  | 6 | 1 | 30 |
| H3M6726N | 14 | 100 | 77 ± 3 |
|  | 12 | 10 | 30 ± 11 |
|  | 7 | 1 | 15 ± 15 |
| H4H6366P | 7 | 100 | 76 ± 6 |
|  | 6 | 10 | 53 ± 8 |
|  | 7 | 1 | 38 ± 15 |
| H1M7101N | 4 | 100 | 97 |
|  | 10 | 10 | 99 ± 0.7 |
|  | 4 | 5 | 96 |
|  | 10 | 1 | 57 ± 18 |
|  | 4 | 0.1 | 7 |
| H3M7102N | 4 | 100 | 99 |
|  | 8 | 10 | 96 ± 1 |
|  | 3 | 5 | 35 |
|  | 10 | 1 | 0 ± 0 |
| H2bM7103N | 7 | 100 | 96 ± 3 |
|  | 3 | 50 | 96 |
|  | 5 | 10 | 61 ± 15 |
|  | 4 | 1 | 0 |
| H3M7118N | 2 | 100 | 99 |
|  | 2 | 10 | 89 |
|  | 2 | 1 | 30 |
| H4H6718N | 7 | 10 | 100 |
|  | 6 | 5 | 98 ± 2 |
|  | 3 | 1 | 97 |
|  | 8 | 0.6 | 66 ± 6 |
|  | 4 | 0.3 | 54 |
|  | 4 | 0.1 | 12 |
| H4H6721N2 | 7 | 10 | 95 ± 2 |
|  | 13 | 5 | 93 ± 1 |
|  | 7 | 1 | 59 ± 10 |
|  | 8 | 0.6 | 32.7 ± 0.1 |
|  | 3 | 0.3 | 40 |
|  | 4 | 0.1 | 1 |

TABLE 8

Percent Inhibition of Acid-Induced Mouse ASIC1a Currents by Anti-ASIC1 Antibodies at Various Antibody Concentrations

| Antibody | Number of wells tested | Antibody concentration (nM) | % Current inhibition ± SEM |
|---|---|---|---|
| H4H6718N | 10 | 10 | 90 |
|  | 4 | 5 | 98 |
|  | 3 | 2 | 96 |
|  | 3 | 1 | 71 |
|  | 9 | 0.3 | 36 ± 3 |
|  | 2 | 0.1 | 20 |
| H3M6720N | 4 | 100 | 83 |
|  | 4 | 50 | 83 |
|  | 3 | 10 | 46 |
|  | 4 | 5 | 19 |
|  | 10 | 1 | 12 ± 3 |
|  | 6 | 0.1 | 21 ± 8 |
| H3M6721N | 4 | 100 | 91 |
|  | 3 | 10 | 57 |
|  | 4 | 1 | 0 |
| H4H6721N2 | 8 | 25 | 99 ± 1 |
|  | 7 | 10 | 62 |
| H1M7101N | 4 | 100 | 90 |
| H3M7102N | 4 | 100 | 100 |
| H2bM7103N | 8 | 100 | 67 ± 2 |
|  | 3 | 50 | 77 |
|  | 3 | 10 | 30 |
|  | 2 | 5 | 32 |

TABLE 8-continued

Percent Inhibition of Acid-Induced Mouse ASIC1a Currents by Anti-ASIC1 Antibodies at Various Antibody Concentrations

| Antibody | Number of wells tested | Antibody concentration (nM) | % Current inhibition ± SEM |
|---|---|---|---|
|  | 10 | 1 | 33 ± 5 |
|  | 7 | 0.1 | 3 ± 1 |
| H3M6726N | 4 | 100 | 51 |
|  | 3 | 50 | 38 |
|  | 3 | 5 | 23 |
|  | 4 | 1 | 3 |
| H4H6366P | 1 | 100 | 46 |
|  | 4 | 10 | 30 |
|  | 3 | 5 | 28 |
|  | 4 | 1 | 10 |
| H3M7118N | 7 | 100 | 92 ± 3 |
|  | 3 | 50 | 87 |
|  | 8 | 10 | 36 ± 23 |
|  | 4 | 5 | 12 |
|  | 6 | 1 | 6 ± 6 |

As shown in Table 7, one antibody, H3M6726N, blocked the human ASIC1 current with an apparent $IC_{50}$ greater than 10 nM, while six antibodies (H3M6720N, H3M6721N, H4H6366P, H3M7102N, H2bM7103N and H3M7118N) blocked the human ASIC1 current with an apparent $IC_{50}$ of 10 nM or less. Four of the antibodies, H1M6718N, H1M7101N, H4H6718N, and H4H6721N2, blocked the human ASIC1 current with an apparent $IC_{50}$ less than 1 nM.

As shown in Table 8, six of the 10 anti-ASIC1 antibodies (H4H6718N, H3M6721N, H4H6721N2, H1M7101N, H3M7102N and H3M7118N) tested on the mouse ASIC1 expressing cells inhibited 90 to 100% of the mouse ASIC1 current at highest antibody concentration tested, while four antibodies (H3M6720N, H3M6726N, H4H6366P, and H2bM7103N) only inhibited the current by approximately 80% or less. H3M7118N, H2bM7103N, H3M6720N and H3M6721N blocked the mouse ASIC1 current with an apparent $IC_{50}$ less than 25 nM. H4H6718N blocked the human ASIC1 current with an apparent $IC_{50}$ less than 1 nM.

The Q-Patch was also used to determine the ability of the anti-ASIC1 antibody H4H6718N to inhibit the ASIC1 current in the ND7/23 cell line (ECACC, #92090903), which is a fusion cell line of mouse neuroblastoma and rat dorsal root ganglia that endogenously expresses rat ASIC1.

ND7/23 cells were cultured in DMEM high glucose media containing 10% FBS, 2 mM glutamine, 1% penicillin-streptomycin (Invitrogen, #10378-016). The day after seeding, ND7/23 cells were differentiated by replacing the culture media with low-serum media (0.5% FBS) containing 1 mM dibutyryl-cAMP (Santa Cruz, #sc-201567A). On the day of the recordings, cells were harvested using StemPro Accutase cell dissociation reagent (Invitrogen, #A11105-01), centrifuged, and resuspended in 1 mL of extracellular buffer solution. The cell suspension was then loaded on the Q-Patch.

Cells were first perfused with an extracellular buffer solution at pH 7.4 (NaCl 140 mM, KCl 4 mM, $MgCl_2$ 1 mM, $CaCl_2$ 2 mM, glucose 5 mM and HEPES 10 mM, adjusted to pH 7.4 with NaOH) containing 0.2% (w/v) bovine serum albumin for 6 minutes to stabilize the patch. The rat ASIC1 current was then elicited for one second by the addition of the extracellular buffer, which was adjusted to pH 6.0, while the cells were maintained at a holding potential of −80 mV. The rat ASIC1 current was elicited 2 times in extracellular buffer at pH 6 and then 2 additional times in the same extracellular buffer containing either 10 nM of an isotype control antibody or 10 nM of the anti-ASIC1 antibody (H4H6718N, H3M6720N, H2bM7103N, H3M6726N, H4H6366P and H3M7118N). After the anti-ASIC1 antibody recordings 10 nM of the selective ASIC1 antagonist PcTx1 (Alomone Labs, #STP-200) was added to the cells to evaluate the contribution of ASIC1-specific currents to the current elicited by extracellular buffer at pH 6. The composition of the intracellular recording solution was CsF 120 mM, NaCl 15 mM, EGTA 10 mM and HEPES 10 mM; adjusted to pH 7.3 with CsOH.

Channel blocking was measured as percent inhibition of current flux in the presence of anti-ASIC1 antibody relative to the current flux measured before the application of the antibody and was compared to the percent inhibition of current flux in the presence of PcTx1, which was used to define the maximum ASIC1-specific current blockade. Results are shown in Table 9.

TABLE 9

Percent Inhibition of Acid-Induced Rat ASIC1a Currents in ND7 Cells by Anti-ASIC1 Antibodies

| Antibody | Number of Wells Tested | Antibody Concentration (nM) | Percent Current Inhibition ± SEM |
|---|---|---|---|
| H4H6718N | 9 | 10 | 100 |
| H3M6720N | 4 | 10 | 43 ± 15 |
| H2b7103N | 5 | 10 | 26 ± 14 |
| H3M6726N | 5 | 10 | 7 ± 6 |
| H4H6366P | 3 | 10 | 36 ± 20 |
| H3M7118N | 10 | 10 | 65 ± 11 |
| Isotype Control | 21 | 10 | 15 ± 3 |

As shown in Table 9, H4H6718N demonstrated a 100% inhibition of the rat ASIC1 currents in differentiated ND7/23 cells at a concentration of 10 nM (n=9) while H3M6720N and H3M7118N inhibited the current by approximately 43% and 65%, respectively. Three antibodies (H2bM7103N, H3M6726N and H4H6366P) did not demonstrate significant inhibition of rat ASIC1 currents at 10 nM in these experiments.

Example 6

An Anti-ASIC1 Antibody Blocks Acid-Induced ASIC1 Ion Currents in an Automated Voltage-Clamp Patch-Clamp Assay [Port-A-Patch]

The Port-a-Patch (Nanion Technologies Inc., North Brunswick, N.J.), a microchip-based automated patch-clamp system, was used to determine the half maximal inhibitory concentration ($IC_{50}$) of the anti-ASIC1 antibody H1M6718N needed to inhibit the human ASIC1 current in a stably transfected HEK293 cell line expressing the full length human ASIC1 channel (HEK/hASIC1; amino acids 1-528 of NCBI accession number NP_001086.2).

HEK/hASIC1 cells were cultured in DMEM high glucose media, 10% fetal bovine serum, 1% non-essential amino acids and 500 μg/mL Geneticin® (Invitrogen, #10131). On the day of the recordings, cells were harvested with Detachin cell detachment solution (Genlantis, San Diego, Calif., #T100100), centrifuged, and resuspended in 500 μL extracellular buffer solution (NaCl 140 mM, KCl 4 mM, $MgCl_2$ 1 mM, $CaCl_2$ 2 mM, glucose 5 mM and HEPES 10 mM, pH 7.4 with NaOH). The cell suspension was then loaded on the Port-a-Patch.

Cells were first perfused with extracellular buffer at pH 7.4 containing 0.1% (w/v) bovine serum albumin for about 5 minutes to stabilize the patch. Then, the human ASIC1 current was elicited for three seconds by the addition of the extracellular buffer adjusted to pH 6.0 while cells were maintained at a holding potential of −80 mV. The human ASIC1 current was elicited 3 times (2 minutes apart) in pH 6.0 extracellular buffer and 3 times in pH 6.0 extracellular buffer containing either 100 nM of an isotype control antibody or 10, 3, 1, 0.8 or 0.6 nM of the anti-ASIC1 antibody H1M6718N. Thirty pM of amiloride in pH 6 extracellular buffer was added after completing the pH-stimulated measurements to demonstrate that the cells were responsive through the duration of the assay. The composition of the intracellular recording solution was CsF 120 mM, $NaCl_2$ 15 mM, EGTA 10 mM and HEPES 10 mM; adjusted to pH 7.3 with CsOH.

Channel blocking was measured as percent inhibition of current flux in the presence of anti-ASIC1 antibody relative to current flux before application of the antibody. This was averaged over multiple blocking experiments.

The percentage of blockade of the human ASIC1 current by 10, 3, 1, 0.8 and 0.6 nM of H1M6718N is summarized in Table 10.

TABLE 10

Percent Inhibition of Human ASIC1 Current by An Anti-ASIC1 Antibody At Various Concentrations

| Antibody | Number of wells tested | Antibody concentration (nM) | % Current Inhibition ± SEM |
|---|---|---|---|
| H1M6718N | 3 | 10 | 94 ± 1 |
| | 3 | 3 | 86 ± 7 |
| | 4 | 1 | 76 ± 6 |
| | 3 | 0.8 | 33 ± 6 |
| | 4 | 0.6 | 17 ± 9 |
| Isotype control | 3 | 100 | 0 |

H1M6718N showed a dose-dependent inhibition of human ASIC1 current with a calculated $IC_{50}$ of 860 pM, while the isotype control antibody showed no inhibition of the current at a concentration of 100 nM.

Example 7

An Anti-ASIC1 Antibody Reduces Visceral Pain Responses in a Mouse Model

In this example, the ability of the anti-ASIC1 antibody H1M6718N to attenuate visceral pain in a model of acetic acid induced abdominal constrictions was assessed. Wild-type C57BL/6 mice from Jackson Laboratory (Bar Harbor, Me.) were used in this experiment. Separate cohorts of mice (n=10) received 10 mg/kg (s.c.) of an isotype control mAb or 1 or 10 mg/kg (s.c.) of H1M6718N. Twenty-four hours after antibody dosing all cohorts received an intraperitoneal injection of 0.6% acetic acid, which produced stereotypical abdominal stretching behaviors (e.g. constrictions) that were counted by a blinded observer for up to 30 minutes post-injection. The results of this experiment, expressed in terms of the percent change in the total number of abdominal constrictions, are shown in Table 11 (all data are represented as mean±SEM).

TABLE 11

Effect of Anti-ASIC1 Antibody on Abdominal Constrictions Induced by Acetic Acid Injection

| Dose of H1M6718N | Percent Change in Abdominal Constrictions Relative to Control |
|---|---|
| 1 | −32.06 ± 15.8 |
| 10 | −46.57 ± 19.3 |

This example demonstrates that anti-ASIC1 antibody (H1M6718N), which was shown to potently block acid-induced ASIC1 ion currents (see Examples 4 through 6), was effective in alleviating acid-induced visceral pain responses in a mouse model.

Example 8

An Anti-ASIC1 Antibody Produces Analgesia to a Noxious Mechanical Stimulus in a Mouse Model In this Example, the ability of an anti-ASIC1 antibody (H1M6718N) to produce analgesia in response to noxious pinch/pressure stimuli was assessed.

Wild-type C57BL/6 mice from Jackson Laboratory (Bar Harbor, Me.) were used in this experiment. Separate cohorts of mice received 1, 10, or 40 mg/kg (s.c.) of H1M6718N, or 10 mg/kg (s.c) of an isotype control antibody. Twenty-four hours after antibody dosing, separate cohorts (n=10) were tested for their mechanical nociception thresholds, which were measured by the withdrawal threshold to a pinch of the gastrocnemius muscle or the tail (Model #2455, IITC Life Science, Woodland Hills, Calif.). Mechanical nociception in the tail was measured in mice treated with 1 mg/kg and 10 mg/kg of H1M6718N in addition to those treated with an isotype control. Mechanical nociception in the gastrocnemius muscle was measured in mice treated with 10 mg/kg and 40 mg/kg of H1M6718N in addition to those treated with an isotype control. The results of these experiments, expressed as withdrawal threshold to the pinch in grams (mean±SEM for each cohort of mice), are shown in FIG. 1, panels A and B.

For both experiments, H1M6718N treatment resulted in a significant increase in the withdrawal threshold at the highest antibody dose tested (10 mg/kg in tail experiment [FIG. 1, panel A] and 40 mg/kg in the gastrocnemius muscle experiment [FIG. 1, panel B]) compared with the isotype control as determined by ANOVA (p=0.0015 for the tail and 0.0228 for the gastrocnemius muscle) and by Bonferonni post-hoc test (*=p<0.05).

Example 9

An Anti-ASIC1 Antibody Attenuates Muscle Pain in Mouse Models

In this Example, the ability of anti-ASIC1 antibodies H1M6718N and H4H6721N2 to attenuate muscle pain resulting from injection of either acidic saline (pH 5.5) or 3% carrageenan was assessed. Wild-type C57BL/6 mice from Jackson Laboratory (Bar Harbor, Me.) were used in these experiments.

In a first experiment, separate cohorts of mice received 10 mg/kg (s.c) of an isotype control antibody or 10 mg/kg (s.c.) of H1M6718N. Twenty-four hours after antibody dosing all mice received an intramuscular injection of acidic saline (pH 5.5) into the gastrocnemius muscle, which produced robust primary mechanical hyperalgesia of several days as measured by the withdrawal threshold to a pinch of the muscle (Model #2455, IITC Life Science, Woodland Hills, Calif.). Results are shown in FIG. 2.

In a second experiment, separate cohorts of mice received 10 mg/kg (s.c.) of an isotype control mAb; 10, or 40 mg/kg (s.c.) of H1M6718N; or 10 or 30 mg/kg (s.c.) of H4H6721N2. Twenty-four hours after antibody dosing all mice received an intramuscular injection of 3% carrageenan (w/v) into the gastrocnemius muscle, which produced robust primary mechanical hyperalgesia of several days as measured by the withdrawal threshold to a pinch of the muscle (Model #2455, IITC Life Science, Woodland Hills, Calif.). Results are shown in FIG. 3A (10 and 40 mg/kg H1M6718N) and 3B (10 and 30 mg/kg H4H6721N2).

Figure 2:
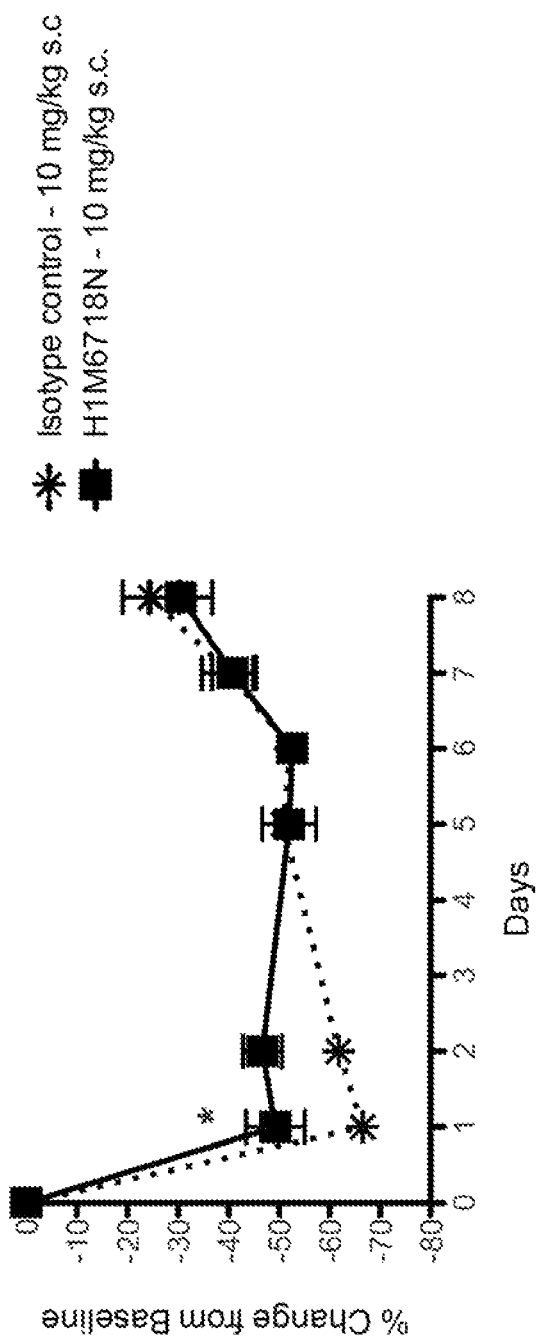
FIG. 2 shows the percent change in the withdrawal threshold from baseline in acidic saline-induced muscle hyperalgesia in mice treated with an anti-ASIC1 antibody (H1M6718N) or isotype control.
Figure 3:
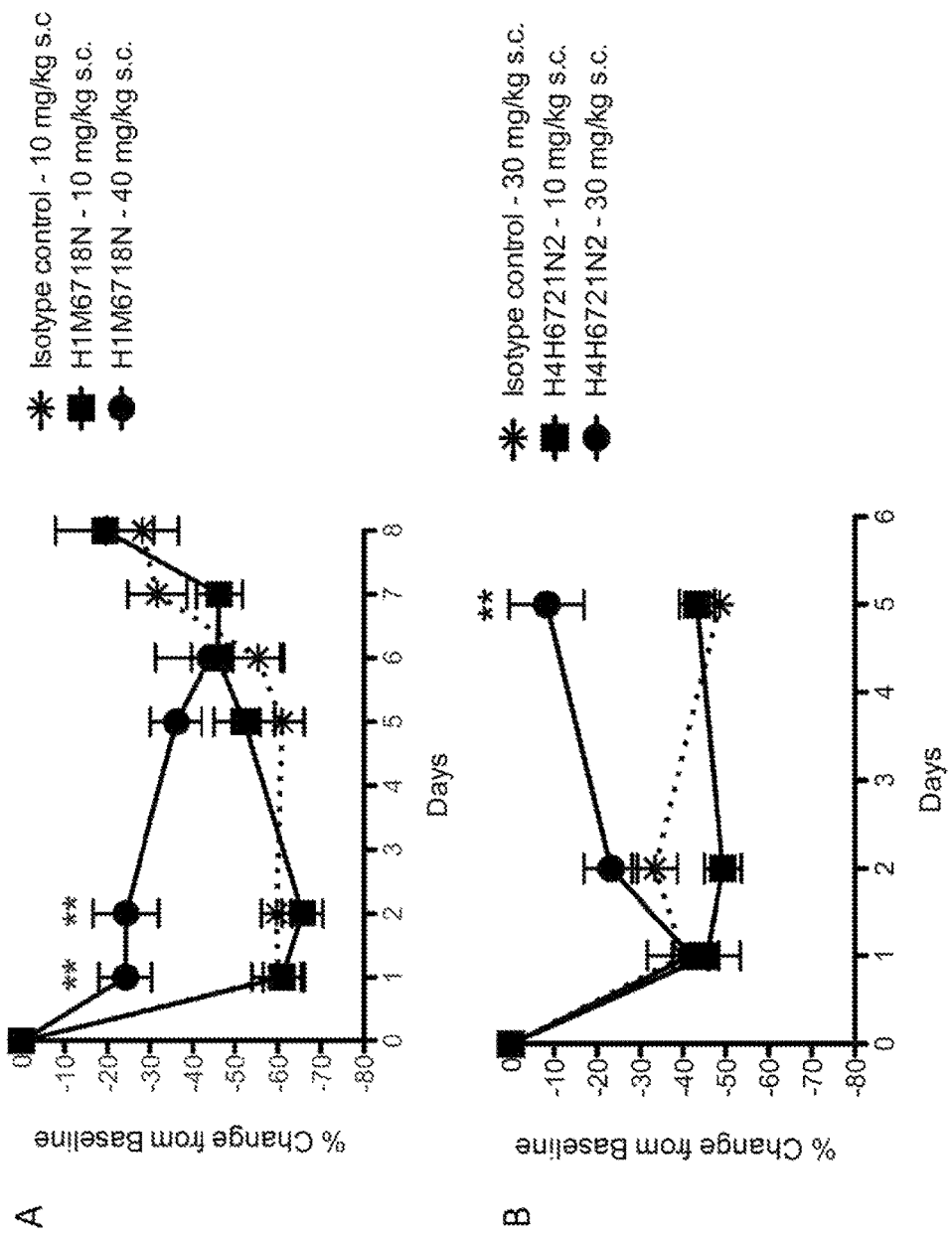
FIG. 3 (panels A and B) show the percent change in the withdrawal threshold from baseline in carrageenan-induced muscle hyperalgesia in mice treated with anti-ASIC1 antibody (H1M6718N, 10 or 40 mg/kg—panel A; or H4H6721N2 10 or 30 mg/kg—panel B), or isotype control.

The results of these experiments, as shown in FIGS. 2 and 3, are expressed in terms of the percent change in the withdrawal threshold from baseline (all data are represented as mean±SEM). For both experiments, a significant main effect of the H1M6718N treatment was observed by repeated measures ANOVA (p=0.0363 for acidic saline and 0.0193 for carrageenan). For the second experiment, a significant main effect of the H1M6721N2 treatment was observed by repeated measures ANOVA (p=0.0018). *=p<0.05 and **=p<0.01 by Bonferonni post-hoc test for the given time point. Thus, both antibodies demonstrate substantial efficacy in alleviating muscle pain in the experimental systems used herein.

Example 10

Efficacy of Anti-ASIC1 Antibody in a Model of Chemotherapy-Induced Neuropathic-Like Pain In this Example, the ability of the anti-ASIC1 antibody H4M6718N to attenuate neuropathic-like pain resulting from systemic exposure the chemotherapeutic agent taxol was assessed. Wild-type C57BL/6 male mice from Jackson Laboratory (Bar Harbor, Me.) were used in these experiments. After baseline behavioral testing, all mice received a regimen of taxol (4 mg/kg, every other day for a total of 4 doses) prior to initiating therapeutic dosing. Separate cohorts of mice received 30 mg/kg (s.c.) of an isotype control mAb, 30 mg/kg (s.c.) of H1M6718N, or 100 mg/kg (s.c.) of gabapentin. The antibodies were administered 24 hours prior to each weekly behavioral test and gabapentin was administered 2 hours prior to each weekly behavioral test. Tactile allodynia was measured in all cohorts using von Frey fibers (#58011, Stoelting Co., Wood Dale, Ill.) according to the up-down method of Dixon (Chaplan et al., *J Neurosci Methods*. 53(1):55-63). The results of this experiment are shown in FIG. 4 (all data are represented as mean±SEM).

Figure 4:
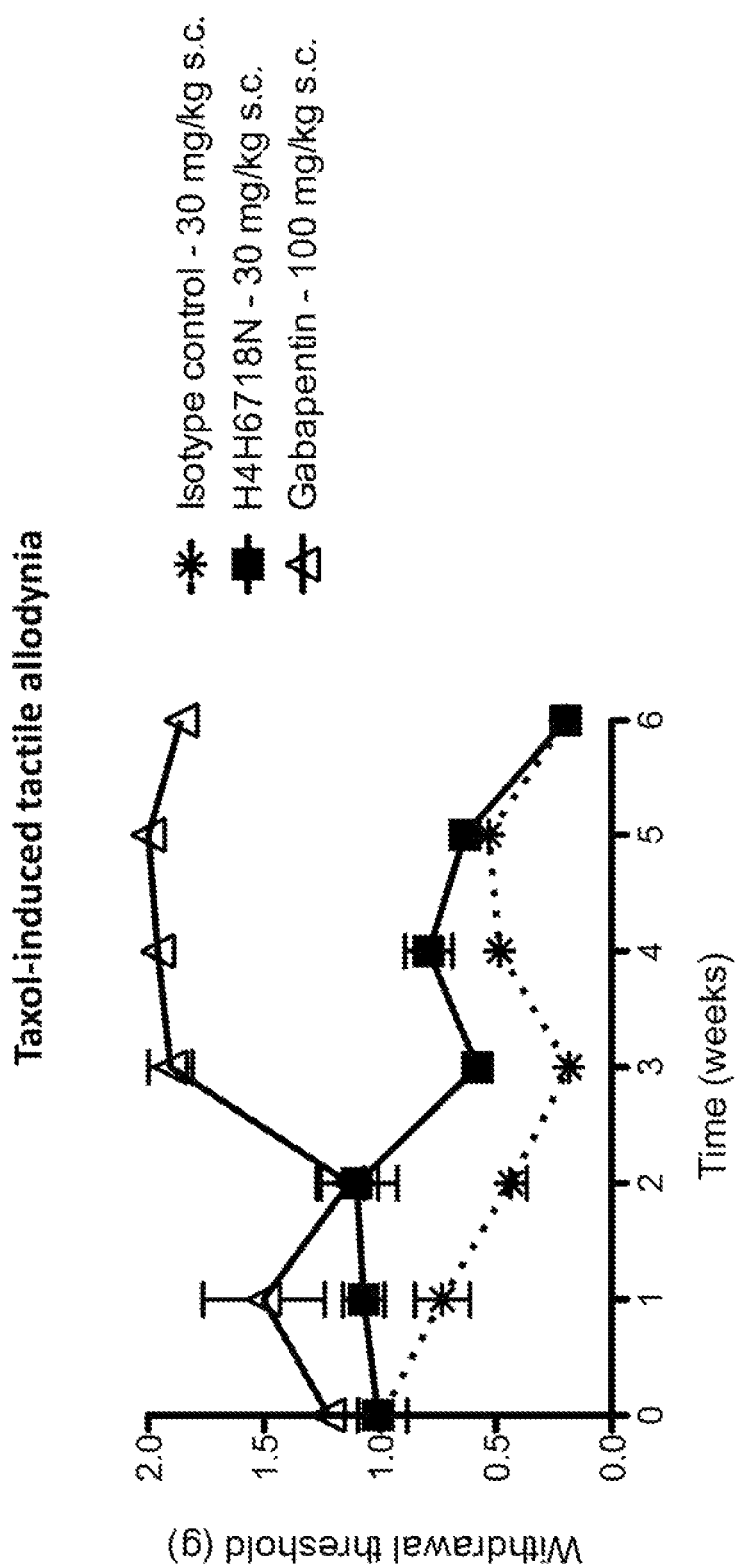
FIG. 4 shows the extent of taxol-induced tactile allodynia over time in taxol-administered mice that were treated with either 30 mg/kg (s.c.) of an isotype control antibody, 30 mg/kg (s.c.) of H1M6718N, or 100 mg/kg (s.c.) of gabapentin. Results are expressed in terms of withdrawal threshold (g) as measured using Von Frey fibers (as described in Example 10).

As illustrated in FIG. 4, a significant main effect of both H1M6718N treatment and gabapentin treatment was observed compared to the isotype control cohort by repeated measures ANOVA (p=0.0003 for H4H6718N, p<0.00001 for gabapentin). Thus, this Example suggests that anti-ASIC1 antibodies of the present invention are highly effective in alleviating chemotherapy-induced pain responses.

Collectively, the results of the foregoing Examples support the use of anti-ASIC1 blocking antibodies for the treatment of a variety of pain conditions.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated nucleic acid molecule comprising a nucleic acid sequence encoding a heavy chain variable region (HCVR) of an antibody that binds acid sensing ion channel 1 (ASIC1), wherein the HCVR comprises a heavy chain complementarity determining region 1 (HCDR1) comprising SEQ ID NO: 36, a heavy chain complementarity determining region 2 (HCDR2) comprising SEQ ID NO: 38, and a heavy chain complementarity determining region 3 (HCDR3) comprising SEQ ID NO: 40.

2. The nucleic acid molecule of claim 1, wherein the HCVR comprises the amino acid sequence of SEQ ID NO: 34.

3. The nucleic acid molecule of claim 1, wherein the HCVR comprises an HCDR1 encoded by the nucleotide sequence of SEQ ID NO:35, an HCDR2 encoded by the nucleotide sequence of SEQ ID NO:37, and an HCDR3 encoded by the nucleotide sequence SEQ ID NO: 39.

4. The nucleic acid molecule of claim 1, wherein the nucleic acid molecule comprises the nucleotide sequence of SEQ ID NO: 33 or a substantially identical sequence having at least 95% homology thereto.

5. The nucleic acid molecule of claim 1, wherein the nucleic acid molecule comprises the nucleotide sequence of SEQ ID NO: 33.

6. An isolated nucleic acid molecule comprising a nucleic acid sequence encoding a light chain variable region (LCVR) of an antibody that binds acid sensing ion channel 1 (ASIC1), wherein the LCVR comprises a light chain complementarity determining region 1 (LCDR1) comprising SEQ ID NO: 44, a light chain complementarity determining region 2 (LCDR2) comprising SEQ ID NO: 46, and a light chain complementarity determining region 3 (LCDR3) comprising SEQ ID NO: 48.

7. The nucleic acid molecule of claim 6, wherein the LCVR comprises SEQ ID NO: 42.

8. The nucleic acid molecule of claim 6, wherein the LCVR comprises an LCDR1 encoded by the nucleotide sequence of SEQ ID NO: 43, an LCDR2 encoded by the nucleotide sequence of SEQ NO:45, and an LCDR3 encoded by the nucleotide sequence of SEQ ID NO: 47.

9. The nucleic acid molecule of claim 6, wherein the nucleic acid molecule comprises the nucleotide sequence of SEQ ID NO: 41 or a substantially identical sequence having at least 95% homology thereto.

10. The nucleic acid molecule of claim 6, wherein the nucleic acid molecule comprises the nucleotide sequence of SEQ ID NO: 41.

11. An expression vector comprising:
(a) a nucleic acid molecule comprising a nucleic acid sequence encoding a heavy chain variable region (HCVR) of an antibody that binds acid sensing ion channel 1 (ASIC1), wherein the HCVR comprises a heavy chain complementarity determining region 1 (HCDR1) comprising SEQ ID NO: 36, a heavy chain complementarity determining region 2 (HCDR2) comprising SEQ ID NO: 38, and a heavy chain complementarity determining region 3 (HCDR3) comprising SEQ ID NO: 40; and (b) a nucleic acid molecule comprising a nucleic acid sequence encoding a light chain variable region (LCVR) of an antibody that binds ASIC1, wherein the LCVR comprises a light chain complementarity determining region 1 (LCDR1) comprising SEQ ID NO: 44, a light chain complementarity determining region 2 (LCDR2) comprising SEQ ID NO: 46, and a light chain complementarity determining region 3 (LCDR3) comprising SEQ ID NO: 48.

12. An isolated host cell comprising the expression vector of claim 11.

13. The host cell of claim 12, wherein the host cell is a mammalian cell or a prokaryotic cell.

14. The host cell of claim 12, wherein the host cell is a Chinese Hamster Ovary (CHO) cell or an *Escherichia coli* (*E. coil*) cell.

15. A method of producing an anti-ASIC1 antibody or antigen-binding fragment thereof, the method comprising growing the host cell of claim 12 under conditions permitting production of the antibody or antigen-binding fragment thereof, wherein said host cell comprises both a nucleic acid molecule comprising a nucleic acid sequence encoding said HCVR and a nucleic acid molecule comprising a nucleic acid sequence encoding said LCVR.

16. A composition comprising a first nucleic acid molecule and a second nucleic acid molecule;
wherein the first nucleic acid molecule comprises a nucleic acid sequence encoding a heavy chain variable region (HCVR) of an anti-acid sensing ion channel 1 (ASIC1) antibody that comprises a heavy chain complementarity determining region 1 (HCDR1) comprising SEQ ID NO: 36, a heavy chain complementarity determining region 2 (HCDR2) comprising SEQ ID NO: 38, and a heavy chain complementarity determining region 3 (HCDR3) comprising SEQ ID NO: 40; and
wherein the second nucleic acid molecule comprises a nucleic acid sequence encoding a light chain variable region (LCVR) of an anti-ASIC1 antibody that comprises a light chain complementarity determining region 1 (LCDR1) comprising SEQ ID NO: 44, a light chain complementarity determining region 2 (LCDR2) comprising SEQ ID NO: 46, and a light chain complementarity determining region 3 (LCDR3) comprising SEQ ID NO: 48.

17. The composition of claim 16, wherein the HCVR comprises SEQ ID NO: 34, and wherein the LCVR comprises SEQ ID NO: 42.

18. An isolated nucleic acid molecule encoding an antibody or antigen-binding fragment thereof, which specifically binds acid sensing ion channel 1 (ASIC1), wherein the antibody or antigen-binding fragment comprises a heavy chain variable region (HCVR) comprising three heavy chain complementarity determining regions (HCDR1, HCDR2 and HCDR3) of SEQ ID NO: 34, and a light chain variable region (LCVR) comprising three light chain complementarity determining regions (LCDR1, LCDR2 and LCDR3) of SEQ ID NO: 42.

19. The nucleic acid molecule of claim 18, wherein:
(a) the HCDR1 comprises SEQ ID NO: 36;
(b) the HCDR2 comprises SEQ ID NO: 38;
(c) the HCDR3 comprises SEQ ID NO: 40;
(d) the LCDR1 comprises SEQ ID NO: 44;
(e) the LCDR2 comprises SEQ ID NO: 46; and
(f) the LCDR3 comprises SEQ IO NO: 48.

20. The nucleic acid molecule of claim 19, wherein the HCVR comprises SEQ ID NO: 34.

21. The nucleic acid molecule of claim 19, wherein the LCVR comprises SEQ ID NO: 42.

22. The nucleic acid molecule of claim 19, wherein the HCVR comprises SEQ ID NO: 34 and the LCVR comprises SEQ ID NO: 42.

23. An expression vector comprising the nucleic acid molecule of claim 18.

24. An isolated host cell comprising the expression vector of claim 23.

25. The host cell of claim 24, wherein the host cell is a mammalian cell or a prokaryotic cell.

26. The host cell of claim 24 wherein the host cell is a Chinese Hamster Ovary (CHO) cell or an *Escherichia coli* (*E. coli*) cell.

27. A method of producing an anti-ASIC1 antibody or antigen-binding fragment thereof, comprising growing the host cell of claim 24 under conditions permitting production of the antibody or fragment, and recovering the antibody or antigen-binding fragment thereof so produced.

* * * * *